United States Patent
Getts et al.

(10) Patent No.: US 12,338,435 B2
(45) Date of Patent: *Jun. 24, 2025

(54) NUCLEIC ACID CARRIERS AND THERAPEUTIC METHODS OF USE

(71) Applicant: Code Biotherapeutics, Inc., Hatfield, PA (US)

(72) Inventors: Robert C. Getts, Hatfield, PA (US); James M. Kadushin, Hatfield, PA (US); Lori Getts, Hatfield, PA (US)

(73) Assignee: Code Biotherapeutics, Inc., Hatfield, PA (US)

(*) Notice: Subject to any disclaimer, the term of this patent is extended or adjusted under 35 U.S.C. 154(b) by 871 days.

This patent is subject to a terminal disclaimer.

(21) Appl. No.: 15/999,774

(22) PCT Filed: Feb. 17, 2017

(86) PCT No.: PCT/US2017/018323
§ 371 (c)(1),
(2) Date: Aug. 20, 2018

(87) PCT Pub. No.: WO2017/143156
PCT Pub. Date: Aug. 24, 2017

(65) Prior Publication Data
US 2021/0213138 A1    Jul. 15, 2021

Related U.S. Application Data

(60) Provisional application No. 62/297,194, filed on Feb. 19, 2016.

(51) Int. Cl.
*C12N 15/11* (2006.01)
*A61K 47/56* (2017.01)
*A61K 47/68* (2017.01)

(52) U.S. Cl.
CPC ............ *C12N 15/111* (2013.01); *A61K 47/56* (2017.08); *A61K 47/6803* (2017.08); *A61K 47/68031* (2023.08); *A61K 47/6881* (2017.08); *A61K 47/6885* (2017.08); *C12N 2310/3513* (2013.01); *C12N 2320/32* (2013.01)

(58) Field of Classification Search
CPC .... A61K 47/00; A61K 47/6885; A61K 47/56; A61K 47/6803; A61K 47/6881; A61K 47/549; A61K 47/6851; A61K 38/00; C12N 15/111; C12N 2310/3513; C12N 2320/32; A61P 1/00; A61P 7/00; A61P 11/00; A61P 13/08; A61P 15/00; A61P 17/00; A61P 25/00; A61P 35/00; A61P 35/02; A61P 35/04; A61P 37/04
USPC .............. 424/1.11, 1.49, 1.65, 1.73, 9.1, 9.2
See application file for complete search history.

(56) References Cited

U.S. PATENT DOCUMENTS

| | | |
|---|---|---|
| 3,641,235 A | 2/1972 | Rozman |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,959,078 A | 5/1976 | Guire |
| 3,966,897 A | 6/1976 | Renn et al. |
| 3,984,533 A | 10/1976 | Uzgiris |
| 3,996,345 A | 12/1976 | Ullman et al. |
| 4,034,074 A | 7/1977 | Miles |
| 4,094,647 A | 6/1978 | Deutsch et al. |
| 4,098,876 A | 7/1978 | Piasio et al. |
| 4,168,146 A | 9/1979 | Grubb et al. |
| 4,196,281 A | 4/1980 | Hearst et al. |
| 4,299,916 A | 11/1981 | Litman et al. |
| 4,347,312 A | 8/1982 | Brown et al. |
| 4,366,241 A | 12/1982 | Tom et al. |
| 4,391,904 A | 7/1983 | Litman et al. |
| 4,425,438 A | 1/1984 | Bauman et al. |
| 4,517,288 A | 5/1985 | Giegel et al. |
| 4,639,425 A | 1/1987 | Baier |
| 4,666,828 A | 5/1987 | Gusella |
| 4,683,202 A | 7/1987 | Mullis |
| 4,695,554 A | 9/1987 | O'Connell et al. |
| 4,703,017 A | 10/1987 | Campbell et al. |
| 4,743,560 A | 5/1988 | Campbell et al. |
| 4,801,531 A | 1/1989 | Frossard |
| 4,857,453 A | 8/1989 | Ullman et al. |
| 4,879,219 A | 11/1989 | Wands et al. |

(Continued)

FOREIGN PATENT DOCUMENTS

| | | |
|---|---|---|
| EP | 0149168 A1 | 7/1985 |
| EP | 0250137 A2 | 12/1987 |

(Continued)

OTHER PUBLICATIONS

Getts et al., "Platform Technology: The 3DNA Platform for Targeted Drug Dilivery", Drug Development & Delivery, 2016, 16(9), pp. 39-43.

Gong et al., "Simple Method to Prepare Oligonucleotide-Conjugated Antibodies and Its Application in Multiplex Protein Detection in Single Cells", Bioconjugate Chemistry, 2016, 27(1), pp. 217-225.

(Continued)

*Primary Examiner* — Jennifer Chin
(74) *Attorney, Agent, or Firm* — Goodwin Procter LLP

(57) ABSTRACT

The present disclosure provides nucleic acid carriers comprising targeting agents, pharmaceutical compositions comprising the same, and methods of making and using the same.

7 Claims, 12 Drawing Sheets
Specification includes a Sequence Listing.

(56) References Cited

U.S. PATENT DOCUMENTS

| | | |
|---|---|---|
| 4,956,302 A | 9/1990 | Gordon et al. |
| 4,960,691 A | 10/1990 | Gordon et al. |
| 5,011,771 A | 4/1991 | Bellet et al. |
| 5,073,484 A | 12/1991 | Swanson et al. |
| 5,075,078 A | 12/1991 | Osikowicz et al. |
| 5,120,643 A | 6/1992 | Ching et al. |
| 5,141,875 A | 8/1992 | Kelton et al. |
| 5,168,053 A | 12/1992 | Altman et al. |
| 5,175,270 A | 12/1992 | Nilsen et al. |
| 5,192,659 A | 3/1993 | Simons |
| 5,252,496 A | 10/1993 | Kang et al. |
| 5,272,057 A | 12/1993 | Smulson et al. |
| 5,275,785 A | 1/1994 | May et al. |
| 5,281,521 A | 1/1994 | Trojanowski et al. |
| 5,416,016 A | 5/1995 | Low et al. |
| 5,484,904 A | 1/1996 | Nilsen et al. |
| 5,487,973 A | 1/1996 | Nilsen et al. |
| 5,504,013 A | 4/1996 | Senior |
| 5,514,602 A | 5/1996 | Brooks, Jr. et al. |
| 5,580,859 A | 12/1996 | Felgner et al. |
| 5,591,645 A | 1/1997 | Rosenstein |
| 5,602,040 A | 2/1997 | May et al. |
| 5,653,979 A | 8/1997 | Muzykantov et al. |
| 5,656,448 A | 8/1997 | Kang et al. |
| 5,712,170 A | 1/1998 | Kouvonen et al. |
| 5,846,737 A | 12/1998 | Kang |
| 6,017,767 A | 1/2000 | Chandler |
| 6,046,038 A | 4/2000 | Nilsen |
| 6,072,043 A | 6/2000 | Nilsen |
| 6,110,687 A | 8/2000 | Nilsen |
| 6,117,631 A | 9/2000 | Nilsen |
| 6,156,271 A | 12/2000 | May |
| 6,180,357 B1 | 1/2001 | Young et al. |
| 6,187,269 B1 | 2/2001 | Lancesseur et al. |
| 6,187,598 B1 | 2/2001 | May et al. |
| 6,274,723 B1 * | 8/2001 | Nilsen .................. C12Q 1/6813 536/2 |
| 6,319,676 B1 | 11/2001 | Nazareth et al. |
| 6,335,435 B1 | 1/2002 | Shimamoto et al. |
| 6,352,862 B1 | 3/2002 | Davis et al. |
| 6,399,398 B1 | 6/2002 | Cunningham et al. |
| 6,485,982 B1 | 11/2002 | Charlton |
| 6,488,927 B2 | 12/2002 | Muzykantov et al. |
| 6,528,631 B1 | 3/2003 | Cook et al. |
| 6,534,281 B2 | 3/2003 | Kitajima et al. |
| 6,656,730 B1 | 12/2003 | Manoharan |
| 6,656,744 B2 | 12/2003 | Pronovost et al. |
| RE38,430 E | 2/2004 | Rosenstein |
| 6,770,487 B2 | 8/2004 | Crosby |
| 6,773,928 B1 | 8/2004 | Yin et al. |
| 6,822,086 B1 | 11/2004 | Papisov |
| 6,861,514 B2 | 3/2005 | Cook et al. |
| 6,919,439 B2 | 7/2005 | Manoharan et al. |
| 7,041,287 B2 | 5/2006 | Muzykantov et al. |
| 7,144,742 B2 | 12/2006 | Boehringer et al. |
| 7,157,087 B2 | 1/2007 | Muzykantov et al. |
| 7,172,760 B2 | 2/2007 | Muzykantov et al. |
| 7,175,992 B2 | 2/2007 | Fong |
| 7,189,522 B2 | 3/2007 | Esfandiari |
| RE39,664 E | 5/2007 | Gordon et al. |
| 7,223,544 B2 | 5/2007 | Luo et al. |
| 7,238,538 B2 | 7/2007 | Freitag et al. |
| 7,258,837 B2 | 8/2007 | Yager et al. |
| 7,317,532 B2 | 1/2008 | Sharrock et al. |
| 7,674,466 B2 | 3/2010 | Muzykantov et al. |
| 7,691,997 B2 | 4/2010 | Khvorova et al. |
| 7,879,597 B2 | 2/2011 | Esfandiari |
| 9,651,549 B2 | 5/2017 | Casta et al. |
| 9,707,299 B2 | 7/2017 | Muro-Galindo et al. |
| 11,149,302 B2 | 10/2021 | Rothwell et al. |
| 11,802,151 B2 * | 10/2023 | Getts .................. C07K 16/28 |
| 2001/0036460 A1 | 11/2001 | Sawicki |
| 2002/0001580 A1 | 1/2002 | Hermonat et al. |
| 2002/0072060 A1 | 6/2002 | Getts et al. |
| 2003/0224490 A1 | 12/2003 | Dessain et al. |
| 2004/0023248 A1 | 2/2004 | O'Malley |
| 2004/0157330 A1 | 8/2004 | Sheridan et al. |
| 2004/0171571 A1 | 9/2004 | Krieg et al. |
| 2004/0220084 A1 | 11/2004 | Sandhu |
| 2004/0249178 A1 | 12/2004 | Vargeese et al. |
| 2005/0089890 A1 | 4/2005 | Cubicciotti |
| 2005/0130180 A1 | 6/2005 | Luo et al. |
| 2005/0215507 A1 | 9/2005 | Anderson et al. |
| 2005/0281845 A1 | 12/2005 | Bachmann et al. |
| 2006/0040879 A1 | 2/2006 | Kosak |
| 2006/0160098 A1 | 7/2006 | Zak et al. |
| 2006/0168670 A1 | 7/2006 | Lee et al. |
| 2006/0228404 A1 | 10/2006 | Anderson et al. |
| 2006/0246035 A1 | 11/2006 | Ahluwalia et al. |
| 2007/0065451 A1 | 3/2007 | Muzykantov et al. |
| 2007/0173473 A1 | 7/2007 | McSwiggen et al. |
| 2007/0225213 A1 | 9/2007 | Kosak |
| 2008/0050389 A1 | 2/2008 | Muzykantov et al. |
| 2008/0145440 A1 | 6/2008 | Cho et al. |
| 2008/0242851 A1 | 10/2008 | Khvorova et al. |
| 2009/0011956 A1 | 1/2009 | Yin et al. |
| 2009/0012022 A1 | 1/2009 | Milner et al. |
| 2009/0130104 A1 | 5/2009 | Muzykantov et al. |
| 2009/0234109 A1 | 9/2009 | Han et al. |
| 2009/0297479 A1 | 12/2009 | Ariizumi et al. |
| 2010/0112725 A1 | 5/2010 | Babu et al. |
| 2010/0129437 A1 | 5/2010 | Gaillard |
| 2010/0136614 A1 | 6/2010 | Luo et al. |
| 2010/0151005 A1 | 6/2010 | Muro-Galindo et al. |
| 2010/0190179 A1 | 7/2010 | Nilsen |
| 2010/0323018 A1 | 12/2010 | Irvine et al. |
| 2011/0160090 A1 | 6/2011 | Cary |
| 2011/0256054 A1 | 10/2011 | Menko et al. |
| 2012/0122800 A1 | 5/2012 | Kadushin et al. |
| 2012/0149647 A1 | 6/2012 | Brody et al. |
| 2013/0018086 A1 | 1/2013 | Goldberg |
| 2013/0171740 A1 | 7/2013 | Sakakibara |
| 2014/0017704 A1 | 1/2014 | Casta et al. |
| 2014/0074219 A1 | 3/2014 | Hingston et al. |
| 2014/0127255 A1 | 5/2014 | Fearon et al. |
| 2014/0212503 A1 | 7/2014 | Lee et al. |
| 2015/0037358 A1 | 2/2015 | George-Weinstein et al. |
| 2015/0177235 A1 | 6/2015 | Casta et al. |
| 2015/0272980 A1 | 10/2015 | Rodrigueza et al. |
| 2015/0359907 A1 | 12/2015 | Getts et al. |
| 2016/0051693 A1 | 2/2016 | Getts et al. |
| 2017/0209599 A1 | 7/2017 | Getts et al. |
| 2017/0296675 A1 | 10/2017 | Muro-Galindo et al. |
| 2017/0312299 A1 | 11/2017 | Getts et al. |
| 2018/0117166 A1 | 5/2018 | Getts et al. |
| 2021/0162064 A1 | 6/2021 | Getts et al. |

FOREIGN PATENT DOCUMENTS

| | | |
|---|---|---|
| EP | 0323605 A2 | 7/1989 |
| EP | 404097 A2 | 12/1990 |
| EP | 586590 A1 | 3/1994 |
| EP | 1319179 A2 | 6/2003 |
| GB | 1526708 A | 9/1978 |
| JP | 2001503517 A | 3/2001 |
| JP | 2001512034 A | 8/2001 |
| JP | 2004505892 A | 2/2004 |
| JP | 2005529606 A | 10/2005 |
| JP | 2008195613 A | 8/2008 |
| JP | 2011530537 A | 12/2011 |
| JP | 2013520516 | 6/2013 |
| JP | 2015522265 | 8/2015 |
| WO | 1987002671 A1 | 5/1987 |
| WO | 9010716 A1 | 9/1990 |
| WO | 9207065 A1 | 4/1992 |
| WO | 1993011161 A1 | 6/1993 |
| WO | 1995024221 | 9/1995 |
| WO | 1996030047 A1 | 10/1996 |
| WO | 1996034629 A1 | 11/1996 |
| WO | 9818488 A1 | 5/1998 |
| WO | 9906595 A1 | 2/1999 |
| WO | 9940438 A1 | 8/1999 |
| WO | 1999045960 A1 | 9/1999 |
| WO | 1999059611 A1 | 11/1999 |

(56) References Cited

FOREIGN PATENT DOCUMENTS

| | | |
|---|---|---|
| WO | 2000007625 A1 | 2/2000 |
| WO | 2001087350 A2 | 11/2001 |
| WO | 03033735 A2 | 4/2003 |
| WO | 2004072117 A2 | 8/2004 |
| WO | 2004100885 A2 | 11/2004 |
| WO | 2005005957 A2 | 1/2005 |
| WO | 2005113571 A2 | 12/2005 |
| WO | 2006098804 A2 | 9/2006 |
| WO | 2006099191 A2 | 9/2006 |
| WO | 2006128152 A2 | 11/2006 |
| WO | 2008039206 A2 | 4/2008 |
| WO | 2008147526 | 12/2008 |
| WO | 2009018500 | 2/2009 |
| WO | 2009080832 A1 | 7/2009 |
| WO | 2009086552 A1 | 7/2009 |
| WO | 2009137055 A1 | 11/2009 |
| WO | 2010017544 | 2/2010 |
| WO | 2010045518 A1 | 4/2010 |
| WO | 2010065920 A1 | 6/2010 |
| WO | 2010128087 A2 | 11/2010 |
| WO | 2011103074 A1 | 8/2011 |
| WO | 2011106481 | 9/2011 |
| WO | 2012032794 A1 | 3/2012 |
| WO | 2012061402 A2 | 5/2012 |
| WO | 2012145469 A1 | 10/2012 |
| WO | 2013134768 A1 | 9/2013 |
| WO | 2014012077 A1 | 1/2014 |
| WO | 2014121050 | 8/2014 |
| WO | WO-2014121050 A1 * 8/2014 ............ A61K 38/45 |
| WO | 2014153394 | 9/2014 |
| WO | 2015077891 | 6/2015 |
| WO | 2016168578 | 10/2016 |
| WO | 2017143156 A1 | 8/2017 |
| WO | 2017143171 A1 | 8/2017 |

OTHER PUBLICATIONS

Huang et al., "Delivery of Therapeutics Targeting the mRNA-Binding Protein HuR Using 3DNA Nanocarriers Suppresses Ovarian Tumor Growth", Cancer Research, 2016, 76(6), pp. 1549-1559.

Muro, "A DNA Device that Mediates Selective Endosomal Escape and Intracellular Delivery of Drugs and Biologicals", Advanced Functional Materials, 2014, 24(19), pp. 2899-2906.

Nilsen et al., "Dendritic Nucleic Acid Structures", Journal of Theoretical Biology, 1997, 187, pp. 273-284.

Zhang et al., "Antibody-Linked Spherical Nucleic Acids for Cellular Targeting", Journal of the American Chemical Society, 2012, 134(40), pp. 16488-16491.

Genisphere, "Functional delivery of miR-218 precursor in primary bronchial epithelial cells using 3DNA Nanotechnology Introduction", XP055620580, retrieved from the internet: URL:http://genisphere.com/sites/default/files/Functional%20Delivery%20of%20miR-218%20precursor%20in%20primary%20bronchial%20epithelial%20cells%20using%203DNA%20Nanotechnology.pdf.

Abderrezak et al., "Dendrimers Bind Antioxidant Polyphenols and cisPlatin Drug," PLoS One (2012) 7(3): e33102. (Year: 2012).

Adhikary, G., et al., "Identification of a Population of Epidermal Squamous Cell Carcinoma Cells with Enhanced Potential for Tumor Formation" PLoS One (2013) 8(12): e84324.

Agarwal et al., "Dextran Conjugated Dendritic Nanoconstructs as Potential Vectors for Anti-Cancer Agent," Biomaterials (2009) 30, pp. 3588-3596.

Al-Ahmadi et al., "miR-29a inhibition normalizes HuR overexpression and aberrant AU-rich mRNA stability in invasive cancer", Journal of Pathology, May 2013, vol. 230, No. 1, 11 pages.

Almenar-Queralt et al, Apical topography and modulation of ICAM-1 expression on activated endothelium, American Journal of Pathology, 147(5):1278-88 (Nov. 2005).

Anderson et al., "A Polymer Library Approach to Suicide Gene Therapy for Cancer," PNAS (Nov. 9, 2004) vol. 101, No. 45, pp. 16028-16033.

Andl et al., "Epithelial Bmpr1a regulates differentiation and proliferation in postnatal hair follicles and is essential for tooth development", Development, vol. 131, 2004, pp. 2257-2268.

Anwer et al, "Targeted Gene Delivery: A Two-Pronged Approach", Crit. Rev. Ther. Drug Carrier Syst. 17(4): 377-424, 2000; abstract only.

Arya et al, Enhanced anti proliferative activity of Herceptin (HER2)-conjugated gemcitabine-loaded chitosan nanoparticle in pancreatic cancer therapy, Nanomedicine: Nanotechnology, Biology, and Medicine 7: 859-870, 2011.

Ben-Yair et al., "Lineage analysis of the avian dermomyotome sheet reveals the existence of single cells with both dermal and muscle progenitor fates", Development, vol. 132, 2005, pp. 689-701.

Bonazzi et al, Bacterial entry into cells: a role for the endocytic machinery, FEBS Letters, 580(12):2962-7 (May 2006).

Borucki et al., "Suspension Microarray with Dendrimer Signal Amplification Allows Direct and High-Throughput Subtyping of Listeria Monocytogenes with Genomic DNA," Journal of Clinical Microbiology (2005) vol. 43, No. 7, pp. 3255-3259.

Botchkarev et al., "Noggin is required for induction of the hair follicle growth phase in postnatal skin", FASEB J., vol. 15, 2001, pp. 2205-2214.

Botchkarev, V.A., "Bone Morphogenetic Proteins and Their Antagonists in Skin and Hair Follicle Biology", J. Invest. Dermatol., vol. 120, 2003, pp. 36-47.

Chakravarty et al., "Thermal ablation of tumor cells with antibody-functionalized single-walled carbon nanotubes", PNAS, vol. 105, 2008, pp. 8697-8702.

Chang et al., "Aptamer-Conjugated DNA Icosahedral Nanoparticles as a Carrier of Doxorubicin for Cancer Therapy," ACS NANO (Aug. 23, 2011) vol. 5, No. 8, pp. 6156-6163.

Chavali et al., "Oligonucleotide properties determination and primer designing: a critical examination of predictions", Bioinformatics, 2005, vol. 21(20), pp. 3918-3925.

Chen et al. Matrix contraction by dermal fibroblasts requires TGFbeta/ALK5, heparan sulfate containing proteoglycans and MEK/ERK: Insights into pathological scarring in chronic fibrotic disease . . . Am J Pathol 2005, 167:1699-1711.

Chen et al., "Synthesis of Antisense Oligonucleotide-Peptide Conjugate Targeting to GLUT-1 in HepG-2 and MCF-7 Cells", Bioconjugate Chem., 2002, vol. 13(3), pp. 525-529.

Cho et al., "Therapeutic Nanoparticles for Drug Delivery in Cancer", CLIN, 2008 Cancer Res., vol. 14, pp. 1310-1316.

Choy et al., "Tunable pH-Sensitive Linker for Controlled Release", Bioconjugate Chem., 2016, vol. 27(3), pp. 824-830.

Conner et al, Regulated portals of entry into the cell, Nature, 422(6927):37-44 (Mar. 2003).

Cornelison et al. Essential and separable roles for syndecans-3 and syndecan-4 in skeletal muscle development and regeneration. Genes & Development 18:2231-2236, 2004.

Cornelison et al. Syndecan-3 and Syndecan-4 Specifically Mark Skeletal Muscle Satellite Cells and Are Implicated in Satellite Cell Maintenance and Muscle Regeneration. Developmental Biology 239, 79-94 (2001).

Dawson et al., "Synthesis of Native Proteins by Chemical Ligation", Ann. Rev. Biochem., vol. 69, 2000, pp. 923-960.

Derfus et al., Targeted quantum dot conjugates for siRNA delivery, 2007, Bioconjugate Chemistry, vol. 18, pp. 1391-1396.

Dermaut et al., "Aberrant lysosomal carbohydrate storage accompanies edocytic defects and neurodegeneration in *Drosophila benchwarmer*", Jcell Biol., vol. 170, 2005, pp. 127-139.

Dhami et al., "Mannose 6-Phosphate Receptor-mediated Uptake Is Defective in Acid Sphingomyelinase-deficient Macrophages", J Biol Chem., vol. 279, 2004, pp. 1526-1532.

Edwards et al., "The Remarkable Flexibility of the Human Antibody Repertoire; Isolation of Over One Thousand Different Antibodies to a Single Protein, BLyS", J Mol Biol. 334(1): 103-118 (Year: 2003).

Feng et al., "Enhanced Immune Response and Protective Effects of Nano-chitosan-based DNA Vaccine Encoding T Cell Epitopes of Esat-6 and FL against *Mycobacterium* Tuberculosis Infection", PLoS One, 2013, vol. 8(4), pp. 1-10.

Friedlander, M. "Fibrosis and diseases of the eye." J Clin Invest. Mar. 2007;117(3):576-86.

(56) References Cited

OTHER PUBLICATIONS

Gabbiani, G., "The myofibroblast in wound healing and fibrocontractive diseases", J. Pathol., vol. 200, 2003, pp. 500-503.
Geiszt, "Chronic granulomatous disease: more than the lack of superoxide?", J Leukoc Biol, vol. 69, No. 2, 2001, pp. 191-196.
GenBank, Database accession No. AK298000.
GenBank, Database accession No. AK304337.
GenBank, Database accession No. NM_003750.2.
GenBank, Database accession No. NM_015904.3.
GenBank, Database accession No. NP 002989.
GenBank, Database accession No. NP 002990.
GenBank, Database accession No. NP 055469.
GenBank, Database accession No. NP_001006947.
GenBank, Database accession No. NP_003741.1.
GenBank, Database accession No. NP_056988.3.
GenBank, Database accession No. P46940.
GenBank, Database accession No. Q05DN7.
GenBank, Database accession No. Q5FWG8.
GenBank, Database accession No. Q6P1N4.
GenBank, Database accession No. Q96PA3.
Genisphere, "Functional delivery of miR-218 precursor in primary bronchial epithelial cells using 3DNA Nanotechnology Introduction", XP055620580, retrieved from the internet: URL:http:/Igenisphere.com/sites/default/files/Functional%20Delivery%20of%20miR-218%20precursor%20in%20primary%20bronchial%20epithelial%20cells%20using%203DNA %20Nanotechnology.pdf.
Gerhart et al. (2000) "DNA dendrimers localize MyoD mRNA in presomitic tissues of the chick embryo", J. Cell Biol., 149:825-834.
Gerhart et al. (2011) "Myo/Nog cell regulation of bone morphogenetic protein signaling in the blastocyst is essential for normal morphogenesis and striated muscle lineage specification", Dev. Biol., 359:12-25.
Gerhart et al. (2012) "Myo/Nog cells in normal, wounded and tumor-bearing skin", Dev. Biol., 21 (6):466-8.
Gerhart, J., et al. "Cells that express MyOD mRNA in the epiblast are stably committed to the skeletal muscle lineage." J Cell Biol. Aug. 13, 2007;178(4):649-60.
Gerhart, J., et al. "Epiblast cells that express MyoD recruit pluripotent cells to the skeletal muscle lineage." J Cell Biol. Mar. 1, 2004 ;164(5):739-46. Epub Feb. 23, 2004.
Gerhart, J., et al. "MyoD-positive epiblast cells regulate skeletal muscle differentiation in the embryo." J Cell Biol. Oct. 23, 2006;175(2):283-92.
Gerhart, J., et al. "Noggin producing, MyoD-positive cells are crucial for eye development." Dev Biol. Dec. 1, 2009;336(1):30-41. Epub Sep. 22, 2009.
Gerhart, J., et al. "Tracking and ablating subpopulations of epiblast cells in the chick embryo." Biol Proced Online. Sep. 1, 2008 ;10:74-82.
Gerhart, J., et al., "Antibody-Conjugated, DNA-Based Nanocarriers Intercalated with Doxorubicin Eliminate Myofibroblasts in Explants of Human Lens Tissue" J_ Pharmacol. Exp_ Ther. (2017) 361 :60-67.
Gharzi et al., "Plasticity of hair follicle dermal cells in wound healing and induction ", Exp. Dermatol., vol. 12, 2003, pp. 126-136.
Goel et al, "Plasticity within the Antigen-Combining Site May Manifest as Molecular Mimicry in the Humoral Immune Response", J. Immunol. 173: 7358-7367, 2004.
Haussecker, Dirk "Is Dendrimer-siRNA Delivery Reaching Critical Mass?", htt12://rnaithera12eutics.blogs12ot.com/2009/09/is-dendrimer-sirna-delive!Yreachina. html Sep. 30, 2009, 17 pgs.
Hawtin, et al., "Voreloxin Is an Anticancer Quinolone Derivative that Intercalates DNA and Poisons Topoisomerase II", PLoS One vol. 5 Issue 4 e10186, Apr. 2010, 10 pages.
Hayes et al., "A prolonged and exaggerated wound response with elevated ODC activity mimics early tumor development", Carcinogenesis, vol. 32, 2011, pp. 1340-1348.

Hayes et al., "Elevated levels of ornithine decarboxylase cooperate with Raf/ERK activation to convert normal keratinocytes into invasive malignant cells", Oncogene, vol. 25, 2006, pp. 1543-1553.
Herfs, et al., "A discrete population of squamocolumnar junction cells implicated in the pathogenesis of cervical cancer", PNAS, 2012, vol. 109, No. 26, pp. 10516-10521, and Supporting Information, 10 pgs.
Hsu et al., "Aggressive melanoma cells escape from BMP7-mediated autocrine growth inhibition through coordinated Noggin upregulation", Lab Invest., vol. 88, 2008, pp. 842-855.
Ikeda et al, "The Monoclonal Antibody nBT062 Conjugated to Cytotoxic Maytansinoids Has Selective Cytotoxicity Against CD138-Positive Multiple Myeloma Cells In vitro and In vivo", Clin Cancer Res, 2009, 15(12): 4028-4037.
International Preliminary Report on Patentability for PCT/US2017/018323 mailed Aug. 21, 2018; W02017143156; 10 pages.
International Search Report and Written Opinion for PCT/US2017/018323 mailed May 4, 2017; WO02017143156; 12 pages.
Jamora et al., "Links between signal transduction, transcription and adhesion in epithelial bud development", Nature, vol. 422, 2003, pp. 317-322.
Jejurikar and Kuzon. Satellite cell depletion in degenerative skeletal muscle. Apoptosis 2003; 8: 573-578.
Juliano, "Peptide-oligonucleotide conjugates for the delivery of antisense and siRNA", Curr Opin Mol. Ther., 2005, vol. 7(2), pp. 132-136.
Ke et al., Two design strategies for enhancement of multilayer-DNA-origami folding: underwinding for specific intercalator rescue and staple-break positioning. Chem. Sci. 3, 2587-2597 (2012).
Keen et al., Publication date:2008-10-01, "A step towards a new targeted nanotherapy for pancreatic cancer", Source: Cancer biology & therapy, Oct. 1, 2008, Landes Bioscience, US, Interregnum: ISSN 1538-4047, DOI: https://dx.doi.org/10.4161/cbt.7.10.6758, Source details: vol. 7, Nr.: 10, XP055483288, pp. 1591-1592.
Kobielak et al., "Loss of a quiescent niche but not follicle stem cells in the absence of bone morphogenetic protein signaling", Proc. Natl. Acad. Sci., vol. 104, 2007, pp. 10063-10068.
Lang et al., "Pax3 functions at a nodal point in melanocyte stem cell differentiation", Nature, vol. 433, 2005, pp. 884-887.
Leask et al. Matrix contraction by dermal fibroblasts requires syndecan 4: Insights into pathological scarring in chronic fibrotic disease. The FAS EB Journal. 2006;20:A 1098). Abstract 688.8.
Li et al, Controlled assembly of dendrimer-like DNA, Nature Materials, 3(1):38-42 (Jan. 2004).
Li et al, Multiplexed detection of pathogen DNA with DNA-based fluorescence nanobarcodes, Nature Biotechnology, 23(7):885-9 (Jul. 2005).
Lisgarten, et al., "The antimalarial and cytotoxic drug cryptolepine intercalates into DNA at cytosine-cytosine sites", Nature Structural Biology vol. 9 No. 1, Jan. 2002, 57-60.
Lloyd et al., "Modelling the human immune response: performance of a 1011 human antibody repertoire against a broad panel of therapeutically relevant antigens", Protein Engineering, Design & Selection 2009, 22: 159-168 (Year: 2009).
Lowe et al, Multiplexed, particle-based detection of DNA using flow cytometry with 3DNA dendrimers for signal amplification, Cytometry A, 60(2):135-44 (Aug. 2004).
Lugini et al., "Cannibalism of Live Lymphocytes by Human Metastatic but Not Primary Melanoma Cells", Cancer Res., vol. 66, 2006, pp. 3629-3638.
Marchan et al., "Diels-Alder cycloadditions in water for the straightforward preparation of peptide-oligonucleotide conjugates", Nucleic Acids Research, 2006, vol. 34(3), pp. 1-9.
Melikov et al, Arginine-dch cell penetrating peptides: from endosornal uptake to nuclear delivery, Cellular and Molelecular Life Sciences, 62(23):2739-49 (Dec. 2005).
Mittal et al., "Dendrimers: A New Race of Pharmaceutical Nanocarriers", BiolMed Research International, vol. 202 I, Article ID 8844030, https://doi.org/10.1155/2021/8844030, Received 2020—Publication Feb. 16, 2021, 11 pages.
Mizuno et al., "Simultaneous Delivery of Doxorubicin and Immunostimulatory CpG Motif to Tumors Using a Plasmid DNA/

(56) References Cited

OTHER PUBLICATIONS

Doxorubicin Complex in Mice," Journal of Controlled Release (Jan. 25, 2010) vol. 141, No. 2, pp. 252-259.
Montanaro et al., "Skeletal muscle engraftment potential of adult mouseskin side population cells", Proc. Natl. Acad. Sci., vol. 100, 2003, pp. 9336-9341.
Mora et al, Dendrimer FISH detection of single-copy intervals in acute promyelocytic leukemia, Molecular and Cellular Probes, 20(2): 114-20 (Apr. 2006).
Mora et al., "Protein Detection Enhanced by 3DNA Dendrimer Signal Amplification," BioTechniques (2008) vol. 44, No. 6, pp. 815-818.
Muralidharan et al., "Folate receptor-targeted nanoparticle delivery of HuR-RNA supresses lung cancer cell proliferation and migration", Journal of Nanobiotechnology, 2016, vol. 14(47), pp. 1-17.
Muralidharan et al., "Tumor-targeted nanoparticle delivery of HuR-RNAi suppresses lung cancer cell proliferation and cell migration", Cancer Research, Oct. 2014, vol. 74, Abstract No. 5418, pp. 1-2.
Murciano et al, ICAM-directed vascular immunotargeting of antithrombotic agents to the endothelial luminal surface, Blood, 101(10): 3977-3984 (May 2003).
Muro et al, A novel endocytic pathway induced by clustering endothelial ICAM-1 or PECAM-1, Journal of Cell Science, 116 Pt 8 :1599-609 Apr. 2003).
Muro et al, Control of intracellular trafficking of ICAM-1-targeted nanocarriers by endothelial Na+/H+ exchanger proteins, American Journal of Physiology. Lung Cellular and Molecular Physiology, 290 (5):L809-I 7 (May 2006).
Muro et al, ICAM-1 recycling in endothelial cells: a novel pathway for sustained intracellular delivery and prolonged effects of drugs, Blood, 105(2):650-8 (Jan. 2005).
Muro et al, Lysosomal enzyme delivery by ICAM-1-targeted nanocarriers bypassing glycosylation- and clathrin-dependent endocytosis, Molecular Therapy, 13(1):135-41 (Jan. 2006).
Muro et al, Slow intracellular trafficking of catalase nanoparticles targeted to ICAM-1 protects endothelial cells from oxidative stress, American Journal of Physiology. Cell Physiology, 285(5):C1339-47 (Nov. 2003).
Nagamoto, T., et al. "Alpha-smooth muscle actin expression in cultured lens epithelial cells." Invest Ophthalmol Vis Sci. Apr. 2000;41 (5): 1122-9.
NCBI, GenBank Accession No. NM_001419.2, "*Homo sapiens* ELAV like RNA binding protein 1 (ELAV1), mRNA", Mar. 15, 2015, 6 pages.
NCBI, GenBank Accession No. XM_011527777.1, "Predicted: *Homo sapiens* ELAV like RNA binding protein 1 (ELAV1), transcript variant X1, mRNA", Mar. 12, 2015, 4 pages.
Oehlke et al., "Cellular uptake of antisense oligonucleotides after complexing or conjugation with cell-penetrating model peptides", Eur. J. Biochem., 2002, vol. 269, pp. 4025-4032.
Oh et al, Subtractive proteomic mapping of the endothelial surface in lung and solid tumours for tissue-specific therapy, Nature 429(6992):629-35 (Jun. 2004).
Owens et al., "The Role of Smads in Skin Development", J. Invest. Dermatol., vol. 128, 2008, pp. 783-790.
Papadakis et al., Publication date: Mar. 1, 2004, "Promoters and control elements: designing expression cassettes for gene therapy.", Source: Current Gene Therapy, Mar. 1, 2004, Bentham Science Publishers Ltd., NL, Interregnum: ISSN 1566-5232, DOI: https://dx.doi.org/10.2174/1566523044578077, Source details: vol. 4, Nr.: 1, XP009159935, pp. 89-113.
Park et al., "Effect of siRNA with an Asymmetric RNA/dTdT Overhang on RNA Interference Activity", Nucleic Acid Therapeutics, 24(5): 364-371 (Oct. 2014).
Patil, Mahesh L. "Surface-Modified and Internally Cationic Polyamidoamine Dendrimers for Efficient siRNA Delivery", Bioconjugate Chem. vol. 19 Jun. 25, 2008, 1396-1403 (XP002617104).
Peng et al, "Nanoparticulate Delivery of Suicide DNA to Murine Prostate and ProstateTumors", The Prostate 67: 855-862, 2007.

Peng et al., Publication date: Oct. 1, 2011, "Epithelial cell-targeted transgene expression enables isolation of cyan fluorescent protein (CFP)-expressing prostate stem/progenitor cells", Source: Transgenic Research, Oct. 1, 2011, Springer Netherlands, NL, Interregnum: ISSN 0962-8819, DOI: https://dx.doi.org/10.1007/s11248-010-9478-2, Source details: vol. 20, Nr.: 5, XP055483317, pp. 1073-1086.
Piche-Nicholas etal., "Changes in complementarity-determining regions significantly alter IgG binding to the neonatal Fc receptor (FcRn) and pharmacokinetics", MABS 10(1): 81-94 (Year: 2018).
Poosarla et al, "Computational de novo design of antibodies binding to a peptide with high affinity", Biotech. & Bioengin. 114(6): 1331-1342, 2017.
Pye et al., "Dermal fibroblasts participate in the formation of new muscle fibres when implanted into regenerating normal mouse muscle", J. Anat., vol. 198, 2001, pp. 163-173.
Rendl et al., "Molecular Dissection of Mesenchymal-Epithelial Interactions in the Hair Follicle", PLOS Biol., vol. 3, 2005, pp. e331.
Rizzo et al, "Prostate epithelial stem cells", Cell Proliferation 38: 363-374, 2005.
Rogers et al., "Peptide conjugates for chromosomal gene targeting by triplex-forming oligonucleotides", Nucleic Acids Research, 2004, vol. 32(22), pp. 6595-6604.
Sampathkumar et al, "Dendrimers in Cancer Treatment and Diagnosis", Nanomaterials for Cancer Diagnosis 7: 43 pages, in Nanotechnologies for the Life Sciences, C. S. Kumar (Ed.), Wiley-VCH Verlag GmbH & Co. KGaA, 2007, DOI: 10.1002/9783527610419.ntls0071.
Sharov et al., "Bone Morphogenetic Protein Antagonist Noggin Promotes Skin Tumorigenesis via Stimulation of the Wnt and Shh Signaling Pathways", Am. J. Pathol., vol. 175, 2009, pp. 1303-1314.
Showalter et al, ""Nanoparticulate delivery of diphtheria toxin DNA effectively kills mesothelin expressing pancreatic cancer cells", Source: Cancer Biology & Therapy", Cancer Biol. & Therapy 7 ( 10) 2008: DOI: https://dx.doi.org/10.4161/cbt.7.10.6562; 1584-1590.
Singh et al, On the gene delivery efficacies of pH-sensitive cationic lipids via endosomal protonation: a chemical biology investigation, Chemistry & Biology, 11(5):713-23 (May 2004).
Sneddon et al., "Bone morphogenetic protein antagonist gremlin 1 is widely expressed by cancer-associated stromal cells and can promote tumor cell proliferation", Proc. Natl. Acad. Sci., vol. 103, 2006, pp. 14842-14847.
Stayton et al, 'Smart' delivery systems for biomolecular therapeutics, Orthodontics and Craniofacial Research, 8 (3):219-25 (Aug. 2005).
Stears et al., "A Novel, Sensitive Detection System for High-Density Microarrays Using Dendrimer Technology," Physiol. Genomics (2000) vol. 3, pp. 93-99.
Stetsenko et al., "Efficient Conjugation of Peptides to Oligonucleotides by 'Native Ligation", J. Org. Chem., 2000, vol. 65(16), pp. 4900-4908.
Suk et al, Gene delivery to differentiated neurotypic cells with RGD and HIV Tat peptide functionalized polymeric nanoparticles, Biomaterials, 27(29):5143-50 (Oct. 2006).
Tamaki et al. Identification of myogenic-endothelial progenitor cells in the interstitial spaces of skeletal muscle. J Cell Biol. May 13, 2002;157(4):571-7.
Tan et al., "Designer Tridentate Mucin 1 Aptamer for Targeted Drug Delivery," Journal of Pharmaceutical Sciences (May 1, 2012) vol. 101, No. 5, pp. 1672-1677.
Thawani et al., "Bone Morphogenetic Proteins and Cancer Review of the Literature", Neurosurgery, vol. 66, 2010, pp. 233-246.
Tong et al, "Identification of HPV-16 in Borderline Mucinous Cystic Neoplasm of Pancreas", Int. J. Biomed. Sci. 3(1): 72-75, 2007; abstract only.
Tung et al., "Preparation and Application of Peptide-Oligonucleotide Conjugates", Bioconjugate Chem., 2000, vol. 11 (5), pp. 605-618.

(56) References Cited

OTHER PUBLICATIONS

Varshosaz, Jaleh et al., "Nanoparticles for targeted delivery of therapeutics and small interfering RNAs in hepatocellular carcinoma", World Journal of Gastroenterology, vol. 21, No. 42, Jan. 1, 2015, 21 pages.
Walker, J., et al. "Unique precursors for the mesenchymal cells involved in injury response and fibrosis." Proc Natl Acad Sci US A. Aug. 3, 2010;107(31):13730-5. Epub Jul. 15, 2010.
Walker, J.L., et al. "Activation of SRC kinases signals induction of posterior capsule opacification." Invest Ophthalmol Vis Sci. May 2007;48(5):2214-23.
Wei et al., "A Bio-Abiotic Interface Constructed by Nanoscale DNA-Dendrimer and Conducting Polymer for Ultra- Sensitive Bio-Molecular Diagnosis," Small (2009) vol. 5, No. 15, pp. 1784-1790.
Wolff, I.M., et al. "Migration of Lens Epithelial Cells on the Posterior Lens Capsule is Blocked by Inhibition of Src Family Kinases." Invest Opthalmol Vis Sci. 2005;46:E-Abstract 2868.
Wormstone et al. Hepatocyte Growth Factor Function and c-Met Expression in Human Lens Epithelial Cells Invest Ophthalmol Vis Sci. 2000;41 :4216-4222.
Wormstone, I.M., et al. "Identification of Signalling Pathways Involved in TGFB2 Induced Matrix Contraction of Human Lens Cells." Investigative Opthalmology & Visual Science.May 1, 2005 ;46(8).
Wu et al., "Dendrimers as Carriers for siRNA Delivery and Gene Silencing: A Review", The Scientific World Journal, 2013, vol. 2013, Article ID 630654, pp. 1-16.
Xu et al., "Cell-penetrating peptide: a means of breaking through the physiological barriers of different tissues and organs", Journal of Controlled Release, 2019, vol. 309, pp. 106-124.
Yang et al., "Targeted Disruption of Smad4 in Mouse Epidermis Results in Failure of Hair Follicle Cycling and Formation of Skin Tumors", Cancer Res., vol. 65, 2005, pp. 8671-8678.
Yuen et al., "The prognostic significance of BMP-6 signaling in prostate cancer", (Modern Pathology, 2008, 21: 1436-1443).
Yuhki et al., "BMPR1A signaling is necessary for hair follicle cycling and hair shaft differentiation in mice", Development, vol. 131, 2004, pp. 1825-1833.
Zammit et al. The Skeletal Muscle Satellite Cell: The Stem Cell That Came in From the Cold. J Histochem Cytochem 2006 54: 1177-1190.
Zatsepin et al., "Conjugates of Oligonucleotides and Analogues with Cell Penetrating Peptides as Gene Silencing Agents", Current Pharmaceutical Design, 2005, vol. 11(28), pp. 3639-3654.
Zhang et al., "Bone Morphogenetic Protein Signaling Inhibits Hair Follicle Anagen Induction by Restricting Epithelial Stem/Progenitor Cell Activation and Expansion", Stem Cells, vol. 24, 2006, pp. 2826-2839.
Zhao et al, "DNA Origami Delivery System forCancer Therapy with TunableRelease Properties", ACS Nano 6(10): 8684-8691, Sep. 5, 2012.
Zhou, J., et al. "Inhibition of SRC Family Kinases Blocks Formation of Cortical Cataracts in Cultured Chick Embryo Lenses." Annual Meeting of the Association for Research in Vision and Opthamology. May 10, 2002; 2002.
Zhou, J., et al. "SRC Kinase Activation Induces Formation of Lens Opacities Through a Pathway." Annual Meeting of the Association for Research in Vision and Opthamology. May 8, 2003; 2003.
Zuhorn et al, Nonbilayer phase of lipoplex-membrane mixture determines endosomal escape of genetic cargo and transfection efficiency, Molecular Therapy, 11(5):801-10 (May 2005).

* cited by examiner

NUCLEIC ACID CARRIERS AND THERAPEUTIC METHODS OF USE

CROSS-REFERENCE TO RELATED APPLICATIONS

This application is a 35 U.S.C. § 371 national phase application of PCT Application No. PCT/US17/18323, filed Feb. 17, 2017, which claims priority to U.S. Provisional Application No. 62/297,194, filed Feb. 19, 2016, each of which is incorporated herein by reference in its entirety.

FIELD

The present disclosure is directed, in part, to nucleic acid carriers comprising targeting agents, pharmaceutical compositions comprising the same, and methods of making and using the same.

BACKGROUND

Multi-molecular scaffold devices, including DNA dendrimers, may be useful as cellular transfection, imaging, and drug delivery agents. DNA dendrimers may be bound with targeting devices (e.g., an antibody specific for a cell surface feature capable of eliciting an cellular endocytotic internalization event) and can bind to surface features on targeted cells to provide delivery of a cargo (e.g., a drug) intracellularly or extracellularly, respectively. Cargos may be passively associated with the targeted DNA dendrimer and enter the cell simply by spatial association with the dendrimer, or cargos may be directly bound to the dendrimer via a number of attachment strategies for release at the target destination.

It was previously found that DNA dendrimers could only be successfully made from DNA produced by "natural" means, such as DNA produced via the use of biological systems (e.g., bacterial cloning) or via the use of enzymatic polymerization of DNA sequences (as from the polymerase chain reaction (PCR) and other enzymatically dependent DNA synthesis methods). However, it is not economically feasible to produce DNA dendrimers in the quantities necessary for commercial applications such as therapeutic drug delivery applications when they are assembled from naturally produced DNA. In particular, biological replication of the sequences required for construction of a DNA dendrimer produces double-stranded molecules from which the single-strands required for construction of the dendrimer must be separated and isolated. Although chemical synthesis methods are capable of providing the quantities required for these applications, prior attempts at using synthetically manufactured DNA oligonucleotides repeatedly failed to successfully form covalent structures after cross-linking procedures described in the prior art were applied, suggesting that prior art oligonucleotide design parameters were inappropriate for chemically synthesized oligonucleotides. This disclosure presents, among other things, new compositions of matter and production methods for the use of chemically synthesized DNA as the raw materials for the production of nucleic acid carriers, which are particularly well suited for large scale synthesis.

SUMMARY

The present disclosure provides monomeric nucleic acid carriers comprising: a first and a second oligonucleotide; wherein a central portion of each of the first and second oligonucleotides is complementary to each other, forming a double-stranded region, wherein the two terminal portions of the first oligonucleotide are not complementary to the two terminal portions of the second oligonucleotide, forming four single-stranded arms; and at least one targeting agent conjugated to at least one single-stranded arm.

The present disclosure also provides double monomer nucleic acid carriers comprising a first monomeric nucleic acid carrier and a second monomeric nucleic acid carrier, wherein one single-stranded arm of the first monomeric nucleic acid carrier is conjugated to one single-stranded arm of the second monomeric nucleic acid carrier, forming a double monomer nucleic acid carrier comprising six peripheral single-stranded arms.

The present disclosure also provides trimer nucleic acid carriers comprising: a first oligonucleotide having a central portion, a first terminal arm, and a second terminal arm; a second oligonucleotide having a central portion, a first terminal arm, and a second terminal arm, wherein the first terminal arm of the second oligonucleotide is complementary to the first terminal arm of the first oligonucleotide and hybridized thereto; and a third oligonucleotide having a central portion, a first terminal arm, and a second terminal arm, wherein the first terminal arm of the third oligonucleotide is complementary to the second terminal arm of the first oligonucleotide and hybridized thereto; wherein the second terminal arm of the second oligonucleotide is conjugated to a first targeting agent, and the second terminal arm of the third oligonucleotide is conjugated to a second targeting agent.

The present disclosure also provides nucleic acid carriers comprising: a central portion, a first terminal arm, and a second terminal arm; wherein the first terminal arm is conjugated to a first targeting agent, and the second terminal is conjugated to a second targeting agent.

The present disclosure also provides pharmaceutical compositions comprising any of the nucleic acid carriers described herein, and a pharmaceutically acceptable vehicle.

The present disclosure also provides methods of making the monomeric nucleic acid carrier comprising: hybridizing the first oligonucleotide to the second oligonucleotide; and conjugating the at least one targeting agent to the at least one single-stranded arm.

The present disclosure also provides methods of making the double monomer nucleic acid carriers comprising: hybridizing the first oligonucleotide to the second oligonucleotide to form a first nucleic acid carrier; hybridizing the third oligonucleotide to the fourth oligonucleotide to form a second nucleic acid carrier; hybridizing one single-stranded arm of the first nucleic acid carrier to one single-stranded arm of the second nucleic acid carrier, forming a double monomer nucleic acid carrier comprising six single-stranded arms; and conjugating the at least one targeting agent to the at least one single-stranded arm.

The present disclosure also provides methods of making the trimer nucleic acid carriers comprising: hybridizing the first terminal arm of the second oligonucleotide to the first terminal arm of the first oligonucleotide; hybridizing the first terminal arm of the third oligonucleotide to the second terminal arm of the first oligonucleotide; conjugating the first targeting agent to the second terminal arm of the second oligonucleotide; and conjugating the second targeting agent to the second terminal arm of the third oligonucleotide.

The present disclosure also provides methods of making nucleic acid carriers comprising: conjugating the first targeting agent to the first terminal arm; and conjugating the second targeting agent to the second terminal arm.

The present disclosure also provides methods of inducing an immune response in an animal comprising administering to the animal any of the nucleic acid carriers described herein, or a pharmaceutical composition comprising the same, wherein the nucleic acid carrier comprises at least two targeting agents chosen from an antigen, a peptide, an antibody or fragment thereof, and an adjuvant.

The present disclosure also provides methods of treating an animal having cancer comprising administering to the animal any of the nucleic acid carriers described herein, or a pharmaceutical composition comprising the same, wherein the nucleic acid carrier comprises at least two targeting agents chosen from an antibody, or fragment thereof, and a label.

The present disclosure also provides methods of treating an animal having a disease associated with a disease-associated antigen comprising administering to the animal any of the nucleic acid carriers described herein, or a pharmaceutical composition comprising the same, wherein the nucleic acid carrier comprises at least two targeting agents chosen from an antibody, or fragment thereof, and a label.

DESCRIPTION OF EMBODIMENTS

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

Figure 1:
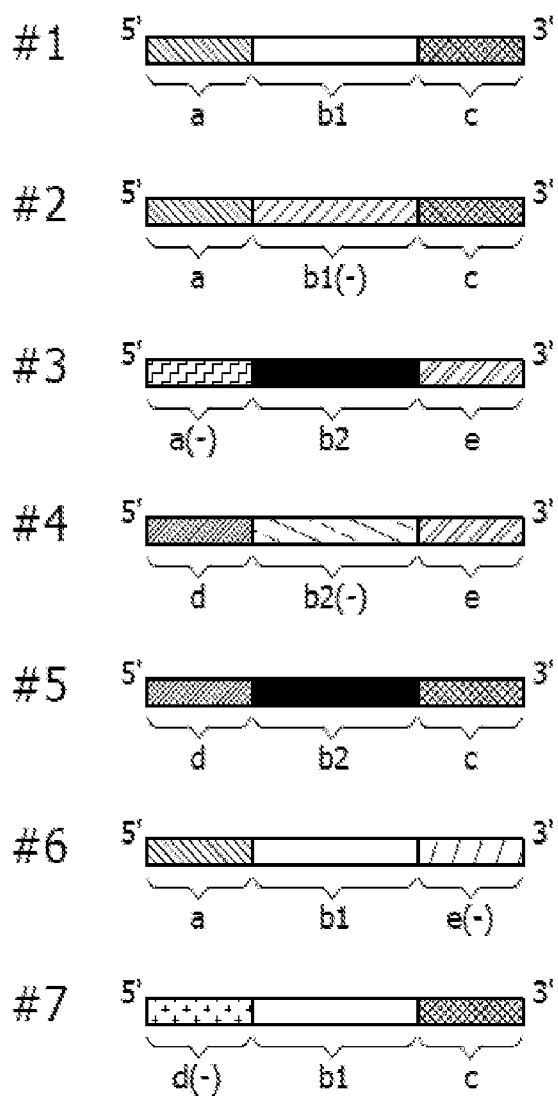
FIG. 1 shows representative first and second oligonucleotides (e.g., #1, #2, #3, #4, #5, #6, and #7) that form a nucleic acid carrier monomer (e.g., A, B', B", C', and C") when hybridized; the oligonucleotides comprise a central core portion (e.g., "b1", "b1(−)", "b2", "b2(−1)", and "b1") that hybridize to form a double-stranded region; the oligonucleotides also comprise two terminal portions (e.g., "a", "c", "a(−)", "e", "d" "e(−)", and "d(−)") that form four single-stranded arms when the two oligonucleotides are hybridized to form the monomer.
Figure 1:
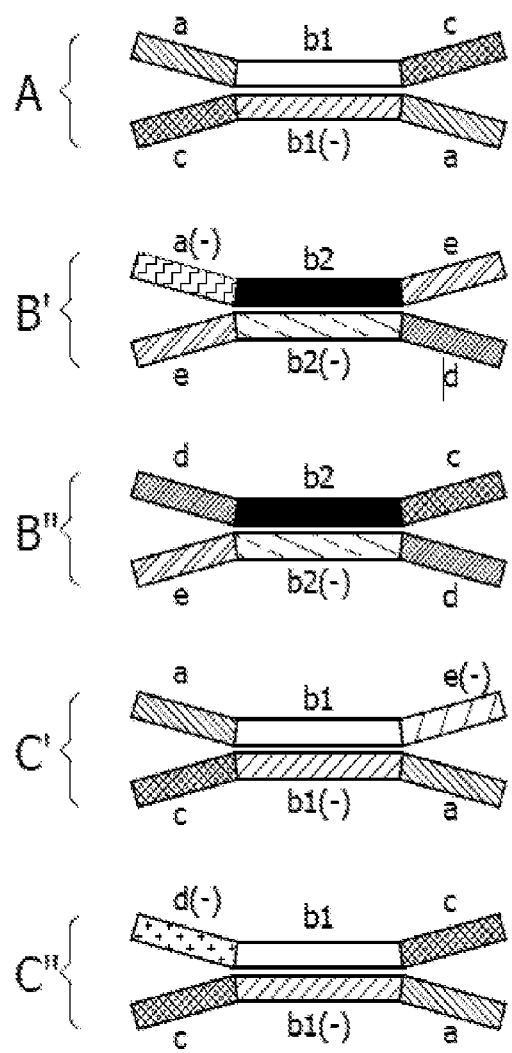
Figure 2A:
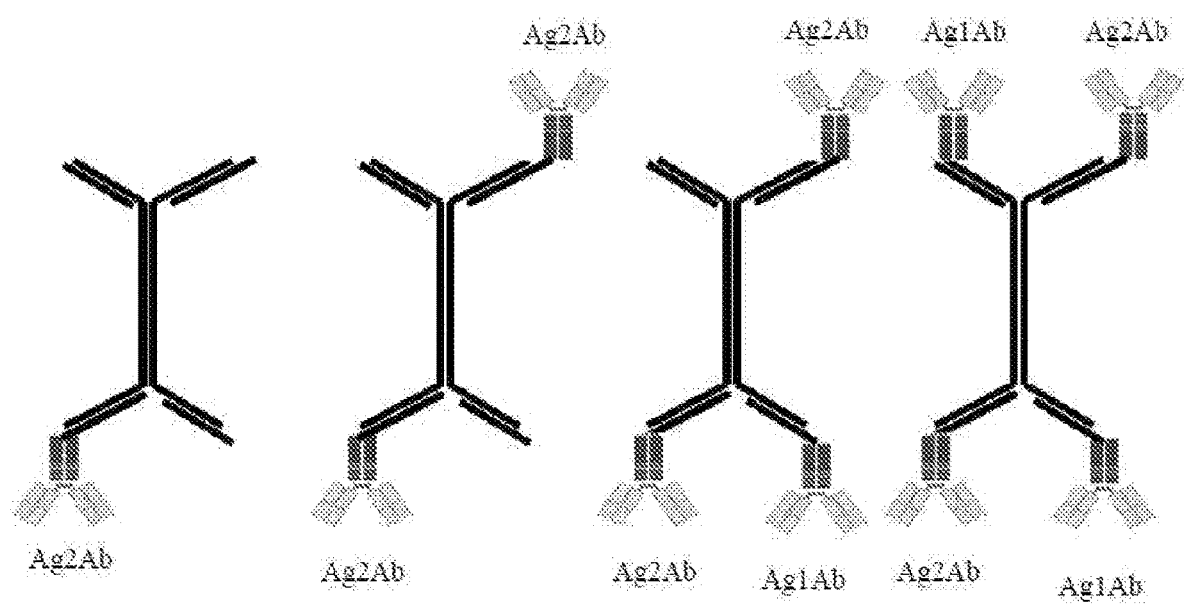
FIGS. 2A, 2B, 2C, 2D, and 2E show representative nucleic acid carrier monomers with 1, 2, 3 or 4 targeting agents (e.g., antibodies Ag1Ab, Ag2Ab, Ag3Ab, and Ag4Ab) per monomer; also shown are optional oligonucleotides (which are not conjugated to any antibodies) bound to single-stranded arms and forming double-stranded DNA structures.
Figure 2B:
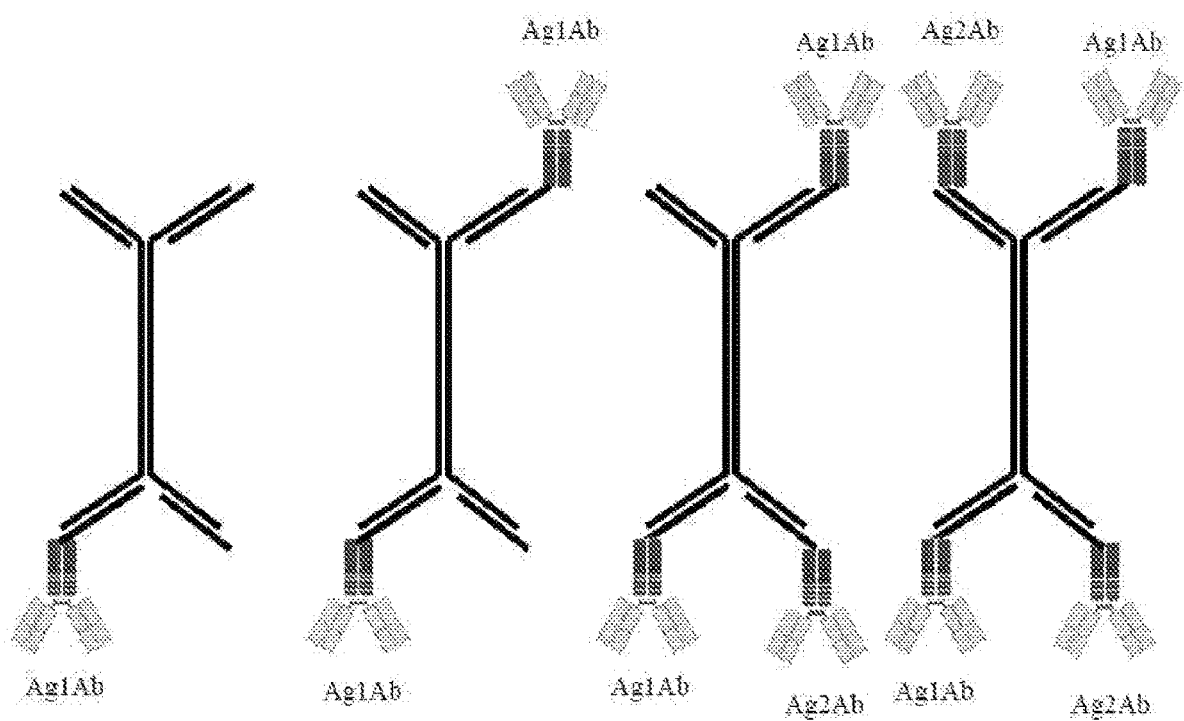
Figure 2C:
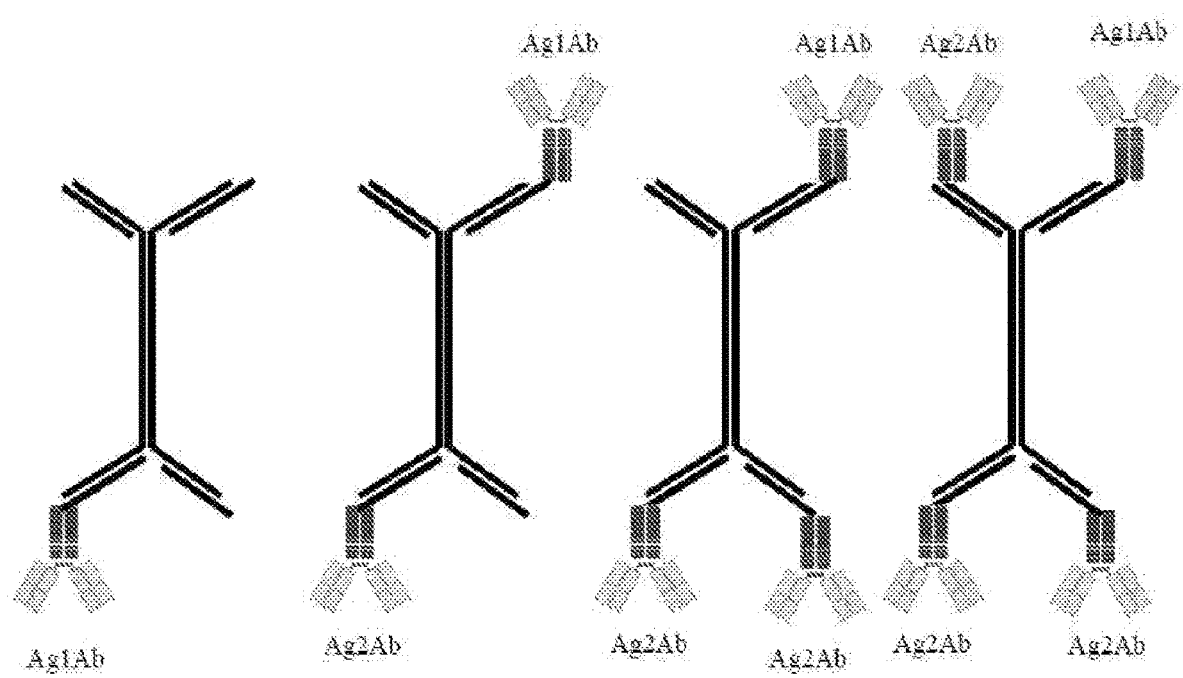
Figure 2D:
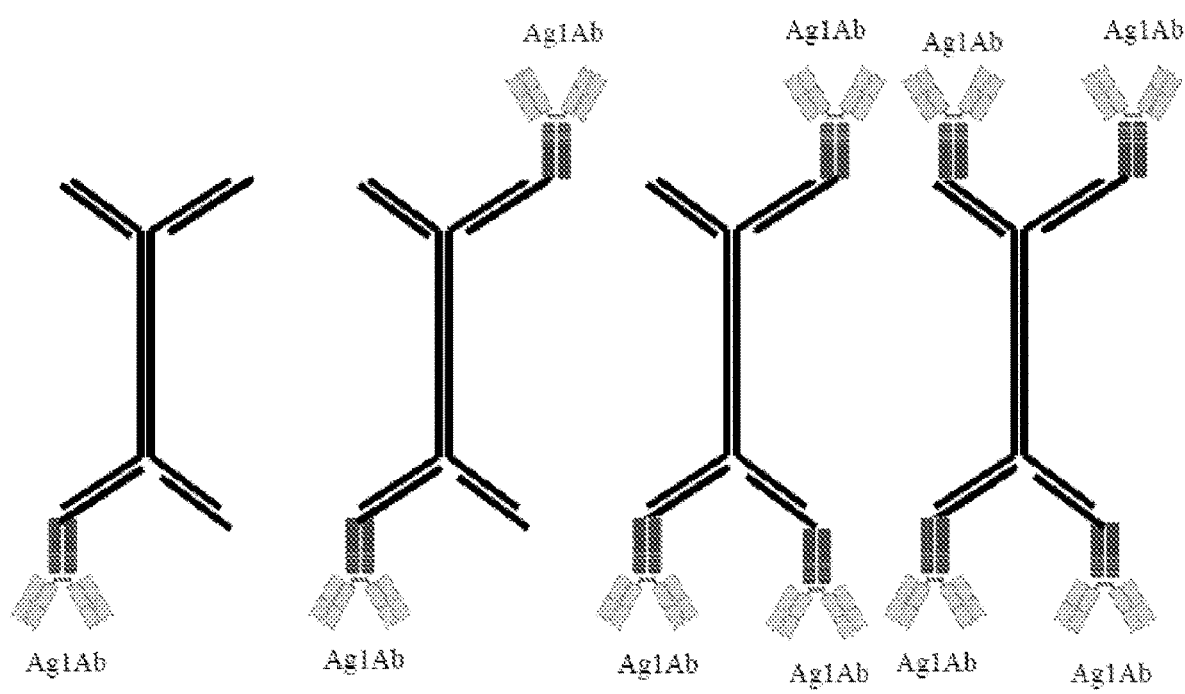
Figure 2E:
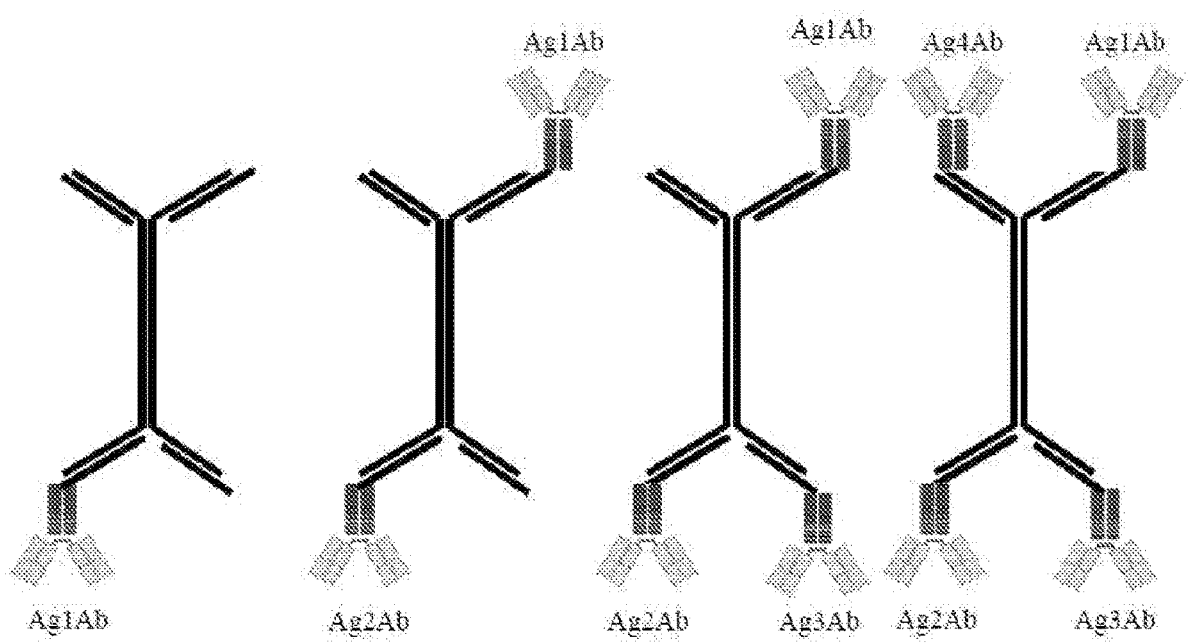

The present disclosure provides monomeric nucleic acid carriers comprising a core unit that comprises a first oligonucleotide and a second oligonucleotide. A central portion of each of the first and second oligonucleotides is complementary to each other, thus forming a double-stranded region. The two terminal portions of the first oligonucleotide are not complementary to the two terminal portions of the second oligonucleotide, thus forming four single-stranded arms. FIG. 1 shows representative first and second oligonucleotides (see, #1, #2, #3, #4, #5, #6, and #7 oligonucleotides) that form a nucleic acid carrier monomer (see, A, B', B", C', and C" monomers) when hybridized. Each oligonucleotide comprises a central core portion (see, "b1", "b1(−)", "b2", "b2(−1)", and "b1") that hybridizes with another oligonucleotide having a central core portion to form a double-stranded region. Each oligonucleotide also comprise two terminal portions (see, "a", "c", "a(−)", "e", "d" "e(−)", and "d(−)") that form four single-stranded arms when the two oligonucleotides are hybridized to form the monomer. In some embodiments, each terminal portion (i.e., the four terminal portions of a hybridized pair of oligonucleotides) comprises a unique nucleotide sequence.

In some embodiments, the oligonucleotide is 97 nucleotides in length. The 97-mer has some advantages because it is short enough for efficient synthesis and does not need to be gel-purified, but is still sufficiently large that hybridization is efficient. Suitable nucleotide sequences comprise little or no secondary structure such as hairpins, have a $T_m$ greater than 50° C.-55° C. (suitably 65° C.-75° C.), at least one cross-linking site, and a central hybridization region and 3-prime and 5-prime arm regions of no less than 25 bases in length unless modified nucleotides, comprising locked nucleic acids or similar nucleotides, are used to further increase the $T_m$.

The nucleic acid comprising the oligonucleotides may be any type of nucleic acid or nucleic acid derivative that is amenable to chemical synthesis methods known in the art, or to chemical synthesis methods with subsequent derivatization. Suitable nucleic acids include, but are not limited to, deoxyribonucleic acid (DNA), ribonucleic acid (RNA), modified DNA or RNA, peptide nucleic acid (PNA), morpholino and locked nucleic acid (LNA), glycol nucleic acid (GNA), threose nucleic acid (TNA), DNA containing phosphorothioate residues (S-oligos) and derivatives thereof, or any combination thereof.

In some embodiments, the nucleic acid carrier may contain oligonucleotides that comprise different nucleotide backbones. In some embodiments, in a nucleic acid carrier having two layers as described herein, the oligonucleotides making up the first inner layer may comprise a particular nucleotide backbone, whereas the oligonucleotides making up the second more outer layer may comprise a different particular nucleotide backbone. The same can be present in multiple layer nucleic acid carriers, with one or more of the layers having oligonucleotides with a different nucleotide backbone compared to an adjacent layer. For example, in some embodiments, a nucleic acid carrier can contain both phosphodiester (PO) synthetic oligonucleotide strands and phosphorothioate (PS) oligonucleotide strands. In some embodiments, the first inner layer is all PO-DNA and the oligonucleotide strands added to make the second more outer layer are PS-DNA. In some embodiments, using modified nucleotide bases can alter the serum degradation profile and the resulting clearance profile, indicating that the PK/PD profile of the carrier may be subsequently altered as well.

In some embodiments, the nucleic acid comprising the oligonucleotides is a nucleoside analog which increases the $T_m$ of the molecule as compared to conventional nucleosides, For example Locked Nucleic Acids (LNA™) nucleosides may be used in which the ribose ring is modified with a methylene bridge between the 2'-O atom and the 4'-C atom. When the oligonucleotides comprise one or more $T_m$-increasing nucleotides, the overall length may be reduced compared to those consisting of all naturally occurring nucleotides without compromising hybridization efficiency. Generally, the length and composition of naturally-occurring and $T_m$-increasing nucleotides in the oligonucleotides can be selected such that the $T_m$ of the segment is greater, or at least 5° C. greater or at least 10° C. greater, than the temperature at which the nucleic acid will be used. For example, a nucleic acid strand comprising 31 conventional DNA residues has the same $T_m$ as a 19 nucleotide strand comprising 50% LNA residues (66° C. $T_m$ for both). That is, if the segment comprises 50% LNA, the $T_m$ will be increased approximately 1.5-fold and the overall length of the oligonucleotide may therefore be approximately halved without compromising the efficiency of hybridization of the segment to its complementary nucleic acid molecule. In some embodiments, oligonucleotides as described herein that comprise $T_m$-increasing nucleotides in segments that will be used for hybridization may be from 40 to 50 nucleotides in total length, with the double-stranded region and the single-stranded arms each independently from 12 to 18 nucleotides in length. In addition, the nucleic acid may have alternate backbones, such as a phosphoramidite backbone.

In some embodiments, the oligonucleotides comprise one or more adjacent thymidine-adenine (TpA-5' to 3' orientation) residues. A TpA site improves crosslinking of the oligonucleotide molecules when they are assembled in the branched nucleic acid carriers and psoralen or psoralen-like molecules are used as inducible cross-linking agents. TpA residues may be present in any or all of the single-stranded arms or the double-stranded region. In some embodiments, the oligonucleotides comprise from about 3 to about 7 TpA sites. In some embodiments, both of the single-stranded arms and the double-stranded region comprise at least 3 TpA residues. In some embodiments, one or more of the single-stranded arms and the double-stranded region may comprise from about 3 to about 7 TpA sites, such as 3, 4, 5, 6, or 7 TpA sites. In some embodiments, the single-stranded arms comprise from about 3 to about 7 TpA sites, or from about 3 to about 4 TpA sites. In some embodiments, the double-stranded region comprises from about 5 to about 6 TpA sites. TpA sites may also be replaced with other cross-linking sites and combined with that corresponding and most suitable cross-linking agent. For example, mitomycin C forms intrastrand cross-links at GpG, and CpG sites and may also be used as an effective alternative or additional site for cross-linking of the DNA scaffold.

It is generally desirable to select nucleotide sequences for the oligonucleotides that minimize or eliminate secondary structure capable of self-hybridizing or self-binding via Watson-Crick base pairing under physiologic conditions, and to select a suitable hybridization melting temperature ($T_m$) of the single-strands in monomers and of the monomers in the branched nucleic acid carriers. Typically, a $T_m$ of about 65 to 75° C. is desired, or at least 10-15° C. above the temperature at which the materials will be utilized.

The double-stranded region formed by the complementarity between the first and second oligonucleotides is from about 4 to about 2000 bases in length, from about 5 to about 200 bases in length, from about 25 to about 50 bases in length, or from about 25 to about 35 bases in length. In some embodiments, the double-stranded region is 31 bases in length.

Each single-stranded arm is from about 4 to about 200 bases in length, from about 5 to about 50 bases in length, from about 25 to about 50 bases in length, from about 25 to about 35 bases in length, from about 16 to about 50 bases in length, or from about 12 to about 18 bases in length. In some embodiments, the single-stranded arm is 31 bases in length.

In some embodiments, the oligonucleotides may comprise one or two hinge segments joining one or both of the single-stranded arms to the double-stranded region. Each hinge segment may be from 1 to 4 nucleotides in length, from 2 to 4 nucleotides in length, 1 nucleotide in length, 2 nucleotides in length, 3 nucleotides in length, or 4 nucleotides in length. In some embodiments, the nucleotide sequence of the hinge segment 5' to the double-stranded region is CA, and the nucleotide sequence of the hinge segment 3' to the double-stranded region is AC.

Each of the single-stranded arms has a nucleic acid sequence that can be the same as or different from any other single-stranded arm. In some embodiments, the nucleotide sequence of each of the four single-stranded arms is identical. In some embodiments, the nucleotide sequences of three of the four single-stranded arms are identical to each other and different than the nucleotide sequence of the fourth single-stranded arm. In some embodiments, the nucleotide sequences of two of the four single-stranded arms are identical to each other and different than the nucleotide sequences of the other two single-stranded arms. In some embodiments, the nucleotide sequences of two of the four single-stranded arms are identical to each other and the nucleotide sequences of the other two of the four single-stranded arms are identical to each other, wherein the nucleotide sequence of the first two single-stranded arms is different than the nucleotide sequences of the second two single-stranded arms. In some embodiments, the nucleotide sequence of each of the four single-stranded arms is different. Thus, the nucleotide sequence of any particular single-stranded arm provides flexibility in design choice and can be used to specifically bind to or be conjugated to a particular linking oligonucleotide (which may or may not be further conjugated to a targeting agent) or to another single-stranded arm of another monomeric nucleic acid carrier.

In some embodiments, at least one targeting agent is conjugated to at least one single-stranded arm. In some embodiments, a single targeting agent is conjugated to one single-stranded arm. In some embodiments, two targeting agents are conjugated to two different single-stranded arms.

In some embodiments, three targeting agents are conjugated to three different single-stranded arms. In some embodiments, four targeting agents are conjugated to four different single-stranded arms.

In some embodiments, a single targeting agent is conjugated to a single-stranded arm. In some embodiments, a first targeting agent is conjugated to one single-stranded arm and a second targeting agent is conjugated to a different single-stranded arm. In some embodiments, the first targeting agent is identical to the second targeting agent. In some embodiments, the first targeting agent is different than the second targeting agent.

In some embodiments, a first targeting agent is conjugated to one single-stranded arm, a second targeting agent is conjugated to a different single-stranded arm, and a third targeting agent is conjugated to a different single-stranded arm. In some embodiments, the first targeting agent, the second targeting agent, and the third targeting agent are identical. In some embodiments, the first and second targeting agents are identical and the third targeting agent is different than the first and second targeting agents. In some embodiments, the first targeting agent, the second targeting agent, and the third targeting agent are different.

In some embodiments, a first targeting agent is conjugated to one single-stranded arm, a second targeting agent is conjugated to a different single-stranded arm, a third targeting agent is conjugated to a different single-stranded arm, and a fourth targeting agent is conjugated to a different single-stranded arm. In some embodiments, the first targeting agent, the second targeting agent, the third targeting agent, and the fourth targeting agent are identical. In some embodiments, the first targeting agent, the second targeting agent, and the third targeting agent are identical and the fourth targeting agent is different. In some embodiments, the first targeting agent and the second targeting agent are identical, and the third targeting agent and the fourth targeting agent are identical, wherein the first and second targeting agents are different than the third and fourth targeting agents. In some embodiments, the first targeting agent and the second targeting agent are identical, and the third targeting agent and the fourth targeting agent are each different. In some embodiments, the first targeting agent, the second targeting agent, the third targeting agent, and the fourth targeting agent are each different.

FIGS. 2A, 2B, 2C, 2D, and 2E show representative nucleic acid carrier monomers with 1, 2, 3 or 4 targeting agents (see, antibodies Ag1Ab, Ag2Ab, Ag3Ab, and Ag4Ab) per monomer. Also shown are optional oligonucleotides (which are not conjugated to any antibodies) bound to single-stranded arms and forming double-stranded DNA structures. The double-stranded region formed by the hybridization of the optional oligonucleotide to a single-stranded arm can be blunt-ended, or either the optional oligonucleotide or the single-stranded arm can have a 1 to 5 nucleotide base overhang.

The present disclosure also provides double monomer nucleic acid carriers comprising a first monomeric nucleic acid carrier as described herein and a second monomeric nucleic acid carrier as described herein. In some embodiments, an unhybridized, single-stranded arm of the first monomer may be available for hybridization to an unhybridized, single-stranded arm of the second monomer to produce the double monomer nucleic acid carrier described herein. In such embodiments, the arms of the monomers are selected such that they are complementary to unhybridized single-stranded arms of further monomers. The unhybridized, single-stranded arms of the monomers are therefore available for hybridization to the unhybridized, single-stranded arms of further monomers to produce a branched nucleic acid carrier or nucleic acid-based matrix. Accordingly, the nucleotide sequence of the single-stranded arms which flank the double-stranded region may be varied as desired to construct different branched nucleic acid carriers via hybridization of the single-stranded arms of one monomer to another monomer. Generally, relatively few double-stranded regions are necessary for constructing the branched nucleic acid carriers, because many different single-stranded arms may be linked to them to define and direct construction of the branched nucleic acid carriers. The nucleotide sequence of a single-stranded arm may be designed such that it is complementary to the nucleotide sequence of a single-stranded arm on another monomer, thus providing the ability to link to monomers by their single-stranded arm. Alternately, a conjugation oligonucleotide may be used to link to monomers by their single-stranded arms, wherein a portion of the conjugation oligonucleotide is complementary to a portion of the single-stranded arm on one monomer and is also complementary to a portion of the single-stranded arm on a second monomer. Thus, the conjugation oligonucleotide joins one monomer to another monomer. Conjugation of one single-stranded arm of the first monomeric nucleic acid carrier to one single-stranded arm of the second monomeric nucleic acid carrier forms a double monomer nucleic acid carrier comprising six peripheral single-stranded arms.

The double monomer nucleic acid carrier can comprise the types of nucleic acid described above for the monomeric nucleic acid carriers. The double monomer nucleic acid carrier can comprise the lengths and content of the double-stranded regions and the lengths and content of the single-stranded arms described above for the monomeric nucleic acid carriers.

In some embodiments, the nucleotide sequence of each of the six peripheral single-stranded arms is identical. In some embodiments, the nucleotide sequence of at least one, at least two, at least three, at least four, or at least five of the peripheral single-stranded arms are different than the nucleotide sequence of the other peripheral single-stranded arms. The nucleotide sequence of any particular peripheral single-stranded arm can also be identical to any one or more of the nucleotide sequences of the other peripheral single-stranded arms. Any combination of nucleotide sequences of the peripheral single-stranded arms is possible. For example, there may be three sets of two nucleotide identical nucleotide sequences within the six peripheral single-stranded arms. In another example, there may be two sets of three identical nucleotide sequences within the six peripheral single-stranded arms. In another example, there may be one set of four identical nucleotide sequences and one set of two identical nucleotide sequences within the six peripheral single-stranded arms. These examples are not meant to be limiting in any manner.

In some embodiments, at least one targeting agent, at least two targeting agents, at least three targeting agents, at least four targeting agents, at least five targeting agents, or six targeting agents are conjugated to the peripheral single-stranded arms. In some embodiments, all targeting agents are identical, or at least one targeting agent, at least two targeting agents, at least three targeting agents, at least four targeting agents, or at least five targeting agents, are different from one another. In some embodiments, one or more peripheral single-stranded arms not conjugated to a targeting agent is complementary base paired to an oligonucleotide linker. The double-stranded region formed by the hybridization of the oligonucleotide linker to a single-stranded arm can be blunt-ended, or either the oligonucleotide linker or the single-stranded arm can have a 1 to 5 nucleotide base overhang.

Figure 3A:
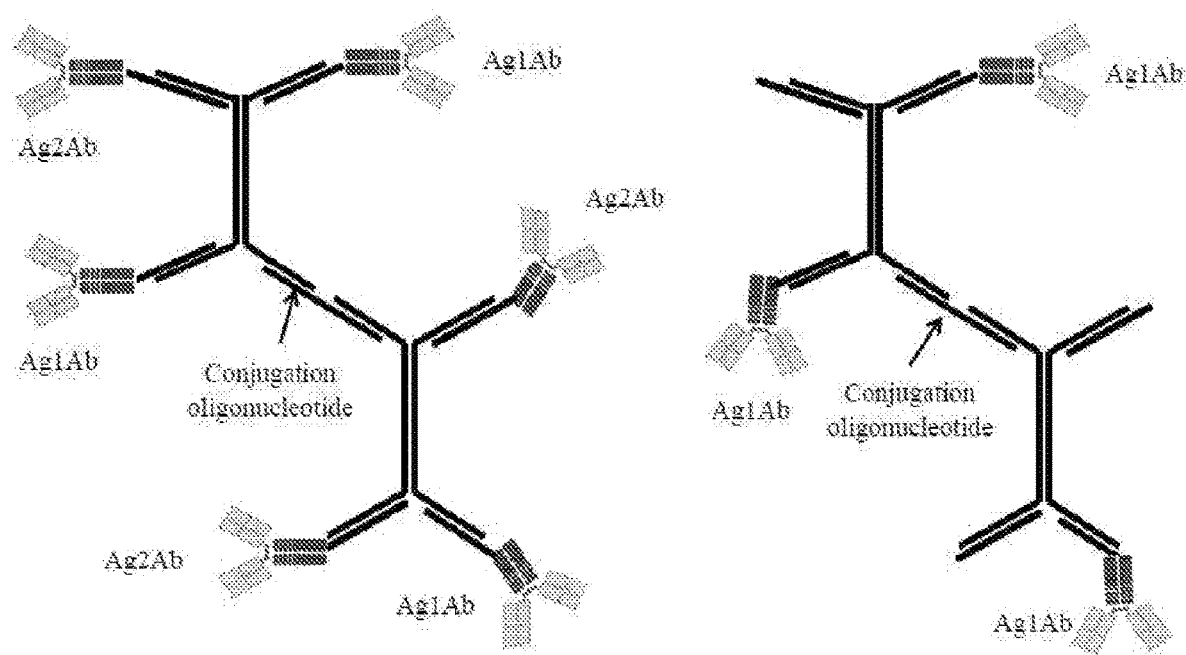
FIGS. 3A, 3B, and 3C show representative double monomer nucleic acid carriers comprising two monomers bound to one another via a conjugation oligonucleotide; these double monomer nucleic acid carriers have six single-stranded arms capable of conjugating to any of the targeting agents described herein.
Figure 3B:
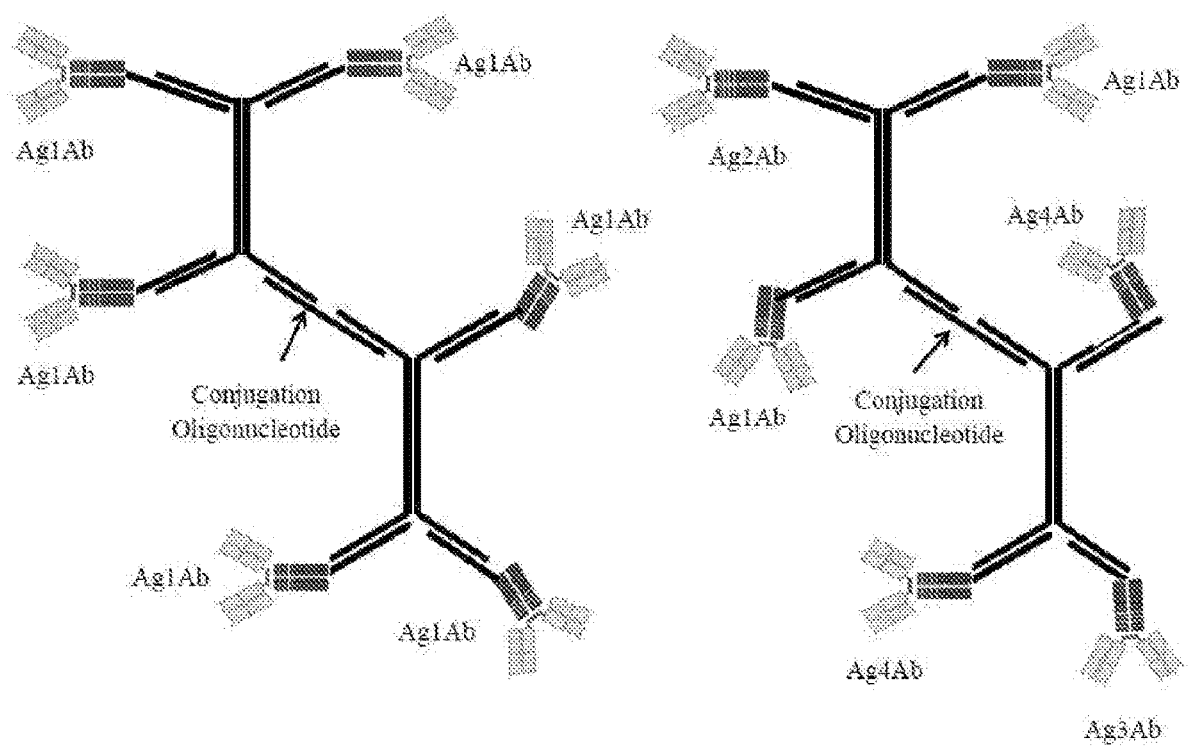
Figure 3C:
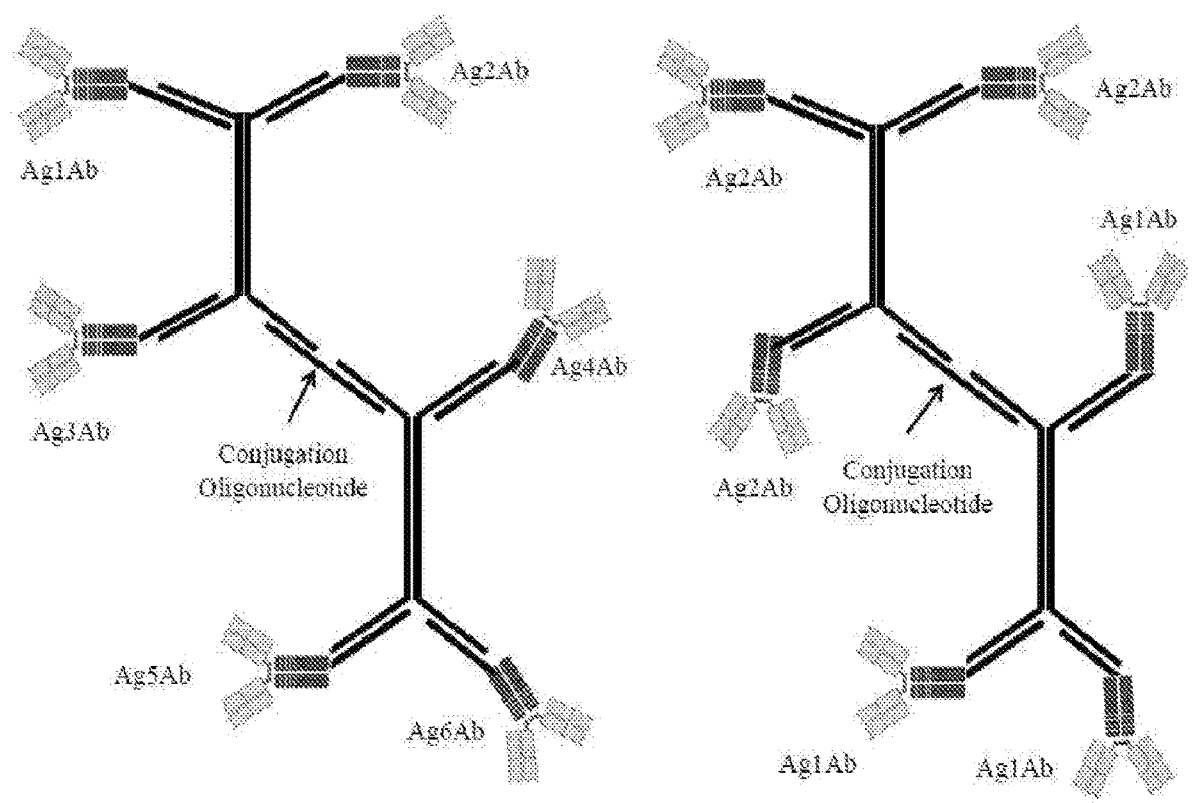

FIGS. 3A, 3B, and 3C show representative double monomer nucleic acid carriers comprising two monomers bound to one another via a conjugation oligonucleotide. These double monomer nucleic acid carriers have six single-stranded arms capable of conjugating to any of the targeting agents described herein.

The present disclosure also provides trimer nucleic acid carriers comprising a first oligonucleotide having a central portion, a first terminal arm, and a second terminal arm; a second oligonucleotide having a central portion, a first terminal arm, and a second terminal arm, wherein the first terminal arm of the second oligonucleotide is complementary to the first terminal arm of the first oligonucleotide and hybridized thereto; and a third oligonucleotide having a central portion, a first terminal arm, and a second terminal arm, wherein the first terminal arm of the third oligonucleotide is complementary to the second terminal arm of the first oligonucleotide and hybridized thereto; and wherein the second terminal arm of the second oligonucleotide is conjugated to a first targeting agent, and the second terminal arm of the third oligonucleotide is conjugated to a second targeting agent.

The trimer nucleic acid carrier can comprise the types of nucleic acid described above for the monomeric nucleic acid carriers. The trimer nucleic acid carrier can comprise the lengths and content of the double-stranded regions and the lengths and content of the single-stranded arms described above for the monomeric nucleic acid carriers.

In some embodiments, the nucleotide sequences of the two terminal arms available for conjugation to a targeting agent are identical. In some embodiments, the nucleotide sequence of one of the terminal arms available for conjugation to a targeting agent is different than the nucleotide sequence of the second terminal arm available for conjugation to a targeting agent.

In some embodiments, the first targeting agent is identical to the second targeting agent. In some embodiments, the first targeting agent is different than the second targeting agent.

Figure 4:
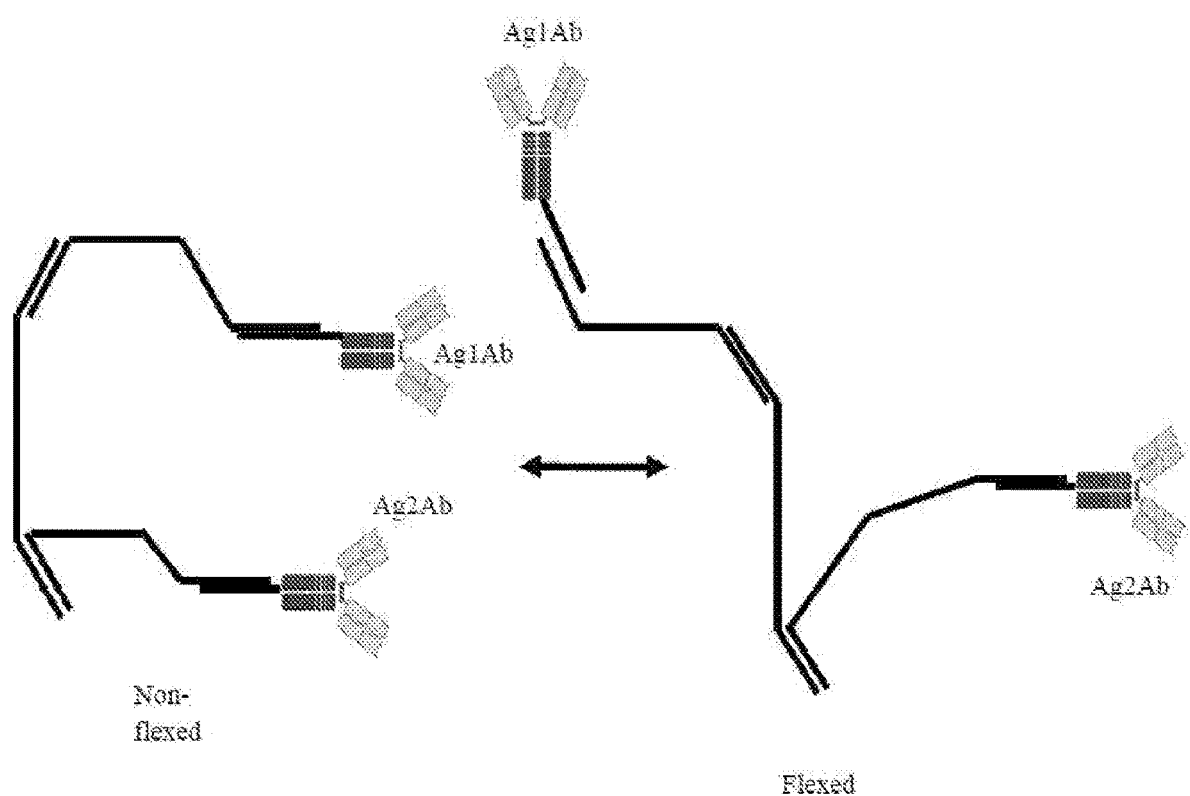
FIG. 4 shows representative trimer nucleic acid carriers comprising three oligonucleotides configured to provide two single-stranded arms capable of conjugating to any of the targeting agents described herein.

FIG. 4 shows representative trimer nucleic acid carriers comprising three oligonucleotides configured to provide two single-stranded arms capable of conjugating to any of the targeting agents described herein.

The present disclosure also provides another nucleic acid carrier comprising a central portion, a first terminal arm, and a second terminal arm, wherein the first terminal arm is conjugated to a first targeting agent, and the second terminal is conjugated to a second targeting agent. In some embodiments, the central portion, the first terminal arm, and the second terminal arm are single-stranded DNA. In some embodiments, the central portion, the first terminal arm, and the second terminal arm are double-stranded DNA.

The nucleic acid carrier can comprise the types of nucleic acid described above for the monomeric nucleic acid carriers. The nucleic acid carrier can comprise the lengths and content of the double-stranded regions and the lengths and content of the single-stranded arms described above for the monomeric nucleic acid carriers.

In some embodiments, the nucleotide sequences of the two terminal arms are identical. In some embodiments, the nucleotide sequences of the two terminal arms are different.

In some embodiments, the first targeting agent is identical to the second targeting agent. In some embodiments, the first targeting agent is different than the second targeting agent.

In some embodiments, the first and/or second targeting agents are conjugated to its peripheral single-stranded arm by an oligonucleotide linker as described herein for the monomeric nucleic acid carriers.

Figure 5:
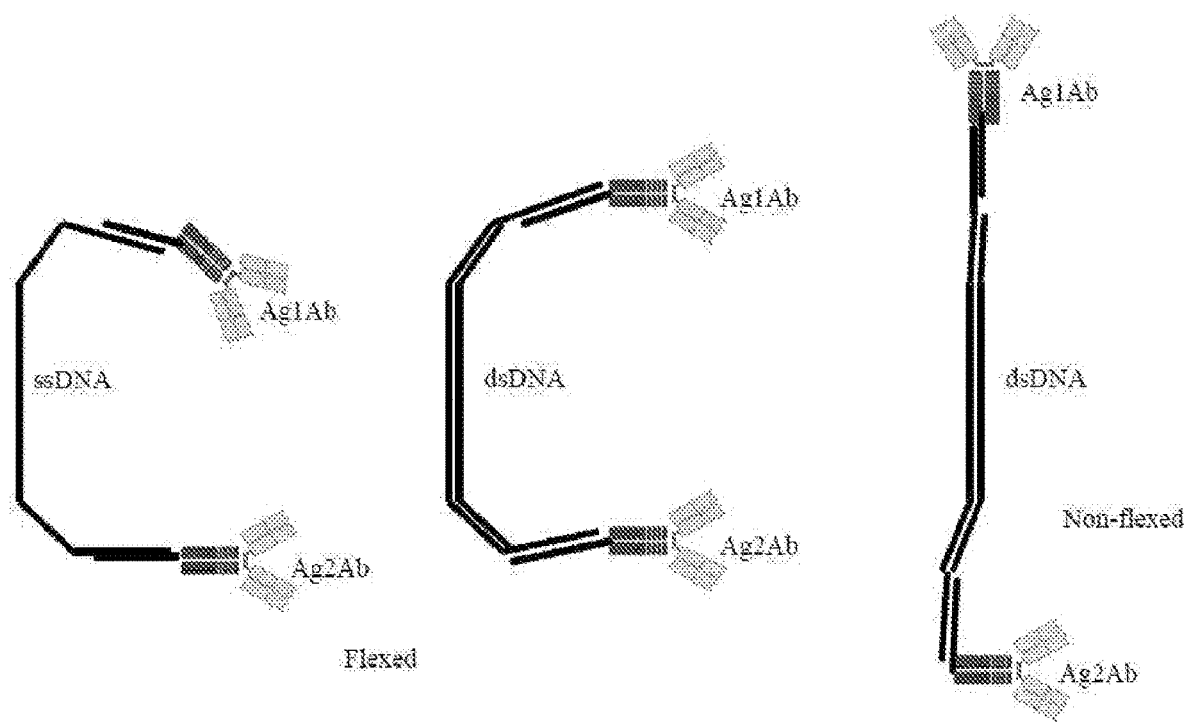
FIG. 5 shows representative ssDNA or dsDNA oligonucleotides configured to provide two single-stranded arms capable of conjugating to any of the targeting agents described herein.

FIG. 5 shows representative ssDNA or dsDNA oligonucleotides configured to provide two single-stranded arms capable of conjugating to any of the targeting agents described herein.

In any embodiment whereby a targeting agent is conjugated to a single-stranded arm or terminal arm, such conjugation may be carried out via an oligonucleotide linker that is linked to the targeting agent, and wherein a portion of the oligonucleotide linker is complementary to a portion of the nucleotide sequence of the single-stranded arm or terminal arm. Thus, the targeting agent is conjugated to the single-stranded arm or terminal arm by an oligonucleotide linker. In some embodiments, one or more single-stranded arms or terminal arms that are not conjugated to a targeting agent are complementary base paired to an oligonucleotide linker that is not conjugated to a targeting agent. In any of these embodiments where a single-stranded arm or terminal arm is complementary to a portion of the oligonucleotide linker, it is not necessary that the entire portion of the single-stranded arm or terminal arm or the oligonucleotide linker be complementary thereto. Thus, for example, if a particular single-stranded arm or terminal arm comprises 31 nucleotides, the oligonucleotide linker (with or without a conjugated targeting agent) need not be complementary to all 31 nucleotides. Rather, the oligonucleotide linker must be sufficiently complementary to the particular single-stranded arm or terminal arm to result in hybridization.

In some embodiments, that targeting agent may be conjugated to the nucleic acid carrier via the single-stranded arm or terminal arm by chemical modifications of the same which are incorporated into the single-stranded nucleic acid molecules during or after their synthesis. Such modification may include, for example, nucleoside amidites chemically modified with amine on a carbon chain linker.

In some embodiments, conjugation of a targeting agent to the nucleic acid carrier may be via the unhybridized, single-stranded arms or terminal arms, such as by linkage to a capture oligonucleotide hybridized to the single-stranded monomer arms or terminal arms. In some embodiments, the capture oligonucleotide may be reversibly or irreversibly cross-linked to the monomer arm. Alternately, the targeting agent can be chemically attached via hydrophilic or hydrophobic binding characteristics (including via electrostatic attraction and hydrogen binding) to the single-stranded arm or terminal arm, or attached by binding between a hapten and its binding partner (e.g., biotin and streptavidin). Additional examples of methods of conjugating a targeting agent to a nucleic acid carrier can be found in, for example, U.S. Patent Publication No. 2005/0089890 and PCT Publications WO 2008/147526, WO 2010/017544, and WO 2011/106481, each of which is incorporated herein by reference in their entirety.

In some embodiments, one or more of the targeting agents is, for example, an antigen, a peptide, an antibody or fragment thereof, an antibody-drug conjugate, a non-antibody scaffold, a label, an adjuvant, an RNA molecule, a DNA molecule, a vitamin, a protein, a fusion protein, a fusion peptide, a carbohydrate, a lipid, a polysaccharide, a lipopolysaccharide, a polymer, a virus particle, or a virus-like particle, or any combination thereof.

Any nucleic acid carrier can comprise any combination of any of these targeting agents. For example, a monomeric nucleic acid carrier can comprise up to any four of these targeting agents. Thus, a monomeric nucleic acid carrier can comprise one, two, three, or four of these targeting agents. As another example, a double monomer nucleic acid carrier can comprise up to any six of these targeting agents. Thus, a double monomer nucleic acid carrier can comprise one, two, three, four, five, or six of these targeting agents.

In some embodiments, the vitamin is folic acid.

In some embodiments, the carbohydrate is mannose.

In some embodiments, the polymer is hyaluronic acid, polyargenine, polylysine, polyethylenimine (PEI), polyethyleneglycol (PEG), polyglycolic acid (PGA), polylactic acid (PLA), or poly(lactic-co-glycolic acid) (PLGA).

In some embodiments, the RNA molecule is siRNA, miRNA, mRNA, snRNA, dsRNA, ncRNA, snoRNA, or an aptamer.

In some embodiments, the non-antibody scaffold is an affibody, an affilin, an anticalin, an atrimer, an avimer, a bicyclic peptide, a cys-knot, a DARPin, an FN3, a fynomer, a kunitz domain, or an O-body.

In some embodiments, the antigen is a bacterial antigen, a viral antigen, a fungal antigen, a yeast antigen, a protozoan antigen, or prion. In some embodiments, the antigen is from *Acetobacter aurantius, Acinetobacter baumannii, Acinetobacter calcoaceticus, Acinetobacter haemolyticus, Acinetobacter junii, Acinetobacter lwoffii, Actinomyces israelii, Actinomyces viscosus, Aggregatibacter actinomycetemcomitans, Agrobacterium radiobacter, Agrobacterium tumefaciens, Azorhizobium caulinodans, Azotobacter vinelandii, Anaplasma phagocytophilum, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides gingivalis, Bacteroides fragilis, Bacteroides melaninogenicus (Prevotella melaninogenica), Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae (Chlamydia pneumoniae), Chlamydophila psittaci (Chlamydia psittaci), Citrobacter freundii, Citrobacter diverus, Citrobacter koseri, Clostridium botulinum, Clostridium difficile, Clostridium perfringens (Clostridium welchii), Clostridium tetani, Corynebacterium diphtheria, Corynebacterium fusiforme, Coxiella burnetii, Ehrlichia chaffeensis, Enterobacter aerogenes, Enterobacter cloacae, Enterobacter faecalis, Enterococcus avium, Enterococcus durans, Enterococcus faecalis, Enterococcus faecium, Enterococcus galllinarum, Enterococcus maloratus, Eschericia coli, Francisella tularensis, Fusobacterium nucleatum, Gardnerella vaginalis, Haemophilus ducreyi, Haemophilus parainfluenzae, Haemophilus pertussis, Haemophilus vaginalis, Haemophilus influenza, Haemophilus aegyptius, Helicobacter pylori, Klebsiella pneumonia, Klebsiella oxytoca, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella lacunata, Moraxella catarrhalis, Morganella morganii, Mycobacterium avium, Mycobacterium africanum, Mycobacterium bovis, Mycobacterium canetti, Mycobacterium diphtheria, Mycobacterium intracellulare, Mycobacterium leprae, Mycobacterium lepraemurium, Mycobacterium microti, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumonia, Neisseria gonorrhoeae, Neisseria meningitides, Pasteurella multocida, Pasteurella tularensis, Porphyromonas gingivalis, Prevotella melaninogenica (Bacteroides melaninogenicus), Propionibacterium acnes, Proteus mirabillis, Proteus vulgaris, Providencia stuartii, Pseudomonas aeruginosa, Pseudomonas otitidis, Rhizobium radiobacter, Rickettsia prowazekii, Rickettsia psittaci, Rickettsia quintana, Rickettsia rickettsia, Rickettsia trachomae, Rochalimaea henselae, Rochalimaea Quintana, Rothia dentocariosa, Salmonella enteritidis, Salmonella typhi, Salmonella typhimurium, Serratia marcescens, Shigella dysenteriae, Staphylococcus aureus*, methicillin-resistant *Staphylococcus aureus, Staphylococcus pneumoniae, Staphylococcus epidermidis, Staphylococcus saprophyticus, Staphylococcus colmii, Staphylococcus sciuri, Staphylococcus warneri, Stenotrophomonas maltophilia, Streptococcus agalactiae, Streptococcus anginosus, Streptococcus avium, Streptococcus bovis, Streptococcus cricetus, Streptococcus faceium, Streptococcus faecalis, Streptococcus ferus, Streptococcus gallinarum, Streptococcus lactis. Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Streptococcus viridans, Treponema pallidum, Treponema denticola, Vibrio cholera, Vibrio comma, Vibrio parahaemolyticus, Vibrio vulnificus, Wolbachia, Yersinia enterocolitica, Yersinia pestis, Yersinia pseudotuberculosis, Aspergillus fumigatus, Aspergillus flavus, Aspergillus clavatus, Aspergillus niger, Aspergillus terreus, Candida albicans, Candida glabrata, Candida tropicalis, Candida krusei, Candida dubliniensis, Candida parapsilosis, Fusarium solani, Fusarium moniliforme, Fusarium proliferartum, Malessezia pachydermatis, Chrysosporium parvum, Metarhizium anisopliae, Phaeoisaria clematidis*, or *Sarcopodium oculorum*. In some embodiments, the antigen is from *Mycobacterium tuberculosis*, Varicella zoster virus, *Corynebacterium diphtheria*, Hepatitis A virus, Hepatitis B virus, Hepatitis C virus, Haemophilus influenza, Human Papillomavirus, Influenza virus, Japanese Encephalitis virus, Measles virus, *Neisseria meningitidis*, Mumps virus, *Bordetella pertussis, Streptococcus pneumonia*, Poliovirus, Rabies virus, Rotavirus, Rubella virus, Herpes Zoster virus, *Clostridium tetani, Salmonella typhi*, Yellow Fever virus, Ebola virus, avian flu virus, *Bacillus anthracis*, Smallpox virus, or Zika virus.

In some embodiments, the antibody fragment is Fab, F(ab')$_2$, scFv, tandem scFv, a BiTE, single domain (sdAb) antibody, diabody, single chain diabody, minibody, fusion protein, or scFv-Fc. In some embodiments, the antibody, or fragment thereof, is directed to a disease-associated antigen. In some embodiments, the disease-associated antigen is a tumor-associated antigen. Table 1 lists exemplary antibodies (or fragments thereof) to tumor-associated antigens.

TABLE 1

| Name | Target | Cancer |
|---|---|---|
| 3F8 | GD2 | neuroblastoma |
| 8H9 | B7-H3 | neuroblastoma, sarcoma, brain |
| Abagovomab | CA-125, MUC16 | ovarian |
| Abituzumab | CD51 | cancer |
| Adecatumumab | EpCAM | prostate, breast |
| Afutuzumab | CD20 | lymphoma |
| Alacizumab pegol | VEGFR2 | cancer |
| Alemtuzumab | CD52 | chronic lymphocytic leukemia |
| Amatuximab | mesothelin | cancer |
| AMP-514 | PD-1 | advanced malignancy |
| AMP-224 | PD-1 | colorectal |
| Anatumomab mafenatox | TAG-72 | non-small cell lung carcinoma |
| Anetumab ravtansine | MSLN | cancer |
| Apolizumab | HLA-DR | hematological |
| Ascrinvacumab | activin receptor-like kinase 1 | cancer |
| Atezolizumab | CD274, PD-L1 | urothelial bladder cancer, non-small cell lung carcinoma, melanoma, breast, renal cell carcinoma |
| Avelumab | PD-L1 | solid tumors, non-small cell lung carcinoma, metastatic Merkel cell carcinoma |
| Bavituximab | phosphatidylserine | cancer |
| Belimumab | BAFF | non-Hodgkin lymphoma |
| Bevacizumab | VEGF-A | breast, cervical, colorectal, non-small cell lung carcinoma, renal cell carcinoma, ovarian, glioblastoma |
| Bivatuzumab mertansine | CD44 v6 | squamous cell carcinoma |
| Blinatumomab | CD19 | acute lymphoblastic leukemia |
| BMS-986016 | LAG-3 | breast, hematological, advanced solid tumor |
| BMS-936559 | PD-L1 | non-small cell lung carcinoma, renal cell carcinoma |
| Bosutinib | BCR-ABL | acute lymphoblastic leukemia |
| Brentuximab vedotin | CD30 (TNFRSF8) | hematologic, Hodgkin's lymphoma |
| Cantuzumab mertansine | mucin CanAg | colorectal |
| Cantuzumab ravtansine | MUC1 | cancer |
| Carlumab | MCP-1 | cancer |
| Catumaxomab | EpCAM, CD3 | ovarian, gastric, malignant ascites |
| CBR96-doxorubicin immunoconjugate | Lewis-Y antigen | cancer |
| Cetuximab | EGFR | colorectal, head and neck cancer |
| Ch.14.18 | unknown | neuroblastoma |
| CIMAvax | EGF | non-small cell lung carcinoma |
| Citatuzumab bogatox | EpCAM | ovarian, solid tumors |
| Cixutumumab | IGF-1 receptor | solid tumors |
| Clivatuzumab tetraxetan | MUC1 | pancreatic cancer |
| Codrituzumab | glypican 3 | cancer |
| Coltuximab ravtansine | CD19 | cancer |
| Conatumumab | TRAIL-R2 | cancer |
| Dacetuzumab | CD40 | hematologic |
| Dalotuzumab | insulin-like growth factor I receptor | cancer |
| Daratumumab | CD38 (cyclic ADP ribose hydrolase) | cancer |
| Dasatinib | BCR-ABL | chronic myeloid leukemia |
| Demcizumab | DLL4 | cancer |
| Denintuzumab mafodotin | CD19 | cancer |
| Denosumab | RANKL | osteoporosis, bone metastases |
| Derlotuximab biotin | histone complex | recurrent glioblastoma multiforme |
| Detumomab | B-lymphoma cell | lymphoma |
| Dinutuximab | ganglioside GD2 | neuroblastoma, retinoblastoma, melanoma |
| Drozitumab | DR5 | cancer |
| Durvalumab | CD274, PD-L1 | non-small cell lung carcinoma, head and neck, glioblastoma |
| Dusigitumab | ILGF2 | cancer |
| Ecromeximab | GD3 ganglioside | malignant melanoma |
| Edrecolomab | EpCAM | colorectal |
| Elgemtumab | ERBB3 | cancer |
| Elotuzumab | SLAMF7, CS1 | multiple myeloma |
| Emactuzumab | CSF1R | cancer |
| EMD640744 | survivin | melanoma, glioma, solid tumors |
| Emibetuzumab | HHGFR | cancer |
| Enavatuzumab | TWEAK receptor | cancer |
| Enfortumab vedotin | AGS-22M6 | cancer expressing Nectin-4 |
| Enoblituzumab | B7-H3 | cancer |
| Ensituximab | 5AC | cancer |

TABLE 1-continued

| Name | Target | Cancer |
|---|---|---|
| Epratuzumab | CD22 | acute lymphoblastic leukemia |
| Ertumaxomab | HER2/neu, CD3 | breast |
| Etaracizumab | integrin αvβ3 | melanoma, prostate, ovarian |
| Farletuzumab | folate receptor 1 | ovarian |
| FBTA05 | CD20 | chronic lymphocytic leukemia |
| Ficlatuzumab | HGF | cancer |
| Figitumumab | IGF-1 receptor | adrenocortical carcinoma, non-small cell lung carcinoma |
| Flanvotumab | TYRP1 (glycoprotein 75) | melanoma |
| Fresolimumab | TGF-β | cancer |
| Galiximab | CD80 | B-cell lymphoma |
| Ganitumab | IGF-I | cancer |
| Gemtuzumab ozogamicin | CD33 | acute myelogenous leukemia |
| Girentuximab | carbonic anhydrase 9 (CA-IX) | clear cell renal cell carcinoma |
| Glembatumumab vedotin | GPNMB | melanoma, breast |
| gp100:209-217 (210M) | gp100 | melanoma |
| HPV-16 | HPV-16 | cervical |
| Ibritumomab tiuxetan | CD20 | non-Hodgkin's lymphoma, chronic lymphocytic leukemia, B cell non-Hodgkin's lymphoma, pre-B acute lymphoblastic leukemia |
| Icrucumab | VEGFR-1 | cancer |
| IDH1(R132H) | IDH1 | glioma |
| IMAB362 | CLDN18.2 | gastrointestinal adenocarcinoma and pancreatic tumor |
| Imalumab | MIF | cancer |
| Imatinib | BCR-ABL | chronic myeloid leukemia |
| Imgatuzumab | EGFR | cancer |
| Indatuximab ravtansine | SDC1 | cancer |
| Indoximod | IDO1 | breast, melanoma, non-small cell lung carcinoma |
| Indusatumab vedotin | GUCY2C | cancer |
| Intetumumab | CD51 | solid tumors, prostate, melanoma |
| Inotuzumab ozogamicin | CD22 | acute lymphoblastic leukemia |
| Ipilimumab | CD152, CTLA-4 | melanoma |
| Iratumumab | CD30 (TNFRSF8) | Hodgkin's lymphoma |
| Isatuximab | CD38 | cancer |
| ISCOMATRIX | NY-ESO-1 | ovarian, melanoma |
| Labetuzumab | CEA | colorectal |
| Lexatumumab | TRAIL-R2 | cancer |
| Lifastuzumab vedotin | phosphate-sodium co-transporter | cancer |
| Lilotomab satetraxetan | CD37 | cancer |
| Lintuzumab | CD33 | cancer |
| Lirilumab | KIR | lymphoma |
| Lorvotuzumab mertansine | CD56 | cancer |
| Lucatumumab | CD40 | multiple myeloma, non-Hodgkin's lymphoma, Hodgkin's lymphoma |
| Lumiliximab | CD23 (IgE receptor) | chronic lymphocytic leukemia |
| Lumretuzumab | ERBB3 | cancer |
| LY6K-177 | LY6K | gastric |
| Mapatumumab | TRAIL-R1 | cancer |
| Margetuximab | ch4D5 | cancer |
| MART-1(26-35, 27L) | Melan-A | melanoma |
| Matuzumab | EGFR | colorectal, lung, stomach |
| MED19447 | CD73 | advanced solid tumors |
| Milatuzumab | CD74 | multiple myeloma and hematological malignancies |
| Mirvetuximab soravtansine | folate receptor alpha | cancer |
| Mitumomab | GD3 ganglioside | small cell lung carcinoma |
| Mogamulizumab | CCR4 | cancer |
| Moxetumomab pasudotox | CD22 | acute lymphoblastic leukemia |
| Nacolomab tafenatox | C242 antigen | colorectal |
| Naptumomab estafenatox | 5T4 | non-small cell lung carcinoma, renal cell carcinoma, colorectal, prostate |
| Narnatumab | RON | cancer |
| Necitumumab | EGFR | non-small cell lung carcinoma |
| Nesvacumab | angiopoietin 2 | cancer |
| Nilotinib | BCR-ABL | acute lymphoblastic leukemia |
| Nimotuzumab | EGFR | squamous cell carcinoma, head & neck, nasopharyngeal, glioma, |
| Nivolumab | PD-1 | metastatic melanoma, non-small cell lung carcinoma |

TABLE 1-continued

| Name | Target | Cancer |
|---|---|---|
| Obinutuzumab | CD20 | Chronic lymphatic leukemia |
| Ocaratuzumab | CD20 | cancer |
| Ofatumumab | CD20 | non-Hodgkin's lymphoma, chronic lymphocytic leukemia, B cell non-Hodgkin's lymphoma, pre-B acute lymphoblastic leukemia |
| Olaratumab | PDGF-R α | cancer |
| Onartuzumab | MET, human scatter factor receptor kinase | non-small cell lung carcinoma |
| Ontuxizumab | TEM1 | cancer |
| Oportuzumab monatox | EpCAM | cancer |
| Oregovomab | CA-125, MUC16 | ovarian |
| Otlertuzumab | CD37 | cancer |
| Panitumumab | EGFR | colorectal, head and neck |
| Pankomab | tumor specific glycosylation of MUC1 | ovarian cancer |
| PANVAC | CEA | colorectal |
| Parsatuzumab | EGFL7 | cancer |
| Pasotuxizumab | folate hydrolase | cancer |
| Patritumab | HER3 | cancer |
| PBF-509 | A2aR | non-small cell lung carcinoma |
| Pembrolizumab | PD-1 | metastatic melanoma, non-small cell lung carcinoma |
| Pemtumomab | MUC1 | cancer |
| Pertuzumab | HER2/neu | breast |
| Pidilizumab | PD-1 | B cell lymphoma, metastatic melanoma, colorectal |
| Pinatuzumab vedotin | CD22 | cancer |
| Polatuzumab vedotin | CD79B | cancer |
| Ponotinib | BCR-ABL | acute lymphoblastic leukemia |
| Pritumumab | vimentin | brain |
| PROSTVAC | PSA | prostate |
| Racotumomab | N-glycolylneuraminic acid | non-small cell lung carcinoma, breast, melanoma |
| Radretumab | fibronectin extra domain-B | cancer |
| Ramucirumab | VEGF-R2 | gastric, non-small cell lung carcinoma |
| RecMAGE-A3 | MAGE-A3 | melanoma |
| Rilotumumab | HGF | solid tumors |
| Rituximab | CD20 | non-Hodgkin's lymphoma, chronic lymphocytic leukemia, B cell non-Hodgkin's lymphoma, pre-B acute lymphoblastic leukemia |
| Robatumumab | IGF-1 receptor | cancer |
| Sacituzumab govitecan | tumor-associated calcium signal transducer 2 | cancer |
| Samalizumab | CD200 | cancer |
| Seribantumab | ERBB3 | cancer |
| Sibrotuzumab | FAP | cancer |
| SGN-CD19A | CD19 | acute lymphoblastic leukemia, B-cell non-Hodgkin lymphoma |
| SGN-CD33A | CD33 | acute myeloid leukemia |
| Siltuximab | IL-6 | cancer |
| Sipuleucel-T | PAP | prostate |
| Sofituzumab vedotin | CA 125 | ovarian |
| Tabalumab | BAFF | B-cell |
| Tacatuzumab tetraxetan | alpha-fetoprotein | cancer |
| Taplitumomab paptox | CD19 | cancer |
| Tarextumab | Notch receptor | cancer |
| Tecemotide | MUC1 | non-small cell lung carcinoma, breast |
| Tenatumomab | tenascin C | cancer |
| Teprotumumab | CD221 | hematologic |
| Tertomotide | telomerase | pancreatic |
| Tetulomab | CD37 | cancer |
| TGN1412 | CD28 | chronic lymphocytic leukemia |
| Theratope | sialyl-Tn | breast |
| Ticilimumab | CTLA-4 | cancer |
| Tigatuzumab | TRAIL-R2 | cancer |
| TNX-650 | IL-13 | Hodgkin's lymphoma |
| Tositumomab | CD20 | follicular lymphoma, non-Hodgkin's lymphoma, chronic lymphocytic leukemia, B cell non-Hodgkin's lymphoma, pre-B acute lymphoblastic leukemia |
| Tovetumab | CD140a | cancer |
| Trastuzumab | HER2/neu | breast |
| TRBS07 | GD2 | melanoma |
| Tremelimumab | CTLA-4 | malignant mesothelioma |

TABLE 1-continued

| Name | Target | Cancer |
| --- | --- | --- |
| Tucotuzumab celmoleukin | EpCAM | cancer |
| Ublituximab | MS4A1 | cancer |
| Ulocuplumab | C-X-C chemokine receptor type 4 | hematologic malignancies |
| Urelumab | CD137, 4-1BB | advanced solid tumors |
| Vandortuzumab vedotin | STEAP1 | cancer |
| Vantictumab | Frizzled receptor | cancer |
| Vanucizumab | angiopoietin 2 | cancer |
| Veltuzumab | CD20 | non-Hodgkin's lymphoma |
| Volociximab | integrin α5β1 | solid tumors |
| Vorsetuzumab mafodotin | CD70 | cancer |
| Votumumab | tumor antigen CTAA16.88 | colorectal |
| WT1 peptide vaccine | WT1 | ovarian, uterine, acute myelogenous leukemia |
| Zalutumumab | EGFR | squamous cell carcinoma head and neck |
| Zastumotide | MAGE-A3 | non-small cell lung carcinoma |
| Zatuximab | HER1 | cancer |

In some embodiments, the tumor-associated antigen is 4-1BB, 5AC, 5T4, A2aR, activin receptor-like kinase 1, AGS-22M6, AKAP4, alpha-fetoprotein, angiopoietin 2, B7-H3, BAFF, BAGE, BCR-ABL, BORIS, CA-125, CA19-9, C242 antigen, carbonic anhydrase 9 (CA-IX), CCR4, CD19, CD20, CD22, CD23 (IgE receptor), CD24, CD28, CD30 (TNFRSF8), CD33, CD37, CD38 (cyclic ADP ribose hydrolase), CD40, CD44 v6, CD51, CD56, CD70, CD71, CD73, CD74, CD79B, CD80, CD137, CD140a, CD152, CD200, CD221, CD274, CEA, ch4D5, CLDN18.2, CS1, CSF1R, CTLA-4, C-X-C chemokine receptor type 4, DLL4, DR5, EBAG9, EGF, EGFR, EGFL7, EpCAM, ERBB2, ERBB3, FAP, fibronectin extra domain-B, folate receptor 1, folate receptor alpha, folate hydrolase, Frizzled receptor, GAGE, GD2 ganglioside, GD3 ganglioside, glioma, glypican 3, GPNMB, gp100, GUCY2C, HER1, HER2/neu, HER3, HGF, HHGFR, histone complex, HLA-DR, human scatter factor receptor kinase, HPV-16, HSP105, IDH1, IDO1, IGF-I, IGF-1 receptor, ILGF2, IL-6, IL-13, integrin αvβ3, integrin α5β1, KIR, LAG-3, Lewis-Y antigen, LY6K, MAGE-1, MAGE-A3, MAGE-C2, MAGE-D4, MAPG, MART-1, Melan-A, MET, MCP-1, mesothelin, MIF, MSLN, MS4A1, mucin CanAg, MUC1, MUC4, MUC16, NG2, N-glycolylneuraminic acid, Notch receptor PD-1, NY-ESO-1, OCAA, PAP, PDGF-R α, PDCD1, PD1, PD-L1, phosphate-sodium co-transporter, phosphatidylserine, PRAME, PSA, RANKL, RON, ROR1, SDC1, Sialyl-Tn, SLAMF7, SPAG-9, SSX1, STEAP1, survivin, TAG-72, telomerase, TEM1, tenascin C, TGF-β, TIM-3, TLR, TAM, TIM-3, TRAIL-R2, TRAIL-R1, TWEAK receptor, tumor specific glycosylation of MUC1, tumor-associated calcium signal transducer 2, tumor antigen CTAA16.88, TYRP1 (glycoprotein 75), VEGF-A, VEGFR2, VEGFR-1, vimentin, VISTA, WT1, or XAGE-1b. In some embodiments, the tumor-associated antigen is HER-2, EGFR, CD30, CD20, EpCAM, NG2, CD19, CEA, MUC-1, CA19-9, OCAA, MAPG, TAM, TLR, CD71, ERBB2, VEGF, or glioma.

Table 2 lists exemplary antibodies (or fragments thereof) to disease-associated antigens.

TABLE 2

| Name | Target | Use/Indication |
| --- | --- | --- |
| Abciximab | CD41 (integrin alpha-IIb) | platelet aggregation inhibitor |
| Abrilumab | integrin α4β7 | inflammatory bowel disease, ulcerative colitis, Crohn's disease |
| Actoxumab | *Clostridium difficile* | *Clostridium difficile* infection |
| Adalimumab | TNF-α | rheumatoid arthritis, Crohn's Disease, plaque psoriasis, psoriatic arthritis, ankylosing spondylitis, juvenile idiopathic arthritis, hemolytic disease of the newborn |
| Aducanumab | beta-amyloid | Alzheimer's disease |
| Afelimomab | TNF-α | sepsis |
| ALD518 | IL-6 | rheumatoid arthritis |
| Alemtuzumab | CD52 | multiple sclerosis |
| Alirocumab | PCSK9 | hypercholesterolemia |
| Anifrolumab | interferon α/β receptor | systemic lupus erythematosus |
| Atlizumab | IL-6 receptor | rheumatoid arthritis |
| Atorolimumab | Rhesus factor | hemolytic disease of the newborn |
| Bapineuzumab | beta amyloid | Alzheimer's disease |
| Basiliximab | CD25 (α chain of IL-2 receptor) | prevention of organ transplant rejections |
| Bavituximab | phosphatidylserine | viral infections |
| Benralizumab | CD125 | asthma |
| Bertilimumab | CCL11 (eotaxin-1) | severe allergic disorders |
| Besilesomab | CEA-related antigen | inflammatory lesions |
| Bezlotoxumab | *Clostridium difficile* | *Clostridium difficile* infection |
| Bimagrumab | ACVR2B | myostatin inhibitor |

TABLE 2-continued

| Name | Target | Use/Indication |
|---|---|---|
| Blosozumab | SOST | osteoporosis |
| Bococizumab | neural apoptosis-regulated proteinase 1 | dyslipidemia |
| Briakinumab | IL-12, IL-23 | psoriasis, rheumatoid arthritis, inflammatory bowel diseases, multiple sclerosis |
| Brodalumab | IL-17 | inflammatory diseases |
| Canakinumab | IL-1? | rheumatoid arthritis |
| Caplacizumab | VWF | thrombotic thrombocytopenia purpura, thrombosis |
| Cedelizumab | CD4 | prevention of organ transplant rejection, autoimmune diseases |
| Certolizumab pegol | TNF-α | Crohn's disease |
| Clazakizumab | Oryctolagus cuniculus | rheumatoid arthritis |
| Clenoliximab | CD4 | rheumatoid arthritis |
| Concizumab | TFPI | bleeding |
| Crenezumab | 1-40-β-amyloid | Alzheimer's disease |
| CR6261 | Influenza A hemagglutinin | infectious disease/influenza A |
| Daclizumab | CD25 (α chain of IL-2 receptor) | prevention of organ transplant rejection |
| Denosumab | RANKL | osteoporosis, bone metastases etc. |
| Diridavumab | hemagglutinin | influenza A |
| Dupilumab | IL4 | atopic diseases |
| Eculizumab | C5 | paroxysmal nocturnal hemoglobinuria |
| Edobacomab | endotoxin | sepsis caused by Gram-negative bacteria |
| Efalizumab | LFA-1 (CD11a) | psoriasis (blocks T-cell migration) |
| Efungumab | Hsp90 | invasive Candida infection |
| Eldelumab | interferon gamma-induced protein | Crohn's disease, ulcerative colitis |
| Enokizumab | IL9 | asthma |
| Erlizumab | ITGB2 (CD18) | heart attack, stroke, traumatic shock |
| Etrolizumab | integrin α7 β7 | inflammatory bowel disease |
| Evinacumab | angiopoietin 3 | dyslipidemia |
| Evolocumab | PCSK9 | hypercholesterolemia |
| Exbivirumab | hepatitis B surface Ag | hepatitis B |
| Fasinumab | HNGF | acute sciatic pain |
| Felvizumab | respiratory syncytial virus | respiratory syncytial virus infection |
| Fezakinumab | IL-22 | rheumatoid arthritis, psoriasis |
| Fletikumab | IL 20 | rheumatoid arthritis |
| Fontolizumab | IFN-γ | Crohn's disease |
| Foravirumab | rabies virus glycoprotein | rabies (prophylaxis) |
| Fresolimumab | TGF-β | idiopathic pulmonary fibrosis, focal segmental glomerulosclerosis |
| Gantenerumab | beta amyloid | Alzheimer's disease |
| Gavilimomab | CD147 (basigin) | graft versus host disease |
| Gevokizumab | IL-1β | diabetes |
| Golimumab | TNF-α | rheumatoid arthritis, psoriatic arthritis, ankylosing spondylitis |
| Gomiliximab | CD23 (IgE receptor) | allergic asthma |
| Guselkumab | IL23 | psoriasis |
| Ibalizumab | CD4 | HIV infection |
| Infliximab | TNF-α | rheumatoid arthritis, ankylosing spondylitis, psoriatic arthritis, psoriasis, Crohn's disease, ulcerative colitis |
| Inolimomab | CD25 (α chain of IL-2 receptor) | graft versus host disease |
| Ixekizumab | IL-17A | autoimmune diseases |
| Keliximab | CD4 | chronic asthma |
| Lebrikizumab | IL-13 | asthma |
| Lerdelimumab | TGF beta 2 | reduction of scarring after glaucoma surgery |
| Libivirumab | hepatitis B surface Ag | hepatitis B |
| Ligelizumab | IGHE | severe asthma and chronic spontaneous urticaria |
| Lodelcizumab | PCSK9 | hypercholesterolemia |
| Lulizumab pegol | CD28 | autoimmune diseases |
| Mavrilimumab | GMCSF receptor α-chain | rheumatoid arthritis |
| Mepolizumab | IL-5 | asthma and white blood cell diseases |
| Metelimumab | TGF beta 1 | systemic scleroderma |
| Motavizumab | respiratory syncytial virus | respiratory syncytial virus (prevention) |
| Muromonab-CD3 | CD3 | prevention of organ transplant rejections |
| Natalizumab | integrin α4 | multiple sclerosis, Crohn's disease |
| Nebacumab | endotoxin | sepsis |

TABLE 2-continued

| Name | Target | Use/Indication |
|---|---|---|
| Obiltoxaximab | *Bacillus anthracis* | *Bacillus anthracis* spores |
| Ocrelizumab | CD20 | rheumatoid arthritis, lupus erythematosus |
| Odulimomab | LFA-1 (CD11a) | prevention of organ transplant rejections, immunological diseases |
| Omalizumab | IgE Fc region | allergic asthma |
| Opicinumab | LINGO-1 | multiple sclerosis |
| Otelixizumab | CD3 | diabetes mellitus type 1 |
| Oxelumab | OX-40 | asthma |
| Ozanezumab | NOGO-A | ALS and multiple sclerosis |
| Ozoralizumab | TNF-α | inflammation |
| Pagibaximab | lipoteichoic acid | sepsis (Staphylococcus) |
| Palivizumab | F protein of respiratory syncytial virus | respiratory syncytial virus (prevention) |
| Panobacumab | *P. aeruginosa* | *P. aeruginosa* infection |
| Pascolizumab | IL-4 | asthma |
| Perakizumab | IL17A | arthritis |
| Pexelizumab | C5 | reduction of side effects of cardiac surgery |
| Ponezumab | human beta-amyloid | Alzheimer's disease |
| Priliximab | CD4 | Crohn's disease, multiple sclerosis |
| PRO 140 | CCR5 | HIV infection |
| Quilizumab | IGHE | asthma |
| Rafivirumab | rabies virus glycoprotein | rabies (prophylaxis) |
| Ralpancizumab | neural apoptosis-regulated proteinase 1 | dyslipidemia |
| Ranibizumab | VEGF-A | macular degeneration (wet form) |
| Raxibacumab | anthrax toxin, protective antigen | anthrax (prophylaxis and treatment) |
| Refanezumab | myelin-associated glycoprotein | recovery of motor function after stroke |
| Regavirumab | cytomegalovirus glycoprotein B | cytomegalovirus infection |
| Reslizumab | IL-5 | inflammations of the airways, skin and gastrointestinal tract |
| Rinucumab | platelet-derived growth factor receptor beta | neovascular age-related macular degeneration |
| Romosozumab | sclerostin | osteoporosis |
| Rontalizumab | IFN-α | systemic lupus erythematosus |
| Rovelizumab | CD11, CD18 | haemorrhagic shock |
| Rupluzumab | CD154 (CD40L) | rheumatic diseases |
| Sarilumab | IL6 | rheumatoid arthritis, ankylosing spondylitis |
| Secukinumab | IL-17A | uveitis, rheumatoid arthritis psoriasis |
| Sevirumab | cytomegalovirus | cytomegalovirus infection |
| Sifalimumab | IFN-a | SLE, dermatomyositis, polymyositis |
| Simtuzumab | LOXL2 | fibrosis |
| Siplizumab | CD2 | psoriasis, graft-versus-host disease (prevention) |
| Sirukumab | IL-6 | rheumatoid arthritis |
| Solanezumab | beta amyloid | Alzheimer's disease |
| Sonepcizumab | sphingosine-1-phosphate | choroidal and retinal neovascularization |
| Stamulumab | myostatin | muscular dystrophy |
| Suvizumab | HIV-1 | viral infections |
| Tadocizumab | integrin αIIbβ3 | percutaneous coronary intervention |
| Talizumab | IgE | allergic reaction |
| Tanezumab | NGF | pain |
| Tefibazumab | clumping factor A | *Staphylococcus aureus* infection |
| Teplizumab | CD3 | diabetes mellitus type 1 |
| TGN1412 | CD28 | rheumatoid arthritis |
| Tildrakizumab | IL23 | inflammatory disorders |
| Tocilizumab | IL-6 receptor | rheumatoid arthritis |
| Toralizumab | CD154 (CD40L) | rheumatoid arthritis, lupus nephritis |
| Tralokinumab | IL-13 | asthma |
| Trevogrumab | growth differentiation factor 8 | muscle atrophy due to orthopedic disuse and sarcopenia |
| Tuvirumab | hepatitis B virus | chronic hepatitis B |
| Urtoxazumab | *Escherichia coli* | diarrhoea caused by *E. coli* |
| Ustekinumab | IL-12, IL-23 | multiple sclerosis, psoriasis, psoriatic arthritis |
| Vedolizumab | integrin α4β7 | Crohn's disease, ulcerative colitis |
| Vepalimomab | AOC3 (VAP-1) | inflammation |
| Visilizumab | CD3 | Crohn's disease, ulcerative colitis |
| Zanolimumab | CD4 | rheumatoid arthritis, psoriasis |
| Zolimomab aritox | CD5 | systemic lupus erythematosus, graft-versus-host disease |

In some embodiments, the disease-associated antigen is 1-40-β-amyloid, AOC3 (VAP-1), ACVR2B, angiopoietin 3, beta-amyloid, C5, CCL11 (eotaxin-1), CCR5, CD2, CD3, CD4, CD5, CD11, CD18, CD20, CD23 (IgE receptor), CD25 (a chain of IL-2 receptor), CD28, CD41 (integrin alpha-IIb), CD52, CD125, CD147 (basigin), CD154 (CD40L), CEA-related antigen, clumping factor A, endotoxin, GMCSF receptor α-chain, growth differentiation factor 8, hemagglutinin, HNGF, Hsp90, IGHE, IgE Fc region, IL-1β, IL-4, IL-5, IL-6, IL-9, IL-12, IL-13, IL-17, IL-17A, IL-20, IL-22, IL-23, IL-6 receptor, integrin α4β7, integrin α7β7, integrin α4, integrin αIIbβ3, interferon α/β receptor, interferon gamma-induced protein, IFN-γ, IFN-α, ITGB2 (CD18), LFA-1 (CD11a), LINGO-1, lipoteichoic acid, LOXL2, myelin-associated glycoprotein, myostatin, neural apoptosis-regulated proteinase 1, NGF, NOGO-A, Oryctolagus cuniculus, OX-40, PCSK9, phosphatidylserine, platelet-derived growth factor receptor beta, RANKL, Rhesus factor, sclerostin, SOST, sphingosine-1-phosphate, TFPI, TGF-β, TGF beta 2, TGF beta 1, TNF-α, VEGF-A, or VWF.

In some embodiments, the antibody, or fragment thereof, is directed to a cell surface marker. In some embodiments, the cell surface marker is on an immune cell. In some embodiments, the immune cell is a T cell, B cell, NK cell, macrophage, TIL, dendritic cell, neutrophil, eosinophil, basophil, or mast cell. In some embodiments, the T cell is a $CD4^+$ T cell, $CD8^+$ T cell, helper T cell, regulatory T cell, cytotoxic T cell, or natural killer T cell; and wherein the B cell is a memory B cell or a plasma cell. In some embodiments, the cell surface marker is CD36, CD68, CD83, CD180, CD206 (MRC1-mannose receptor), F4/80 (EGF-TM7 family), CD205, CD56, CD161, CD94:NKG2 heterodimer, KIR/CD158 family, CD335, CD64, CD16, CD3, CD28, CD4, CD25, CD39, Toll-like receptors (TLRs), CD281, CD283, CD284, CD286, CD289, CD282, C-type lectin receptors (CLRs), Fc Receptor, or HSG.

In some embodiments, the nucleic acid carrier comprises one or two of the following: a first targeting agent which is an antibody, or fragment thereof, directed to HER2 and a second targeting agent which is an antibody, or fragment thereof, directed to CD64; a first targeting agent which is an antibody, or fragment thereof, directed to EGFR and a second targeting agent which is an antibody, or fragment thereof, directed to PD-1; a first targeting agent which is an antibody, or fragment thereof, directed to PD-L1 and a second targeting agent which is an antibody, or fragment thereof, directed to OX-40; a first targeting agent which is an antibody, or fragment thereof, directed to EGFR and a second targeting agent which is an antibody, or fragment thereof, directed to CD64; a first targeting agent which is an antibody, or fragment thereof, directed to CD30 and a second targeting agent which is an antibody, or fragment thereof, directed to CD16; a first targeting agent which is an antibody, or fragment thereof, directed to HER2 and a second targeting agent which is an antibody, or fragment thereof, directed to CD3; a first targeting agent which is an antibody, or fragment thereof, directed to CD20 and a second targeting agent which is an antibody, or fragment thereof, directed to CD3; a first targeting agent which is an antibody, or fragment thereof, directed to EpCAM and a second targeting agent which is an antibody, or fragment thereof, directed to CD3; a first targeting agent which is an antibody, or fragment thereof, directed to NG2 and a second targeting agent which is an antibody, or fragment thereof, directed to CD28; a first targeting agent which is an antibody, or fragment thereof, directed to CD19 and a second targeting agent which is an antibody, or fragment thereof, directed to CD3; a first targeting agent which is an antibody, or fragment thereof, directed to CD19 and a second targeting agent which is an antibody, or fragment thereof, directed to CD16; a first targeting agent which is an antibody, or fragment thereof, directed to CEA and a second targeting agent which is an antibody, or fragment thereof, directed to HSG; a first targeting agent which is an antibody, or fragment thereof, directed to MUC-1 and a second targeting agent which is an antibody, or fragment thereof, directed to HSG; a first targeting agent which is an antibody, or fragment thereof, directed to CA19-9 and a second targeting agent which is an antibody, or fragment thereof, directed to CD3; a first targeting agent which is an antibody, or fragment thereof, directed to CEA and a second targeting agent which is an antibody, or fragment thereof, directed to CD3; a first targeting agent which is an antibody, or fragment thereof, directed to OCAA and a second targeting agent which is an antibody, or fragment thereof, directed to CD3; a first targeting agent which is an antibody, or fragment thereof, directed to MAPG and a second targeting agent which is an antibody, or fragment thereof, directed to CD28; a first targeting agent which is an antibody, or fragment thereof, directed to HER2 and a second targeting agent which is an antibody, or fragment thereof, directed to CD16; a first targeting agent which is an antibody, or fragment thereof, directed to glioma and a second targeting agent which is an antibody, or fragment thereof, directed to CD3; a first targeting agent which is folic acid or folic acid receptor and a second targeting agent which is an antibody, or fragment thereof, directed to CD3 or CD16; and a first targeting agent which is an antibody, or fragment thereof, directed to PD-1 and a second targeting agent which is an antibody, or fragment thereof, directed to PDL-1 or PDL-2.

In some embodiments, the antibody, or fragment thereof, is an antibody-drug conjugate (ADC). In some embodiments, the nucleic acid carrier comprises one, two, three, for, five, or six, or more of the ADCs listed in Table 3. In some embodiments, the nucleic acid carrier may comprise multiple copies of the same ADC, as set forth above for targeting agents.

TABLE 3

| Name (drug) (linker) | Target | Indication |
| --- | --- | --- |
| Mylotarg (Calicheamycin) (Ac-But linker) | CD33 | AML |
| SGN-35 (MMAE) (Val-Cit) | CD30 | HL/ALCL |
| CMC-544 (Calicheamycin) (Ac-But linker) | CD22 | NHL |
| Kadcyla (DM1) (SMCC) | HER2 | breast cancer |
| IMGN901 (DM1) (SPP) | CD56 | SCLC |
| IMGN-388 (DM4) (SPDB) | αV-integrin | solid tumors |
| SAR3419 (DM4) (SPDB) | CD19 | DLBCL |
| BIIB015 (DM4) (NA) | Cripto | breast cancer |
| BT-062 (DM4) (SPDB) | CD138 | multiple myeloma |
| CDX-011 (MMAE) (Val-Cit) | GPNMB | breast cancer/melanoma |

TABLE 3-continued

| Name (drug) (linker) | Target | Indication |
|---|---|---|
| SGN-75 (MMAE) (MalC linker) | CD70 | NHL/RCC |
| PSMA ADC (MMAE) (Val-Cit) | PSMA | prostate cancer |
| MEDI-547 (MMAE) (MalC linker) | EphA2 | solid cancer |
| ASG-5ME (MMAE) (Val-Cit) | SLC44A4 | pancreatic cancer |
| ASG-15ME (MMAE) (Val-Cit) | SLITRK6 | lung cancer |
| ASG-22ME (MMAE) (Val-Cit) | Nectin-4 | solid tumors |
| MDX-1203 (Duocarmycin) (Val-Cit-PABC) | CD70 | NHL/RCC |
| BAY-94-9343 (DM4) (SPDB) | Mesothelin | mesotheliomas/ovarian tumor |
| MLN-0264 (MMAE) (NA) | Guanylyl cyclase | gastrointestinal tumor |
| MLN-2704 (DM1) (NA) | PSMA | prostate cancer |
| SGN-75 (MMAF) (Maleimidocaproyl) | CD70 | RCC |
| ABT-414 (NA) (NA) | EGFR | NSCLC |
| AMG-595 (DM1) (SMCC) | EGFRvIII | glioma |
| AMG-172 (DM1) (SMCC) | CD70 | RCC |
| RG-7596 (MMAE) (Val-Cit) | CD79b | NHL |
| RG-7600 (NA) (NA) | NA | ovarian tumor |
| SGN-CD19A (MMAE) (Maleimidocaproyl) | CD19 | AML/NHL |
| SGN-CD33A (PBD dimer) (MalC linker) | CD33 | drug-resistant AML |
| SGN-CD70A (PBD dimer) (NA) | CD70 | NHL/RCC |
| IMMU-110 (Doxorubicin) (Ac-But linker) | CD74 | multiple myeloma |
| IMMU-115 (Doxorubicin) (Ac-But linker) | CD74 | NHL/CLL |
| IMMU-132 (SN38) (Phenylalaninelysine) | TACSTD2 | solid tumors |
| IMMU-130 (SN38) (Phenylalaninelysine) | CEACAM5 | colorectal tumor |
| IMGN-529 (DM1) (SPP) | CD37 | hematologic tumors |
| IMGN-289 (DM1) (SPP) | EGFR | solid tumors |
| SAR-566658 (DM4) (SPDB) | DS6 | solid tumors |
| SYD985 (Duocarmycin) (NA) | HER2 | solid tumors |
| AGS67E (MMAE) (Val-Cit-PABC) | CD37 | CLL/AML |
| AGS-16M8F (MMAF) (MalC linker) | ENPP3 | renal cancer |
| SC16LD6.5 (D6.5) (NA) | Fyn3 | SCLC |
| DNIB0600A (MMAE) (Val-Cit) | NaPi2b | NSCLC |
| IMGN853 (DM4) (sulfo-SPDB) | FRα | ovarian cancer |

Abbreviations: AML: acute myeloid leukaemia; HL: Hodgkin's lymphoma; NHL: non-Hodgkin's lymphoma; ALCL: anaplasia large cell lymphoma; DLBCL: diffuse large B cell lymphoma; RCC: renal cell carcinoma; SCLC: small cell lung cancer; NSCLC: non-small cell lung cancer; CLL: chronic lymphocytic leukaemia; EGFR: epidermal growth factor receptor; GPNMB: glycoprotein NMB; PSMA: prostate-specific membrane antigen; NA: not available.

Highly potent drugs such as, for example, calicheamicins, doxorubicin, maytansinoids, auristatins, and camptothecin can be used as drug payloads for ADCs. Additional drug classes that may serve as drug payloads for ADCs include, but are not limited to, pyrrolobenzodiaze-pine (PDB) dimer, α-Amanitin, duocarmycin analogs, tubulysin B, and cryptophycin analogs. Additional ADCs include brentuximab vedotin and ado-trastuzumab emtansine.

In some embodiments, the label is a chemiluminescent agent, a fluorescent agent, an infrared dye, a radiolabel agent, a metal, a chelating agent, a hapten, or a gene or mRNA encoding a detectable protein. In some embodiments, the detectable protein is GFP or CFP.

In some embodiments, the adjuvant is one or more of a CpG containing oligonucleotide, a ssRNA, a dsRNA, a monophosphate lipid, aluminum, squalene, 3-deacyl-monophosphoryl lipid A, vitamin E, surfactant polysorbate 80, mannide-mono-oleate, SLAG-3, or a galactosylceramide. In some embodiments, the CpG containing oligonucleotide is ODN 1585 (ggggtcaacgttgagggggg; SEQ ID NO:1), ODN 1668 (tccatgacgttcctgatgct; SEQ ID NO:2), ODN 1826 (tccatgacgttcctgacgtt; SEQ ID NO:3), ODN 2006 (tcgtcgttttgtcgttttgtcgtt; SEQ ID NO:4), ODN 2007 (tcgtcgttgcgttttgtcgtt; SEQ ID NO:5), ODN 2216 (ggggacgatcgtcggggg; SEQ ID NO: 6), ODN 2336 (ggggacgacgtcgtgggggg; SEQ ID NO:7), ODN 2395 (tcgtcgttttcggcgcgcgccg; SEQ ID NO:8), ODN M362 (tcgtcgtcgttcgaacgacgacgttgat; SEQ ID NO: 9), AT-ODN-1 (tataattttaatttccaaga; SEQ ID NO:10), AT-ODN-2 (tataattttaccaactagc; SEQ ID NO: 11), ODNBW006 (tcgacgttcgtcgttcgtcgttc; SEQ ID NO:12), ODN 4084 (tcctggcggggaagt; SEQ ID NO:13), ODN INH-1 (cctggatgggaattccgaa; SEQ ID NO:14), ODN INH-47 (cctggatgggaattcccatccagg; SEQ ID NO:15), ODN INH-47 (tatggattttaattaaaatccata; SEQ ID NO: 16), ODN TTAGGG (tttagggttagggttagggttaggg; SEQ ID NO:17), or G-ODN (ctcctattgggggtttcctat; SEQ ID NO:18). In some embodiments, the CpG containing oligonucleotide is ODN 1668 (tccatgacgttcctgatgct; SEQ ID NO:2), ODN 1826 (tccatgacgttcctgacgtt; SEQ ID NO:3), ODN 2006 (tcgtcgttttgtcgttttgtcgtt; SEQ ID NO:4), ODN 2007 (tcgtcgttgcgttttgtcgtt; SEQ ID NO:5), ODN 2395 (tcgtcgttttcggcgcgcgccg; SEQ ID NO:8), ODN M362 (tcgtcgtcgttcgaacgacgacgttgat; SEQ ID NO:9), AT-ODN-1 (tataattttaatttccaaga; SEQ ID NO:10), AT-ODN-2 (tataattttaccaactagc; SEQ ID NO:11), ODNBW006 (tcgacgttcgtcgttcgtcgttc; SEQ ID NO:12), ODN 4084 (cctggatgggaa; SEQ ID NO:14), ODN INH-1 (cctggatgggaattcccatccagg; SEQ ID NO:15), ODN INH-47 (tatggattttaattaaaatccata; SEQ ID NO: 16), or ODN TTAGGG (tttagggttagggttagggttaggg; SEQ ID NO:17).

In some embodiments, the nucleic acid carrier comprises a targeting agent that is an antigen, an antibody, or a fragment of an antibody, and the oligonucleotide linker conjugating the targeting moiety to the single-stranded arm or terminal arm is or comprises a CpG containing oligonucleotide. In some embodiments, the nucleic acid carrier comprises at least one antigen, at least one antibody or fragment thereof directed to an immune cell, and at least one adjuvant.

The present disclosure also provides pharmaceutical compositions comprising any of the nucleic acid carriers described herein, or any combination thereof, and a pharmaceutically acceptable vehicle. In some embodiments, the pharmaceutically acceptable vehicle may be a diluent, filler, disintegrant, binder, lubricant, surfactant, hydrophobic vehicle, water soluble vehicle, emulsifier, buffer, humectant, moisturizer, solubilizer, preservative, and the like. Additional examples of vehicles include, but are not limited to, calcium carbonate, calcium phosphate, sodium phosphate, potassium phosphate, sodium chloride, various sugars, starches, cellulose derivatives, gelatin, and polymers such as polyethylene glycols, Cremophor EL (CrEL; polyoxyethyleneglycerol triricinoleate 35) and polysorbate 80 (Tween) 80; polyoxyethylene-sorbitan-20-monooleate).

The present disclosure also provides methods of making the monomeric nucleic acid carrier comprising: hybridizing the first oligonucleotide to the second oligonucleotide; and conjugating the at least one targeting agent to the at least one single-stranded arm. In some embodiments, the at least one targeting agent is further conjugated to an oligonucleotide linker prior to conjugating the at least one targeting agent to the at least one single-stranded arm. In some embodiments, the at least one targeting agent/oligonucleotide linker is conjugated to the at least one single-stranded arm by hybridizing the oligonucleotide linker portion of the at least one targeting agent/oligonucleotide linker to a complementary nucleotide sequence of the at least one single-stranded arm. In some embodiments, one, two, or three additional targeting agents are further conjugated to other single-stranded arms.

In general, the oligonucleotides can be synthesized using chemical techniques that do not employ synthetic enzymes (e.g., as in PCR) or in vivo replication (e.g., as in cloning and replicating the sequence in a microorganism). By way of example, the nucleic acids may be synthesized by solid-phase synthesis using the phosphoramidite method, with subsequent isolation of the products by HPLC or gel electrophoresis if necessary. The nucleic acids may be derived from 2'-deoxynucleosides, ribonucleosides, or chemically modified nucleosides (e.g., LNA or BNA).

In some embodiments, the single-stranded nucleic acid molecules may by synthesized using naturally-occurring or non-naturally occurring nucleosides. The chemically synthesized single-stranded nucleic acid molecules may be chemically synthesized using any of the known synthetic methods, including methods for solid-phase synthesis such as nucleoside phosphoramidite chemistry which uses cycles of deprotection, coupling, capping and stabilization to synthesize the desired nucleic acid molecule from the 3' to the 5' end, as is known in the art. For longer oligonucleotides it is generally recommended to purify the finished nucleic acid molecule after it is released from the solid phase, for example by polyacrylamide gel electrophoresis or high performance liquid chromatography (HPLC).

The present disclosure also provides methods of making the double monomer nucleic acid carriers described herein comprising: hybridizing the first oligonucleotide to the second oligonucleotide to form a first nucleic acid carrier; hybridizing the third oligonucleotide to the fourth oligonucleotide to form a second nucleic acid carrier; hybridizing one single-stranded arm of the first nucleic acid carrier to one single-stranded arm of the second nucleic acid carrier, forming a double monomer nucleic acid carrier comprising six single-stranded arms; and conjugating the at least one targeting agent to the at least one single-stranded arm. In some embodiments, the at least one targeting agent is further conjugated to an oligonucleotide linker prior to conjugating the at least one targeting agent to the at least one single-stranded arm. In some embodiments, the at least one targeting agent/oligonucleotide linker is conjugated to the at least one single-stranded arm by hybridizing the oligonucleotide linker portion of the at least one targeting agent/oligonucleotide linker to a complementary nucleotide sequence of the at least one single-stranded arm. In some embodiments, one, two, three, four, or five additional targeting agents are further conjugated to other single-stranded arms.

The present disclosure also provides methods of making the trimer nucleic acid carriers described herein comprising: hybridizing the first terminal arm of the second oligonucleotide to the first terminal arm of the first oligonucleotide; hybridizing the first terminal arm of the third oligonucleotide to the second terminal arm of the first oligonucleotide; conjugating the first targeting agent to the second terminal arm of the second oligonucleotide; and conjugating the second targeting agent to the second terminal arm of the third oligonucleotide. In some embodiments, each targeting agent is further conjugated to an oligonucleotide linker prior to conjugating the targeting agents to the terminal arms. In some embodiments, each targeting agent/oligonucleotide linker is conjugated to the terminal arm by hybridizing the oligonucleotide linker portion of the targeting agent/oligonucleotide linker to a complementary nucleotide sequence of the terminal arm.

The present disclosure also provides methods of making the nucleic acid carrier described herein comprising: conjugating the first targeting agent to the first terminal arm; and conjugating the second targeting agent to the second terminal arm. In some embodiments, each targeting agent is further conjugated to an oligonucleotide linker prior to conjugating the targeting agents to the terminal arms. In some embodiments, each targeting agent/oligonucleotide linker is conjugated to the terminal arm by hybridizing the oligonucleotide linker portion of the targeting agent/oligonucleotide linker to a complementary nucleotide sequence of the terminal arm.

All of the nucleic acid carriers described herein may be covalently cross-linked as described herein. The cross-linked monomers provide an advantage because it maintains the structural integrity of the assembled nucleic acids and improves the stability of the nucleic acid carriers. Such cross-linking was not previously possible for branched polynucleotide molecules constructed from chemically synthesized nucleic acids. Cross-links may be reversible or irreversible. In some embodiments, a plurality of monomers are cross-linked. Alternately, all of the monomer linkages can be cross-linked. In some embodiments, the double-stranded region within a single monomer is cross-linked. In some embodiments, the single-stranded arm of one monomer is cross-linked to the oligonucleotide conjugated to the targeting agent. In some embodiments, the double-stranded region of one monomer is cross-linked to the double-stranded region of another monomer. In some embodiments, the single-stranded arm of one monomer is cross-linked to a single-stranded arm of another monomer. Alternately, the double-stranded region of one monomer is cross-linked to a single-stranded arm of another monomer. Numerous agents are known for cross-linking and include, but are not limited to, mitomycin C and daunamycin, and other anticancer drugs that cross-link DNA, ethidium diazide, cisplatin, EDC-type compounds, and psoralens. A suitable cross-linking agent can be selected by persons skilled in the art based on the particular requirements of the cross-linker and the sequence of the nucleic acids involved. In some embodiments, psoralen is used as the cross-linking agent. Psoralen intercalates into the double helix of double-stranded DNA and readily forms covalent bonds with pyrimidine nucleotides upon irradiation with UV light. In addition to psoralen, the psoralen derivatives are useful for cross-linking the nucleic acids of the nucleic acid carriers. Psoralen derivatives include, but are not limited to, 8-methoxy psoralen, 4,5',8-trimethylpsoralen, and 4'-adducts of trioxsalen (e.g., 4'-hydroxymethyl-4,5', trimethyl psoralen, 4'-methoxymethyl-4,5',8-trimethyl psoralen, 4'N-phthalimidomethyl-4,5', 8-trimethyl psoralen, and 4'-aminomethyl-4,5'-,8trimethyl psoralen hydrochloride). Procedures for cross-linking with psoralens are standard and known in the art.

The nucleic acid carriers described herein are useful for drug delivery, diagnostics, and medical imaging, among other biotechnological applications.

The present disclosure also provides methods of inducing an immune response in an animal (suitably a mammal such as a human) comprising administering to the animal (suitably a mammal such as a human) any one or more of the nucleic acid carriers described herein, or a pharmaceutical composition comprising the nucleic acid carrier, wherein the nucleic acid carrier comprises at least two targeting agents chosen from an antigen, a peptide, an antibody or fragment thereof, and an adjuvant.

In some embodiments, the antigen is chosen from the bacterial or viral antigens described herein. In some embodiments, the antibody fragment is any of the antibody fragments described herein. In some embodiments, the antibody, or fragment thereof, is directed to a cell surface marker described herein. In some embodiments, the adjuvant is one or more of the adjuvants described herein. In some embodiments, the oligonucleotide linker conjugating the targeting moiety to the terminal arm is a CpG containing oligonucleotide comprising one or more CpG sequences.

The present disclosure also provides methods of treating an animal (suitably a mammal such as a human) having cancer comprising administering to the animal (suitably a mammal such as a human) a nucleic acid carrier of any one or more of the nucleic acid carriers described herein, or a pharmaceutical composition comprising the nucleic acid carrier, wherein the nucleic acid carrier comprises at least two targeting agents chosen from an antibody, or fragment thereof, and a label.

In some embodiments, the antibody fragment is any of the antibody fragments described herein. In some embodiments, a first antibody, or fragment thereof, is directed to a tumor-associated antigen. In some embodiments, the tumor-associated antigen is any of the tumor-associated antigens described herein. In some embodiments, a second antibody, or fragment thereof, is directed to a cell surface marker. In some embodiments, the cell surface marker is any of the cell surface markers described herein. In some embodiments, the nucleic acid carrier comprises any one or more of: a first targeting agent which is an antibody, or fragment thereof, directed to HER2 and a second targeting agent which is an antibody, or fragment thereof, directed to CD64, and wherein the cancer is breast, ovarian, or prostrate; a first targeting agent which is an antibody, or fragment thereof, directed to EGFR and a second targeting agent which is an antibody, or fragment thereof, directed to CD64, and wherein the cancer is a solid tumor, lung, or colorectal; a first targeting agent which is an antibody, or fragment thereof, directed to EGFR and a second targeting agent which is an antibody, or fragment thereof, directed to PD-1, and wherein the cancer is triple negative breast cancer; a first targeting agent which is an antibody, or fragment thereof, directed to PD-L1 and a second targeting agent which is an antibody, or fragment thereof, directed to OX-40, and wherein the cancer is breast cancer; a first targeting agent which is an antibody, or fragment thereof, directed to CD30 and a second targeting agent which is an antibody, or fragment thereof, directed to CD16, and wherein the cancer is Hodgkin's disease; a first targeting agent which is an antibody, or fragment thereof, directed to HER2 and a second targeting agent which is an antibody, or fragment thereof, directed to CD3, and wherein the cancer is metastatic breast cancer or prostrate; a first targeting agent which is an antibody, or fragment thereof, directed to CD20 and a second targeting agent which is an antibody, or fragment thereof, directed to CD3, and wherein the cancer is non-Hodgkin lymphoma or multiple myeloma; a first targeting agent which is an antibody, or fragment thereof, directed to EpCAM and a second targeting agent which is an antibody, or fragment thereof, directed to CD3, and wherein the cancer is ovarian, gastric, colon, colorectal, breast, non-small cell lung cancer, adenocarcinoma of the lung, small cell lung cancer; a first targeting agent which is an antibody, or fragment thereof, directed to NG2 and a second targeting agent which is an antibody, or fragment thereof, directed to CD28, and wherein the cancer is melanoma; a first targeting agent which is an antibody, or fragment thereof, directed to CD19 and a second targeting agent which is an antibody, or fragment thereof, directed to CD3, and wherein the cancer is B-precursor acute lymphoblastic leukemia or non-Hodgkin lymphoma; a first targeting agent which is an antibody, or fragment thereof, directed to CD19 and a second targeting agent which is an antibody, or fragment thereof, directed to CD16, and wherein the cancer is non-Hodgkin lymphoma; a first targeting agent which is an antibody, or fragment thereof, directed to CEA and a second targeting agent which is an antibody, or fragment thereof, directed to HSG, and wherein the cancer is colorectal, lung carcinoma, pancreas carcinoma, stomach carcinoma, ovary carcinoma, uterus carcinoma, breast carcinoma, or melanoma; a first targeting agent which is an antibody, or fragment thereof, directed to MUC-1 and a second targeting agent which is an antibody, or fragment thereof, directed to HSG, and wherein the cancer is invasive pancreatic adenocarcinoma; a first targeting agent which is an antibody, or fragment thereof, directed to CA19-9 and a second targeting agent which is an antibody, or fragment thereof, directed to CD3, and wherein the cancer is a CA19-9-positive tumor; a first targeting agent which is an antibody, or fragment thereof, directed to CEA and a second targeting agent which is an antibody, or fragment thereof, directed to CD3, and wherein the cancer is ovarian; a first targeting agent which is an antibody, or fragment thereof, directed to OCAA and a second targeting agent which is an antibody, or fragment thereof, directed to CD3, and wherein the cancer is ovarian; a first targeting agent which is an antibody, or fragment thereof, directed to MAPG and a second targeting agent which is an antibody, or fragment thereof, directed to CD28, and wherein the cancer is metastatic melanoma; a first targeting agent which is an antibody, or fragment thereof, directed to HER2 and a second targeting agent which is an antibody, or fragment thereof, directed to CD16, and wherein the cancer is a HER-2 positive tumor; a first targeting agent which is an antibody, or fragment thereof, directed to glioma and a second targeting agent which is an antibody, or fragment thereof, directed to CD3, and wherein the cancer is a glioma; and a first targeting agent which is folic acid or folic acid receptor and a second targeting agent which is an antibody, or fragment thereof, directed to CD3 or CD16, and wherein the cancer is small cell lung carcinoma, breast, or ovarian.

In some embodiments, the nucleic acid carrier comprises any one or more of: a first targeting agent which is an antibody, or fragment thereof, directed to a disease-associated marker, a second targeting agent which is an antibody directed to a cell surface marker, and a third targeting agent which is an antibody, or fragment thereof, directed to a second cell surface marker, and wherein the disease is a cancer.

In some embodiments, the nucleic acid carrier comprises any one or more of: a first targeting agent which is an antigen associated with a disease, a second targeting agent which is an antibody directed to a cell surface marker, and a third targeting agent which is an adjuvant, and wherein the indication is a vaccine.

In some embodiments, the label is a chemiluminescent agent, a fluorescent agent, an infrared dye, a radiolabel agent, a metal, a chelating agent, a hapten, or a gene or mRNA encoding a detectable protein. In some embodiments, the presence of the label is used to track the location of the nucleic acid carrier.

The present disclosure also provides methods of treating an animal (suitably a mammal such as a human) having a disease associated with a disease-associated antigen comprising administering to the animal (suitably a mammal such as a human) a nucleic acid carrier of any one or more of the nucleic acid carriers described herein, or a pharmaceutical composition comprising the nucleic acid carrier, wherein the nucleic acid carrier comprises at least two targeting agents chosen from an antibody, or fragment thereof, and a label.

In some embodiments, the antibody fragment is any of the antibody fragments described herein. In some embodiments, a first antibody, or fragment thereof, is directed to a disease-associated antigen. In some embodiments, the disease-associated antigen is any of the disease-associated antigens described herein. In some embodiments, a second antibody, or fragment thereof, is directed to a cell surface marker. In some embodiments, the cell surface marker is any of the cell surface markers described herein. In some embodiments, the label is a chemiluminescent agent, a fluorescent agent, an infrared dye, a radiolabel agent, a metal, a chelating agent, a hapten, or a gene or mRNA encoding a detectable protein. In some embodiments, the presence of the label is used to track the location of the nucleic acid carrier.

In any of the embodiments described herein wherein a portion of one molecule is designed to have a nucleotide sequence that is complementary to the nucleotide sequence of another molecule, the complementarity need not be 100%. In some embodiments, the two nucleotide sequences are 100% complementary. A nucleotide sequence is "complementary" to another nucleotide sequence when it is capable of base-pairing with the oligonucleotide according to the standard Watson-Crick, Hoogsteen or reverse Hoogsteen binding complementarity rules. In some embodiments, the terms "complementary" and "complement(s)" refer to an oligonucleotide or sequence thereof comprising a sequence of consecutive nucleotides or semi-consecutive nucleotides (e.g., one or more nucleotide moieties are not present in the molecule) capable of hybridizing to another nucleic acid molecule that may be consecutive, semi-consecutive or non-consecutive nucleotides even if less than all the nucleotides base pair with a counterpart nucleotide. In some embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%, and any range derivable therein, of the nucleotide sequence is capable of base-pairing with another nucleotide sequence during hybridization. In some embodiments, the term "complementary" refers to a nucleotide sequence that may hybridize to another nucleotide sequence under stringent conditions, as would be understood by one of ordinary skill in the art. In some embodiments, the nucleotide sequence may be "partly complementary" to another nucleotide sequence, and may hybridize in low stringency conditions, or contains a sequence in which less than about 70% of the nucleotide sequence is capable of base-pairing with another nucleotide sequence.

In some embodiments, the animal is a bird, reptile, amphibian, or mammal, which can be a mouse, rat, other rodent, rabbit, dog, cat, swine, cattle, sheep, horse, or primate, such as a human. In some embodiments, the animal is a human.

In some embodiments, the animal or mammal being treated is "in need thereof," which means that the animal or mammal (suitably a human) has been identified as having a need for the particular method of treatment. In some embodiments, the identification can be by any means of diagnosis. In any of the methods and treatments described herein, the animal or mammal (suitably a human) can be in need thereof.

In some embodiments, a "therapeutically effective amount" of the nucleic acid carrier is administered to the animal or mammal (suitably a human). A "therapeutically effective amount" means the amount that elicits the biological or medicinal response that is being sought in a tissue, system, animal, mammal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the animal or mammal. Optimal amounts can also be determined based on monitoring of the animal's or mammal's response to treatment. Beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment.

The precise dose to be employed in the compositions will also depend on the route of administration, and the seriousness of the disorder or disease, and should be decided according to the judgment of the practitioner and each animal's or mammal's circumstances. However, a suitable dosage range for oral administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight. In some embodiments, a suitable dosage range for oral administration is, generally, from about 0.1 mg to about 500 mg, from about 1 mg to about 100 mg, from about 10 mg to about 50 mg, or from about 10 mg to about 25 mg.

In some embodiments, suitable dosage ranges for intravenous (i.v.) administration are from about 0.01 mg to about 500 mg per kg body weight, from about 0.1 mg to about 100 mg per kg body weight, from about 1 mg to about 50 mg per kg body weight, or from about 10 mg to about 35 mg per kg body weight. In some embodiments, a suitable dosage range for i.v. administration is, generally, from about 0.1 mg to about 500 mg, from about 1 mg to about 100 mg, from about 10 mg to about 50 mg, or from about 10 mg to about 25 mg. Suitable dosage ranges for other modes of administration can be calculated based on the forgoing dosages as known by those skilled in the art. For example, recommended dosages for intradermal, intramuscular, intraperitoneal, subcutaneous, epidural, sublingual, intracerebral, intravaginal, transdermal administration or administration by inhalation are in the range of from about 0.001 mg to about 200 mg per kg of body weight, from about 0.01 mg to about 100 mg per kg of body weight, from about 0.1 mg to about 50 mg per kg of body weight, or from about 1 mg to about 20 mg per kg of body weight. Effective doses may be extrapolated from dose-response curves derived from in vitro or animal model test systems. Such animal models and systems are well known in the art.

The nucleic acid carriers described herein can be formulated for parenteral administration by injection, such as by bolus injection or continuous infusion. The nucleic acid carriers can be administered by continuous infusion subcutaneously over a period of about 15 minutes to about 24 hours. Formulations for injection can be presented in unit dosage form, such as in ampoules or in multi-dose containers, with an added preservative. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the nucleic acid carriers described herein can be formulated by combining the nucleic acid carriers with pharmaceutically acceptable carriers well known in the art. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by an animal or mammal to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Oral compositions can include standard vehicles such as mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

For administration by inhalation, the nucleic acid carriers described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. Capsules and cartridges of, such as gelatin for use in an inhaler or insufflator can be formulated containing a powder mix of the nucleic acid carriers and a suitable powder base such as lactose or starch.

The nucleic acid carriers described herein can also be formulated in rectal compositions such as suppositories or retention enemas, such as containing conventional suppository bases such as cocoa butter or other glycerides. The nucleic acid carriers described herein can also be formulated in vaginal compositions such as vaginal creams, suppositories, pessaries, vaginal rings, and intrauterine devices.

In transdermal administration, the nucleic acid carriers can be applied to a plaster, or can be applied by transdermal, therapeutic systems that are consequently supplied to the organism. In some embodiments, the nucleic acid carriers are present in creams, solutions, powders, fluid emulsions, fluid suspensions, semi-solids, ointments, pastes, gels, jellies, and foams, or in patches containing any of the same.

The nucleic acid carriers described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the nucleic acid carriers can be formulated with suitable polymeric or hydrophobic materials (for example as an emulsion in an acceptable oil) or ion exchange resins, or as sparingly soluble derivatives, for example, as a sparingly soluble salt.

In some embodiments, the nucleic acid carriers can be delivered in a controlled release system. In some embodiments, a pump may be used. In another embodiment, polymeric materials can be used. In some embodiments, a controlled-release system can be placed in proximity of the target of the nucleic acid carriers described herein, such as the liver, thus requiring only a fraction of the systemic dose.

The nucleic acid carriers can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol).

In some embodiments, the nucleic acid carriers described herein can be delivered in a vesicle, in particular a liposome.

In some embodiments, the formulation can be lyophilized to a solid and reconstituted with, for example, water prior to use.

When administered to a human, the nucleic acid carriers can be in a sterile vehicle. Water is a suitable carrier when the compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use.

The pharmaceutical compositions can be in unit dosage form. In such form, the composition can be divided into unit doses containing appropriate quantities of the nucleic acid carriers. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfite, acetylcysteine, polyquaternium-1, benzalkonium chloride, thimerosal, chlorobutanol, methyl paraben, propyl paraben, phenylethyl alcohol, edetate disodium, sorbic acid, a tocopherol, a tocotrienol, or other agents know to those of skill in the art. Such preservatives are typically employed at a level of from about 0.001% to about 1.0% by weight.

In some embodiments, the nucleic acid carriers are solubilized at least in part by an acceptable solubilizing agent. Certain acceptable nonionic surfactants, for example polysorbate 80, can be useful as solubilizing agents, as can acceptable glycols, polyglycols, e.g., polyethylene glycol 400 (PEG-400), and glycol ethers. Suitable solubilizing agents for solution and solution/suspension compositions are cyclodextrins. Suitable cyclodextrins can be chosen from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like. An acceptable cyclodextrin can optionally be present in a composition at a concentration from about 1 to about 200 mg/ml, from about 5 to about 100 mg/ml, or from about 10 to about 50 mg/ml.

In some embodiments, the composition optionally contains a suspending agent. For example, in those embodiments in which the composition is an aqueous suspension or solution/suspension, the composition can contain one or more polymers as suspending agents. Useful polymers include, but are not limited to, water-soluble polymers such as cellulosic polymers, for example, hydroxypropyl methylcellulose, and water-insoluble polymers such as cross-linked carboxyl-containing polymers. However, in some embodiments, compositions do not contain substantial amounts of solid particulate matter, whether of the antimicrobial polymer or oligomer active agent, an excipient, or both, as solid particulate matter, if present, can cause discomfort and/or irritation of a treated eye.

One or more acceptable pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Optionally one or more acceptable surfactants, preferably nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, F84 and P-103); cyclodextrin; or other agents known to those of skill in the art. Typically, such co-solvents or surfactants are employed in the compositions at a level of from about 0.01% to about 2% by weight.

In some embodiments, pharmaceutical packs or kits comprising one or more containers filled with one or more of the nucleic acid carriers are provided herein. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one nucleic acid carrier described herein. In some embodiments, the kit comprises a nucleic acid carrier described herein and optionally another therapeutic agent. In some embodiments, the kit contains an injectable device such as a syringe with a needle.

The nucleic acid carriers described herein may have numerous benefits including, but not limited to, improved flexibility, improved efficacy, enhanced immunity, less toxicity, improved solubility of hydrophobic targeting agents and drugs, and improved half-life, circulation time, clearance, and PK profile.

The nucleic acid carriers described herein are highly modular in both design and construction as well as in final formulation when combining various targeting agents to achieve a desired outcome. Individual components, nucleic acid carriers scaffold of varying design, and individual targeting agents conjugated to linker sequences that bind to the arms of the nucleic acid carriers, can be separately prepared and characterized. The individually characterized components and targets can be mixed and matched at varying desired ratios prior to testing in vitro or in vivo using the linker oligonucleotides to couple particular components to the scaffold. Combining more than one of the same targeting agent alters both the specificity and avidity of the nucleic acid carrier formulation to the disease or cellular target. This ability to fine tune a nucleic acid carrier is an advantage over bi- or tri-specific antibodies or fusion proteins because bi- or tri-specific antibodies or fusion proteins are limited to only one or sometimes two valences for a particular target. Also, many of the bi- and tri-specific constructs, especially those used in immune oncology programs, have proven to be challenging to manufacture in clinically relevant quantities and a wide variety of formats have been used, including diabodies, tandem scFv, cross-linked antigen binding fragments (Fab) and quadroma-derived constructs. It would be more advantageous to use the original whole antibody clone to produce bi-, tri-, or multi-specific combinations rather than having to generate new genetic or fusion constructs and repeat the extensive characterization process. Coupling the original antibody clone to a linker oligonucleotide to introduce the antibody clone into a nucleic acid carrier and proceeding into formulation is a quicker and less costly process.

The nucleic acid carriers described herein may possess improved efficacy for several reasons. The nucleic acid carriers have a higher target capacity for targeting and payload (drug delivery). Control of positioning of immune cells relative to disease cells in immune oncology applications to facilitate more efficient immune cell based responses is also an advantage. The nucleic acid carrier scaffold also has a diameter that can be modulated and adjusted to maximize both the cell to cell positioning, distance between cells, and also provide for more stable binding between partner cells. For immune oncology, the nucleic acid carriers may possess more efficient binding and recruitment of immune cells and targeting to the tumor because of the multivalence to both tumor and immune cells as compare to other bi- and tri-specific constructs that only have one or two binding sites for immune and disease cells. Nanoparticle-mediated targeting of adjuvants to lymph nodes in vaccination increases both efficacy and safety, both by blocking systemic distribution of the adjuvant and by permitting significant dose-sparing (up to 250-fold). In addition, targeted delivery of TLR ligands in nanoparticles to dendritic cells has also been shown to strongly enhance the potency of the delivery adjuvant.

The nucleic acid carriers described herein may also possess enhanced adaptive (humoral) immunity for vaccine development and immune oncology applications. The multivalent structure of the nucleic acid carriers lends adaptability to include immune cell targeting molecules, one or more antigens (the same or different), and one or more adjuvants (the same or different). For example combining mannose and TLR agonists as part of one multivalent nucleic acid carriers allows for synergistic enhancement of long term humoral immune responses. This trend should continue for the foreseeable future as many classes of new materials have yet to be studied in depth and may have great potential in this field. Examples include DNA nanostructures that can present complex, three-dimensional multivalent motifs to engage and organize immune cell receptors. The nucleic acid carriers can simultaneously target specific antigen presenting cells (such as dendritic cells) while delivering one or more of the same or different adjuvants, and antigens. The nucleic acid carriers possess active targeting through conjugation of ligands for cell-surface receptors, which can often increase the uptake of nanoparticles by phagocytic cells relative to non-targeted particles, making macrophages and monocytes suitable targets for the nucleic acid carriers to deliver immunoregulatory drugs. Numerous receptors allow macrophage-specific targeting, including the Fc receptor, scavenger receptors, and mannose receptors (MMR or CD206). Targeting the macrophage Fc receptor is achieved by coating nanoparticles with IgG, which accelerates uptake of particles and enhances their retention within macrophages. The macrophage mannose receptor (MMR) is expressed on mature macrophages and dendritic cells but not on monocytes in the blood circulation. By combining both of these targeting strategies onto one nucleic acid carrier, particle enhanced presentation of antigens and amplified immune activation properties can be achieved. The nucleic acid carriers may also possess improved delivery and presentation of MHC I antigens into the cytosol. In addition, the flexibly of the nucleic acid carrier to be easily adapted into different sizes as well as flexibly of the scaffold materials to bend, compress and change positioning allows for a more efficient uptake by the lymphatic system. This feature has been consistently linked to improved performance for immune response and reduction of system cytokine associated toxicity.

The nucleic acid carriers described herein may also possess less toxicity compared to the same targeting agents in the absence of the nucleic acid carriers. By sequestering potentially toxic materials (drugs, antibodies and other molecules) as part of the formulation until it reaches the destination, the nucleic acid carriers may prevent off target accumulation and side effects. These materials can include the targeting antibodies or portions thereof, antigens of cytotoxic drugs, or molecules to be delivered at the same time as the nanoparticle with all targeting molecules. Also, the change in biodistribution of loaded cargo (i.e., drugs) and targeting antibodies, drugs as a function of the unique properties of the nucleic acid carriers (charge, size, shape, targeting molecule density, etc.) may limit the off target exposure as well as result in a different, less toxic clearance of the cargo not reaching the disease target.

The nucleic acid carriers described herein may also possess improved solubility of hydrophobic targeting agents and drugs. Many classes of drugs, small molecules, and biologics have been linked to poor solubility when delivered as singular compounds, often reducing their circulation time or ability to reach a desired target. However, the nucleic acid carrier scaffold is highly negatively charged and once a drug is linked, it improves the ability to deliver the drug to target destination in an aqueous environment. The chemistry, composition, and negative charge of the nucleic acid carrier scaffold may reconfigure the biologically presented properties of targeting agents and drugs once attached.

The nucleic acid carriers described herein may also possess improved half-life, circulation time, clearance, and PK profile. Once attached to the nucleic acid carrier scaffold, small drugs can be redirected away from the normally observed kidney clearance, resulting in an increases in the overall circulation half-life and an increase in the PK of the drug. For example, Doxorubicin, a small drug less than 1 kDa molecular weight, is cleared through glomerular filtration in the kidney and has a half-life measured in minutes. When attached to a nucleic acid carrier, however, the new half-life is measured in hours.

The nucleic acid carriers described herein may also possess the improved ability to transport drug cargo across the blood-brain barrier. Thus, the nucleic acid carriers described herein may be used as a delivery vehicle for active ingredients that are normally not transported across the blood-brain barrier. Accordingly, various types of diseases and disorders associated with the brain may be treated by delivery of drugs across the blood-brain barrier including, for example, neurological disorders and cancers of the brain (i.e., glioblastoma, and medulloblastoma).

The following representative embodiments are presented:

Embodiment 1. A nucleic acid carrier comprising:
    a first and a second oligonucleotide;
        wherein a central portion of each of the first and second oligonucleotides is complementary to each other, forming a double-stranded region,
        wherein the two terminal portions of the first oligonucleotide are not complementary to the two terminal portions of the second oligonucleotide, forming four single-stranded arms; and
    at least one targeting agent conjugated to at least one single-stranded arm.

Embodiment 2. The nucleic acid carrier of embodiment 1, wherein the nucleic acid is deoxyribonucleic acid (DNA), ribonucleic acid (RNA), modified DNA or RNA, or a combination thereof.

Embodiment 3. The nucleic acid carrier of embodiment 1 or 2, wherein the double-stranded region is 4 to 2000 bases in length.

Embodiment 4. The nucleic acid carrier of embodiment 3, wherein the double-stranded region is 5 to 200 bases in length.

Embodiment 5. The nucleic acid carrier of embodiment 4, wherein the double-stranded region is 25 to 50 bases in length.

Embodiment 6. The nucleic acid carrier of any one of embodiments 1 to 5, wherein each single-stranded arm is 4 to 200 bases in length.

Embodiment 7. The nucleic acid carrier of embodiment 6, wherein each single-stranded arm is 5 to 50 bases in length.

Embodiment 8. The nucleic acid carrier of embodiment 7, wherein each single-stranded arm is 25 to 50 bases in length.

Embodiment 9. The nucleic acid carrier of embodiment 8, wherein each single-stranded arm is 16 to 50 bases in length.

Embodiment 10. The nucleic acid carrier of any one of embodiments 1 to 9, wherein the nucleotide sequence of each of the four single-stranded arms is identical.

Embodiment 11. The nucleic acid carrier of any one of embodiments 1 to 9, wherein the nucleotide sequences of three of the single-stranded arms are identical to each other and different than the nucleotide sequence of the fourth single-stranded arm.

Embodiment 12. The nucleic acid carrier of any one of embodiments 1 to 9, wherein the nucleotide sequences of two of the single-stranded arms are identical to each other and different than the nucleotide sequences of the other two single-stranded arms.

Embodiment 13. The nucleic acid carrier of any one of embodiments 1 to 9, wherein the nucleotide sequences of two of the single-stranded arms are identical to each other and the nucleotide sequences of the other two single-stranded arms are identical to each other, wherein the nucleotide sequence of the first two single-stranded arms is different than the nucleotide sequences of the second two single-stranded arms.

Embodiment 14. The nucleic acid carrier of any one of embodiments 1 to 9, wherein the nucleotide sequence of each of the four single-stranded arms is different.

Embodiment 15. The nucleic acid carrier of any one of embodiments 1 to 4, wherein the at least one targeting agent is conjugated to the at least one single-stranded arm by an oligonucleotide linker.

Embodiment 16. The nucleic acid carrier of embodiment 15, wherein a single targeting agent is conjugated to a single-stranded arm.

Embodiment 17. The nucleic acid carrier of embodiment 15, wherein a first targeting agent is conjugated to one single-stranded arm and a second targeting agent is conjugated to a different single-stranded arm.

Embodiment 18. The nucleic acid carrier of embodiment 17, wherein the first targeting agent is identical to the second targeting agent.

Embodiment 19. The nucleic acid carrier of embodiment 17, wherein the first targeting agent is different than the second targeting agent.

Embodiment 20. The nucleic acid carrier of embodiment 15, wherein a first targeting agent is conjugated to one single-stranded arm, a second targeting agent is conjugated to a different single-stranded arm, and a third targeting agent is conjugated to a different single-stranded arm.

Embodiment 21. The nucleic acid carrier of embodiment 20, wherein the first targeting agent, the second targeting agent, and the third targeting agent are identical.

Embodiment 22. The nucleic acid carrier of embodiment 20, wherein the first and second targeting agents are identical and the third targeting agent is different than the first and second targeting agents.

Embodiment 23. The nucleic acid carrier of embodiment 20, wherein the first targeting agent, the second targeting agent, and the third targeting agent are different.

Embodiment 24. The nucleic acid carrier of any one of embodiments 1 to 23, wherein one or more single-stranded arms not conjugated to a targeting agent is complementary base paired to an oligonucleotide linker.

Embodiment 25. The nucleic acid carrier of embodiment 15, wherein a first targeting agent is conjugated to one single-stranded arm, a second targeting agent is conjugated to a different single-stranded arm, a third targeting agent is conjugated to a different single-stranded arm, and a fourth targeting agent is conjugated to a different single-stranded arm.

Embodiment 26. The nucleic acid carrier of embodiment 25, wherein the first targeting agent, the second targeting agent, the third targeting agent, and the fourth targeting agent are identical.

Embodiment 27. The nucleic acid carrier of embodiment 25, wherein the first targeting agent, the second targeting agent, and the third targeting agent are identical and the fourth targeting agent is different.

Embodiment 28. The nucleic acid carrier of embodiment 25, wherein the first targeting agent and the second targeting agent are identical, and the third targeting agent and the fourth targeting agent are identical, wherein the first and second targeting agents are different than the third and fourth targeting agents.

Embodiment 29. The nucleic acid carrier of embodiment 25, wherein the first targeting agent and the second targeting agent are identical, and the third targeting agent and the fourth targeting agent are each different.

Embodiment 30. The nucleic acid carrier of embodiment 25, wherein the first targeting agent, the second targeting agent, the third targeting agent, and the fourth targeting agent are each different.

Embodiment 31. The nucleic acid carrier of any one of embodiments 1 to 30, wherein the at least one targeting agent is an antigen, a peptide, an antibody or fragment thereof, an antibody-drug conjugate, a non-antibody scaffold, a label, an adjuvant, an RNA molecule, a DNA molecule, a vitamin, a protein, a fusion protein, a fusion peptide, a carbohydrate, a lipid, a polysaccharide, a lipopolysaccharide, a polymer, a virus particle, or a virus-like particle, or any combination thereof.

Embodiment 32. The nucleic acid carrier of embodiment 31, wherein the polymer is hyaluronic acid, polyargenine, polylysine, polyethylenimine (PEI), polyethyleglycol (PEG), polyglycolic acid (PGA), polylactic acid (PLA), or poly(lactic-co-glycolic acid) (PLGA).

Embodiment 33. The nucleic acid carrier of embodiment 31, wherein the non-antibody scaffold is an affibody, an affilin, an anticalin, an atrimer, an avimer, a bicyclic peptide, a cys-knot, a DARPin, an FN3, a fynomer, a kunitz domain, or an O-body.

Embodiment 34. The nucleic acid carrier of embodiment 31, wherein the antigen is a bacterial antigen, a viral antigen, a fungal antigen, a yeast antigen, a protozoan antigen, or prion.

Embodiment 35. The nucleic acid carrier of embodiment 34, wherein the antigen is from *Acetobacter aurantius, Acinetobacter baumannii, Acinetobacter calcoaceticus, Acinetobacter haemolyticus, Acinetobacter junii, Acinetobacter lwoffii, Actinomyces israelii, Actinomyces viscosus, Aggregatibacter actinomycetemcomitans, Agrobacterium radiobacter, Agrobacterium tumefaciens, Azorhizobium caulinodans, Azotobacter vinelandii, Anaplasma phagocytophilum, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides gingivalis, Bacteroides fragilis, Bacteroides melaninogenicus (Prevotella melaninogenica), Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae (Chlamydia pneumoniae), Chlamydophila psittaci (Chlamydia psittaci), Citrobacter freundii, Citrobacter diverus, Citrobacter koseri, Clostridium botulinum, Clostridium difficile, Clostridium perfringens (Clostridium welchii), Clostridium tetani, Corynebacterium diphtheria, Corynebacterium fusiforme, Coxiella burnetii, Ehrlichia chaffeensis, Enterobacter aerogenes, Enterobacter cloacae, Enterobacter faecalis, Enterococcus avium, Enterococcus durans, Enterococcus faecalis, Enterococcus faecium, Enterococcus galllinarum, Enterococcus maloratus, Eschericia coli, Francisella tularensis, Fusobacterium nucleatum, Gardnerella vaginalis, Haemophilus ducreyi, Haemophilus parainfluenzae, Haemophilus pertussis, Haemophilus vaginalis, Haemophilus influenza, Haemophilus aegyptius, Helicobacter pylori, Klebsiella pneumonia, Klebsiella oxytoca, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella lacunata, Moraxella catarrhalis, Morganella morganii, Mycobacterium avium, Mycobacterium africanum, Mycobacterium bovis, Mycobacterium canetti, Mycobacterium diphtheria, Mycobacterium intracellulare, Mycobacterium leprae, Mycobacterium lepraemurium, Mycobacterium microti, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumonia, Neisseria gonorrhoeae, Neisseria meningitides, Pasteurella multocida, Pasteurella tularensis, Porphyromonas gingivalis, Prevotella melaninogenica (Bacteroides melaninogenicus), Propionibacterium acnes, Proteus mirabillis, Proteus vulgaris, Providencia stuartii, Pseudomonas aeruginosa, Pseudomonas otitidis, Rhizobium radiobacter, Rickettsia prowazekii, Rickettsia psittaci, Rickettsia quintana, Rickettsia rickettsia, Rickettsia trachomae, Rochalimaea henselae, Rochalimaea Quintana, Rothia dentocariosa, Salmonella enteritidis, Salmonella typhi, Salmonella typhimurium, Serratia marcescens, Shigella dysenteriae, Staphylococcus aureus,* methicillin-resistant *Staphylococcus aureus, Staphylococcus pneumoniae, Staphylococcus epidermidis, Staphylococcus saprophyticus, Staphylococcus colmii, Staphylococcus sciuri, Staphylococcus warneri, Stenotrophomonas*

*maltophilia, Streptococcus agalactiae, Streptococcus anginosus, Streptococcus avium, Streptococcus bovis, Streptococcus cricetus, Streptococcus faceium, Streptococcus faecalis, Streptococcus ferus, Streptococcus gallinarum, Streptococcus lactis. Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Streptococcus viridans, Treponema pallidum, Treponema denticola, Vibrio cholera, Vibrio comma, Vibrio parahaemolyticus, Vibrio vulnificus, Wolbachia, Yersinia enterocolitica, Yersinia pestis, Yersinia pseudotuberculosis, Aspergillus fumigatus, Aspergillus flavus, Aspergillus clavatus, Aspergillus niger, Aspergillus terreus, Candida albicans, Candida glabrata, Candida tropicalis, Candida krusei, Candida dubliniensis, Candida parapsilosis, Fusarium solani, Fusarium moniliforme, Fusarium proliferartum, Malessezia pachydermatis, Chrysosporium parvum, Metarhizium anisopliae, Phaeoisaria clematidis,* or *Sarcopodium oculorum.*

Embodiment 36. The nucleic acid carrier of embodiment 32, wherein the antigen is from *Mycobacterium tuberculosis,* Varicella zoster virus, *Corynebacterium diphtheria,* Hepatitis A virus, Hepatitis B virus, Hepatitis C virus, Haemophilis influenza, Human Papillomavirus, Influenza virus, Japanese Encephalitis virus, Measles virus, *Neisseria meningitidis, Mumps virus, Bordetella pertussis, Streptococcus pneumonia,* Poliovirus, Rabies virus, Rotavirus, Rubella virus, Herpes Zoster virus, *Clostridium tetani, Salmonella typhi,* Yellow Fever virus, Ebola virus, avian flu virus, *Bacillus anthracis,* Smallpox virus, or Zika virus.

Embodiment 37. The nucleic acid carrier of embodiment 31, wherein the antibody fragment is Fab, F(ab')$_2$, scFv, tandem scFv, a BiTE, single domain (sdAb) antibody, diabody, single chain diabody, minibody, fusion protein, or scFv-Fc.

Embodiment 38. The nucleic acid carrier of embodiment 31, wherein the antibody, or fragment thereof, is directed to a disease-associated antigen.

Embodiment 39. The nucleic acid carrier of embodiment 38, wherein the disease-associated antigen is a tumor-associated antigen.

Embodiment 40. The nucleic acid carrier of embodiment 39, wherein the tumor-associated antigen is 4-1BB, 5AC, 5T4, A2aR, activin receptor-like kinase 1, AGS-22M6, AKAP4, alpha-fetoprotein, angiopoietin 2, B7-H3, BAFF, BAGE, BCR-ABL, BORIS, CA-125, CA19-9, C242 antigen, carbonic anhydrase 9 (CA-IX), CCR4, CD19, CD20, CD22, CD23 (IgE receptor), CD24, CD28, CD30 (TNFRSF8), CD33, CD37, CD38 (cyclic ADP ribose hydrolase), CD40, CD44 v6, CD51, CD56, CD70, CD71, CD73, CD74, CD79B, CD80, CD137, CD140a, CD152, CD200, CD221, CD274, CEA, ch4D5, CLDN18.2, CS1, CSFIR, CTLA-4, C-X-C chemokine receptor type 4, DLL4, DR5, EBAG9, EGF, EGFR, EGFL7, EpCAM, ERBB2, ERBB3, FAP, fibronectin extra domain-B, folate receptor 1, folate receptor alpha, folate hydrolase, Frizzled receptor, GAGE, GD2 ganglioside, GD3 ganglioside, glioma, glypican 3, GPNMB, gp100, GUCY2C, HER1, HER2/neu, HER3, HGF, HHGFR, histone complex, HLA-DR, human scatter factor receptor kinase, HPV-16, HSP105, IDH1, IDO1, IGF-I, IGF-1 receptor, ILGF2, IL-6, IL-13, integrin αvβ3, integrin α5β1, KIR, LAG-3, Lewis-Y antigen, LY6K, MAGE-1, MAGE-A3, MAGE-C2, MAGE-D4, MAPG, MART-1, Melan-A, MET, MCP-1, mesothelin, MIF, MSLN, MS4A1, mucin CanAg, MUC1, MUC4, MUC16, NG2, N-glycolylneuraminic acid, Notch receptor PD-1, NY-ESO-1, OCAA, PAP, PDGF-R α, PDCD1, PD1, PD-L1, phosphate-sodium co-transporter, phosphatidylserine, PRAME, PSA, RANKL, RON, ROR1, SDC1, Sialyl-Tn, SLAMF7, SPAG-9, SSX1, STEAP1, survivin, TAG-72, telomerase, TEM1, tenascin C, TGF-β, TIM-3, TLR, TAM, TIM-3, TRAIL-R2, TRAIL-R1, TWEAK receptor, tumor specific glycosylation of MUC1, tumor-associated calcium signal transducer 2, tumor antigen CTAA16.88, TYRP1 (glycoprotein 75), VEGF-A, VEGFR2, VEGFR-1, vimentin, VISTA, WT1, or XAGE-1b.

Embodiment 41. The nucleic acid carrier of embodiment 39, wherein the tumor-associated antigen is HER-2, EGFR, CD30, CD20, EpCAM, NG2, CD19, CEA, MUC-1, CA19-9, OCAA, MAPG, TAM, TLR, CD71, ERBB2, VEGF, or glioma.

Embodiment 42. The nucleic acid carrier of embodiment 38, wherein the disease-associated antigen is 1-40-β-amyloid, AOC3 (VAP-1), ACVR2B, angiopoietin 3, beta-amyloid, C5, CCL11 (eotaxin-1), CCR5, CD2, CD3, CD4, CD5, CD11, CD18, CD20, CD23 (IgE receptor), CD25 (a chain of IL-2 receptor), CD28, CD41 (integrin alpha-IIb), CD52, CD125, CD147 (basigin), CD154 (CD40L), CEA-related antigen, clumping factor A, endotoxin, GMCSF receptor α-chain, growth differentiation factor 8, hemagglutinin, HNGF, Hsp90, IGHE, IgE Fc region, IL-1β, IL-4, IL-5, IL-6, IL-9, IL-12, IL-13, IL-17, IL-17A, IL-20, IL-22, IL-23, IL-6 receptor, integrin α4β7, integrin α7B7, integrin α4, integrin αIIbβ3, interferon α/β receptor, interferon gamma-induced protein, IFN-γ, IFN-α, ITGB2 (CD18), LFA-1 (CD11a), LINGO-1, lipoteichoic acid, LOXL2, myelin-associated glycoprotein, myostatin, neural apoptosis-regulated proteinase 1, NGF, NOGO-A, *Oryctolagus cuniculus,* OX-40, PCSK9, phosphatidylserine, platelet-derived growth factor receptor beta, RANKL, Rhesus factor, sclerostin, SOST, sphingosine-1-phosphate, TFPI, TGF-β, TGF beta 2, TGF beta 1, TNF-α, VEGF-A, or VWF.

Embodiment 43. The nucleic acid carrier of embodiment 31, wherein the antibody, or fragment thereof, is directed to a cell surface marker.

Embodiment 44. The nucleic acid carrier of embodiment 43, wherein the cell surface marker is on an immune cell.

Embodiment 45. The nucleic acid carrier of embodiment 44, wherein the immune cell is a T cell, B cell, NK cell, macrophage, TIL, dendritic cell, neutrophil, eosinophil, basophil, or mast cell.

Embodiment 46. The nucleic acid carrier of embodiment 45, wherein the T cell is a CD4$^+$ T cell, CD8$^+$ T cell, helper T cell, cytotoxic T cell, or natural killer T cell; and wherein the B cell is a memory B cell or a plasma cell.

Embodiment 47. The nucleic acid carrier of embodiment 43, wherein the cell surface marker is CD36, CD68, CD83, CD180, CD206 (MRC1-mannose receptor), F4/80 (EGF-TM7 family), CD205, CD56, CD161, CD94:NKG2 heterodimer, KIR/CD158 family, CD335, CD64, CD16, CD3, CD28, CD4, CD25, CD39, Toll-like receptors (TLRs), CD281, CD283, CD284, CD286, CD289, CD282, C-type lectin receptors (CLRs), Fc Receptor, or HSG.

Embodiment 48. The nucleic acid carrier of embodiment 31, comprising one or two of the following:
 a first targeting agent which is an antibody, or fragment thereof, directed to HER2 and a second targeting agent which is an antibody, or fragment thereof, directed to CD64;
 a first targeting agent which is an antibody, or fragment thereof, directed to EGFR and a second targeting agent which is an antibody, or fragment thereof, directed to CD64;

a first targeting agent which is an antibody, or fragment thereof, directed to EGFR and a second targeting agent which is an antibody, or fragment thereof, directed to PD-1;

a first targeting agent which is an antibody, or fragment thereof, directed to PD-L1 and a second targeting agent which is an antibody, or fragment thereof, directed to OX40;

a first targeting agent which is an antibody, or fragment thereof, directed to CD30 and a second targeting agent which is an antibody, or fragment thereof, directed to CD16;

a first targeting agent which is an antibody, or fragment thereof, directed to HER2 and a second targeting agent which is an antibody, or fragment thereof, directed to CD3;

a first targeting agent which is an antibody, or fragment thereof, directed to CD20 and a second targeting agent which is an antibody, or fragment thereof, directed to CD3;

a first targeting agent which is an antibody, or fragment thereof, directed to EpCAM and a second targeting agent which is an antibody, or fragment thereof, directed to CD3;

a first targeting agent which is an antibody, or fragment thereof, directed to NG2 and a second targeting agent which is an antibody, or fragment thereof, directed to CD28;

a first targeting agent which is an antibody, or fragment thereof, directed to CD19 and a second targeting agent which is an antibody, or fragment thereof, directed to CD3;

a first targeting agent which is an antibody, or fragment thereof, directed to CD19 and a second targeting agent which is an antibody, or fragment thereof, directed to CD16;

a first targeting agent which is an antibody, or fragment thereof, directed to CEA and a second targeting agent which is an antibody, or fragment thereof, directed to HSG;

a first targeting agent which is an antibody, or fragment thereof, directed to MUC-1 and a second targeting agent which is an antibody, or fragment thereof, directed to HSG;

a first targeting agent which is an antibody, or fragment thereof, directed to CA19-9 and a second targeting agent which is an antibody, or fragment thereof, directed to CD3;

a first targeting agent which is an antibody, or fragment thereof, directed to CEA and a second targeting agent which is an antibody, or fragment thereof, directed to CD3;

a first targeting agent which is an antibody, or fragment thereof, directed to OCAA and a second targeting agent which is an antibody, or fragment thereof, directed to CD3;

a first targeting agent which is an antibody, or fragment thereof, directed to MAPG and a second targeting agent which is an antibody, or fragment thereof, directed to CD28;

a first targeting agent which is an antibody, or fragment thereof, directed to HER2 and a second targeting agent which is an antibody, or fragment thereof, directed to CD16;

a first targeting agent which is an antibody, or fragment thereof, directed to glioma and a second targeting agent which is an antibody, or fragment thereof, directed to CD3;

a first targeting agent which is folic acid or folic acid receptor and a second targeting agent which is an antibody, or fragment thereof, directed to CD3 or CD16; and a first targeting agent which is an antibody, or fragment thereof, directed to PD-1 and a second targeting agent which is an antibody, or fragment thereof, directed to PDL-1 or PDL-2.

Embodiment 49. The nucleic acid carrier of embodiment 31, wherein the label is a chemiluminescent agent, a fluorescent agent, an infrared dye, a radiolabel agent, a metal, a chelating agent, a hapten, or a gene or mRNA encoding a detectable protein.

Embodiment 50. The nucleic acid carrier of embodiment 31, wherein the adjuvant is one or more of a CpG containing oligonucleotide, a ssRNA, a dsRNA, a monophosphate lipid, aluminum, squalene, 3-deacyl-monophosphoryl lipid A, vitamin E, surfactant polysorbate 80, mannide-monooleate, SLAG-3, or a galactosylceramide.

Embodiment 51. The nucleic acid carrier of embodiment 50, wherein the CpG containing oligonucleotide is ODN 1585, ODN 1668, ODN 1826, ODN 2006, ODN 2007, ODN 2216, ODN 2336, ODN 2395, ODN M362, AT-ODN-1, AT-ODN-2, ODNBW006, ODN 2088, ODN 4084, ODN INH-1, ODN INH-47, ODN TTAGGG, or G-ODN.

Embodiment 52. The nucleic acid carrier of embodiment 31, wherein the RNA molecule is siRNA, miRNA, mRNA, snRNA, dsRNA, ncRNA, snoRNA, or an aptamer.

Embodiment 53. The nucleic acid carrier of any one of embodiments 1 to 30, wherein the targeting agent is an antigen, an antibody, or a fragment of an antibody, and the oligonucleotide linker conjugating the targeting moiety to the at least one single-stranded arm is a CpG containing oligonucleotide.

Embodiment 54. The nucleic acid carrier of any one of embodiments 1 to 30, wherein the nucleic acid carrier comprises at least one antigen, at least one antibody or fragment thereof directed to an immune cell, and at least one adjuvant.

Embodiment 55. A double monomer nucleic acid carrier comprising a first nucleic acid carrier of any one of embodiments 1 to 30 and a second nucleic acid carrier of any one of embodiments 1 to 30, wherein one single-stranded arm of the first nucleic acid carrier is conjugated to one single-stranded arm of the second nucleic acid carrier, forming a double monomer nucleic acid carrier comprising six peripheral single-stranded arms.

Embodiment 56. The double monomer nucleic acid carrier of embodiment 55, wherein the nucleic acid is deoxyribonucleic acid (DNA), ribonucleic acid (RNA), modified DNA or RNA, or a combination thereof.

Embodiment 57. The double monomer nucleic acid carrier of embodiment 55 or embodiment 56, wherein the double-stranded region is 4 to 2000 bases in length.

Embodiment 58. The double monomer nucleic acid carrier of embodiment 57, wherein the double-stranded region is 5 to 200 bases in length.

Embodiment 59. The double monomer nucleic acid carrier of embodiment 57, wherein the double-stranded region is 25 to 50 bases in length.

Embodiment 60. The double monomer nucleic acid carrier of any one of embodiments 55 to 59, wherein each single-stranded arm is 4 to 200 bases in length.

Embodiment 61. The double monomer nucleic acid carrier of embodiment 60, wherein each single-stranded arm is 5 to 50 bases in length.

Embodiment 62. The double monomer nucleic acid carrier of embodiment 61, wherein each single-stranded arm is 25 to 50 bases in length.

Embodiment 63. The double monomer nucleic acid carrier of embodiment 62, wherein each single-stranded arm is 16 to 50 bases in length.

Embodiment 64. The double monomer nucleic acid carrier of any one of embodiments 55 to 63, wherein the nucleotide sequence of each of the six peripheral single-stranded arms is identical.

Embodiment 65. The double monomer nucleic acid carrier of any one of embodiments 55 to 63, wherein the nucleotide sequence of at least one, at least two, at least three, at least four, or at least five of the peripheral single-stranded arms are different than the nucleotide sequence of the other peripheral single-stranded arms.

Embodiment 66. The double monomer nucleic acid carrier of any one of embodiments 55 to 65, wherein the at least one targeting agent is conjugated to the at least one peripheral single-stranded arm by an oligonucleotide linker.

Embodiment 67. The double monomer nucleic acid carrier of embodiment 66, wherein at least one targeting agent, at least two targeting agents, at least three targeting agents, at least four targeting agents, at least five targeting agents, or six targeting agents are conjugated to the peripheral single-stranded arms.

Embodiment 68. The double monomer nucleic acid carrier of embodiment 67, wherein all targeting agents are identical, or at least one targeting agent, at least two targeting agents, at least three targeting agents, at least four targeting agents, or at least five targeting agents, are different from one another.

Embodiment 69. The double monomer nucleic acid carrier of any one of embodiments 55 to 68, wherein one or more peripheral single-stranded arms not conjugated to a targeting agent is complementary base paired to an oligonucleotide linker.

Embodiment 70. The double monomer nucleic acid carrier of any one of embodiments 55 to 69, wherein the at least one targeting agent is an antigen, a peptide, an antibody or fragment thereof, an antibody-drug conjugate, a non-antibody scaffold, a label, an adjuvant, an RNA molecule, a DNA molecule, a vitamin, a protein, a fusion protein, a fusion peptide, a carbohydrate, a lipid, a polysaccharide, a lipopolysaccharide, a polymer, a virus particle, or a virus-like particle, or any combination thereof.

Embodiment 71. The double monomer nucleic acid carrier of embodiment 70, wherein the polymer is hyaluronic acid, polyargenine, polylysine, polyethylenimine (PEI), polyethyleglycol (PEG), polyglycolic acid (PGA), polylactic acid (PLA), or poly(lactic-co-glycolic acid) (PLGA).

Embodiment 72. The double monomer nucleic acid carrier of embodiment 70, wherein the non-antibody scaffold is an affibody, an affilin, an anticalin, an atrimer, an avimer, a bicyclic peptide, a cys-knot, a DARPin, an FN3, a fynomer, a kunitz domain, or an O-body.

Embodiment 73. The double monomer nucleic acid carrier of embodiment 70, wherein the antigen is a bacterial antigen, a viral antigen, a fungal antigen, a yeast antigen, a protozoan antigen, or prion.

Embodiment 74. The double monomer nucleic acid carrier of embodiment 73, wherein the antigen is from *Acetobacter aurantius, Acinetobacter baumannii, Acinetobacter calcoaceticus, Acinetobacter haemolyticus, Acinetobacter junii, Acinetobacter lwoffii, Actinomyces israelii, Actinomyces viscosus, Aggregatibacter actinomycetemcomitans, Agrobacterium radiobacter, Agrobacterium tumefaciens, Azorhizobium caulinodans, Azotobacter vinelandii, Anaplasma phagocytophilum, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides gingivalis, Bacteroides fragilis, Bacteroides melaninogenicus (Prevotella melaninogenica), Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae (Chlamydia pneumoniae), Chlamydophila psittaci (Chlamydia psittaci), Citrobacter freundii, Citrobacter diverus, Citrobacter koseri, Clostridium botulinum, Clostridium difficile, Clostridium perfringens (Clostridium welchii), Clostridium tetani, Corynebacterium diphtheria, Corynebacterium fusiforme, Coxiella burnetii, Ehrlichia chaffeensis, Enterobacter aerogenes, Enterobacter cloacae, Enterobacter faecalis, Enterococcus avium, Enterococcus durans, Enterococcus faecalis, Enterococcus faecium, Enterococcus galllinarum, Enterococcus maloratus, Eschericia coli, Francisella tularensis, Fusobacterium nucleatum, Gardnerella vaginalis, Haemophilus ducreyi, Haemophilus parainfluenzae, Haemophilus pertussis, Haemophilus vaginalis, Haemophilus influenza, Haemophilus aegyptius, Helicobacter pylori, Klebsiella pneumonia, Klebsiella oxytoca, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella lacunata, Moraxella catarrhalis, Morganella morganii, Mycobacterium avium, Mycobacterium africanum, Mycobacterium bovis, Mycobacterium canetti, Mycobacterium diphtheria, Mycobacterium intracellulare, Mycobacterium leprae, Mycobacterium lepraemurium, Mycobacterium microti, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumonia, Neisseria gonorrhoeae, Neisseria meningitides, Pasteurella multocida, Pasteurella tularensis, Porphyromonas gingivalis, Prevotella melaninogenica (Bacteroides melaninogenicus), Propionibacterium acnes, Proteus mirabillis, Proteus vulgaris, Providencia stuartii, Pseudomonas aeruginosa, Pseudomonas otitidis, Rhizobium radiobacter, Rickettsia prowazekii, Rickettsia psittaci, Rickettsia quintana, Rickettsia rickettsia, Rickettsia trachomae, Rochalimaea henselae, Rochalimaea Quintana, Rothia dentocariosa, Salmonella enteritidis, Salmonella typhi, Salmonella typhimurium, Serratia marcescens, Shigella dysenteriae, Staphylococcus aureus,* methicillin-resistant *Staphylococcus aureus, Staphylococcus pneumoniae, Staphylococcus epidermidis, Staphylococcus saprophyticus, Staphylococcus colmii, Staphylococcus sciuri, Staphylococcus warneri, Stenotrophomonas maltophilia, Streptococcus agalactiae, Streptococcus anginosus, Streptococcus avium, Streptococcus bovis, Streptococcus cricetus, Streptococcus faceium, Streptococcus faecalis, Streptococcus ferus, Streptococcus gallinarum, Streptococcus lactis. Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococ-* cus sanguis, Streptococcus sobrinus, Streptococcus viridans, Treponema pallidum, Treponema denticola, Vibrio cholera, Vibrio comma, Vibrio parahaemolyticus, Vibrio vulnificus, Wolbachia, Yersinia enterocolitica, Yersinia pestis, Yersinia pseudotuberculosis, Aspergillus fumigatus, Aspergillus flavus, Aspergillus clavatus, Aspergillus niger, Aspergillus terreus, Candida albicans, Candida glabrata, Candida tropicalis, Candida krusei, Candida dubliniensis, Candida parapsilosis, Fusarium solani, Fusarium moniliforme, Fusarium proliferartum, Malessezia pachydermatis, Chrysosporium parvum, Metarhizium anisopliae, Phaeoisaria clematidis, or Sarcopodium oculorum.

Embodiment 75. The double monomer nucleic acid carrier of embodiment 73, wherein the antigen is from Mycobacterium tuberculosis, Varicella zoster virus, Corynebacterium diphtheria, Hepatitis A virus, Hepatitis B virus, Hepatitis C virus, Haemophilis influenza, Human Papillomavirus, Influenza virus, Japanese Encephalitis virus, Measles virus, Neisseria meningitidis, Mumps virus, Bordetella pertussis, Streptococcus pneumonia, Poliovirus, Rabies virus, Rotavirus, Rubella virus, Herpes Zoster virus, Clostridium tetani, Salmonella typhi, Yellow Fever virus, Ebola virus, avian flu virus, Bacillus anthracis, Smallpox virus, and Zika virus.

Embodiment 76. The double monomer nucleic acid carrier of embodiment 70, wherein the antibody fragment is Fab, F(ab')$_2$, scFv, tandem scFv, a BiTE, single domain (sdAb) antibody, diabody, single chain diabody, minibody, fusion protein, or scFv-Fc.

Embodiment 77. The double monomer nucleic acid carrier of embodiment 70, wherein the antibody, or fragment thereof, is directed to a disease-associated antigen.

Embodiment 78. The double monomer nucleic acid carrier of embodiment 77, wherein the disease-associated antigen is a tumor-associated antigen.

Embodiment 79. The double monomer nucleic acid carrier of embodiment 78, wherein the tumor-associated antigen is 4-1BB, 5AC, 5T4, A2aR, activin receptor-like kinase 1, AGS-22M6, AKAP4, alpha-fetoprotein, angiopoietin 2, B7-H3, BAFF, BAGE, BCR-ABL, BORIS, CA-125, CA19-9, C242 antigen, carbonic anhydrase 9 (CA-IX), CCR4, CD19, CD20, CD22, CD23 (IgE receptor), CD24, CD28, CD30 (TNFRSF8), CD33, CD37, CD38 (cyclic ADP ribose hydrolase), CD40, CD44 v6, CD51, CD56, CD70, CD71, CD73, CD74, CD79B, CD80, CD137, CD140a, CD152, CD200, CD221, CD274, CEA, ch4D5, CLDN18.2, CS1, CSFIR, CTLA-4, C-X-C chemokine receptor type 4, DLL4, DR5, EBAG9, EGF, EGFR, EGFL7, EpCAM, ERBB2, ERBB3, FAP, fibronectin extra domain-B, folate receptor 1, folate receptor alpha, folate hydrolase, Frizzled receptor, GAGE, GD2 ganglioside, GD3 ganglioside, glioma, glypican 3, GPNMB, gp100, GUCY2C, HER1, HER2/neu, HER3, HGF, HHGFR, histone complex, HLA-DR, human scatter factor receptor kinase, HPV-16, HSP105, IDH1, IDO1, IGF-I, IGF-1 receptor, ILGF2, IL-6, IL-13, integrin αvβ3, integrin α5β1, KIR, LAG-3, Lewis-Y antigen, LY6K, MAGE-1, MAGE-A3, MAGE-C2, MAGE-D4, MAPG, MART-1, Melan-A, MET, MCP-1, mesothelin, MIF, MSLN, MS4A1, mucin CanAg, MUC1, MUC4, MUC16, NG2, N-glycolylneuraminic acid, Notch receptor PD-1, NY-ESO-1, OCAA, PAP, PDGF-R α, PDCD1, PD1, PD-L1, phosphate-sodium co-transporter, phosphatidylserine, PRAME, PSA, RANKL, RON, ROR1, SDC1, Sialyl-Tn, SLAMF7, SPAG-9, SSX1, STEAP1, survivin, TAG-72, telomerase, TEM1, tenascin C, TGF-β, TIM-3, TLR, TAM, TIM-3, TRAIL-R2, TRAIL-R1, TWEAK receptor, tumor specific glycosylation of MUC1, tumor-associated calcium signal transducer 2, tumor antigen CTAA16.88, TYRP1 (glycoprotein 75), VEGF-A, VEGFR2, VEGFR-1, vimentin, VISTA, WT1, or XAGE-1b.

Embodiment 80. The double monomer nucleic acid carrier of embodiment 78, wherein the tumor-associated antigen is chosen from HER-2, EGFR, CD30, CD20, EpCAM, NG2, CD19, CEA, MUC-1, CA19-9, OCAA, MAPG, TAM, TLR, CD71, ERBB2, VEGF, and glioma.

Embodiment 81. The double monomer nucleic acid carrier of embodiment 77, wherein the disease-associated antigen is 1-40-β-amyloid, AOC3 (VAP-1), ACVR2B, angiopoietin 3, beta-amyloid, C5, CCL11 (eotaxin-1), CCR5, CD2, CD3, CD4, CD5, CD11, CD18, CD20, CD23 (IgE receptor), CD25 (a chain of IL-2 receptor), CD28, CD41 (integrin alpha-IIb), CD52, CD125, CD147 (basigin), CD154 (CD40L), CEA-related antigen, clumping factor A, endotoxin, GMCSF receptor α-chain, growth differentiation factor 8, hemagglutinin, HNGF, Hsp90, IGHE, IgE Fc region, IL-1β, IL-4, IL-5, IL-6, IL-9, IL-12, IL-13, IL-17, IL-17A, IL-20, IL-22, IL-23, IL-6 receptor, integrin α4β7, integrin α7β7, integrin α4, integrin αIIbβ3, interferon α/β receptor, interferon gamma-induced protein, IFN-γ, IFN-α, ITGB2 (CD18), LFA-1 (CD11a), LINGO-1, lipoteichoic acid, LOXL2, myelin-associated glycoprotein, myostatin, neural apoptosis-regulated proteinase 1, NGF, NOGO-A, Oryctolagus cuniculus, OX-40, PCSK9, phosphatidylserine, platelet-derived growth factor receptor beta, RANKL, Rhesus factor, sclerostin, SOST, sphingosine-1-phosphate, TFPI, TGF-β, TGF beta 2, TGF beta 1, TNF-α, VEGF-A, or VWF.

Embodiment 82. The double monomer nucleic acid carrier of embodiment 70, wherein the antibody, or fragment thereof, is directed to a cell surface marker.

Embodiment 83. The double monomer nucleic acid carrier of embodiment 82, wherein the cell surface marker is on an immune cell.

Embodiment 84. The double monomer nucleic acid carrier of embodiment 83, wherein the immune cell is a T cell, B cell, NK cell, macrophage, TIL, dendritic cell, neutrophil, eosinophil, basophil, or mast cell.

Embodiment 85. The double monomer nucleic acid carrier of embodiment 84, wherein the T cell is a CD4$^+$ T cell, CD8$^+$ T cell, helper T cell, cytotoxic T cell, or natural killer T cell; and wherein the B cell is a memory B cell or a plasma cell.

Embodiment 86. The double monomer nucleic acid carrier of embodiment 82, wherein the cell surface marker is CD36, CD68, CD83, CD180, CD206 (MRC1-mannose receptor), F4/80 (EGF-TM7 family), CD205, CD56, CD161, CD94:NKG2 heterodimer, KIR/CD158 family, CD335, CD64, CD16, CD3, CD28, CD4, CD25, CD39, Toll-like receptors (TLRs), CD281, CD283, CD284, CD286, CD289, CD282, C-type lectin receptors (CLRs), Fc Receptor, or HSG.

Embodiment 87. The double monomer nucleic acid carrier of embodiment 70, comprising one or two of the following:
  a first targeting agent which is an antibody, or fragment thereof, directed to HER2 and a second targeting agent which is an antibody, or fragment thereof, directed to CD64;
  a first targeting agent which is an antibody, or fragment thereof, directed to EGFR and a second targeting agent which is an antibody, or fragment thereof, directed to CD64;

a first targeting agent which is an antibody, or fragment thereof, directed to EGFR and a second targeting agent which is an antibody, or fragment thereof, directed to PD-1;

a first targeting agent which is an antibody, or fragment thereof, directed to PD-L1 and a second targeting agent which is an antibody, or fragment thereof, directed to OX40;

a first targeting agent which is an antibody, or fragment thereof, directed to CD30 and a second targeting agent which is an antibody, or fragment thereof, directed to CD16;

a first targeting agent which is an antibody, or fragment thereof, directed to HER2 and a second targeting agent which is an antibody, or fragment thereof, directed to CD3;

a first targeting agent which is an antibody, or fragment thereof, directed to CD20 and a second targeting agent which is an antibody, or fragment thereof, directed to CD3;

a first targeting agent which is an antibody, or fragment thereof, directed to EpCAM and a second targeting agent which is an antibody, or fragment thereof, directed to CD3;

a first targeting agent which is an antibody, or fragment thereof, directed to NG2 and a second targeting agent which is an antibody, or fragment thereof, directed to CD28;

a first targeting agent which is an antibody, or fragment thereof, directed to CD19 and a second targeting agent which is an antibody, or fragment thereof, directed to CD3;

a first targeting agent which is an antibody, or fragment thereof, directed to CD19 and a second targeting agent which is an antibody, or fragment thereof, directed to CD16;

a first targeting agent which is an antibody, or fragment thereof, directed to CEA and a second targeting agent which is an antibody, or fragment thereof, directed to HSG;

a first targeting agent which is an antibody, or fragment thereof, directed to MUC-1 and a second targeting agent which is an antibody, or fragment thereof, directed to HSG;

a first targeting agent which is an antibody, or fragment thereof, directed to CA19-9 and a second targeting agent which is an antibody, or fragment thereof, directed to CD3;

a first targeting agent which is an antibody, or fragment thereof, directed to CEA and a second targeting agent which is an antibody, or fragment thereof, directed to CD3;

a first targeting agent which is an antibody, or fragment thereof, directed to OCAA and a second targeting agent which is an antibody, or fragment thereof, directed to CD3;

a first targeting agent which is an antibody, or fragment thereof, directed to MAPG and a second targeting agent which is an antibody, or fragment thereof, directed to CD28;

a first targeting agent which is an antibody, or fragment thereof, directed to HER2 and a second targeting agent which is an antibody, or fragment thereof, directed to CD16;

a first targeting agent which is an antibody, or fragment thereof, directed to glioma and a second targeting agent which is an antibody, or fragment thereof, directed to CD3;

a first targeting agent which is folic acid or folic acid receptor and a second targeting agent which is an antibody, or fragment thereof, directed to CD3 or CD16; and a first targeting agent which is an antibody, or fragment thereof, directed to PD-1 and a second targeting agent which is an antibody, or fragment thereof, directed to PDL-1 or PDL-2.

Embodiment 88. The double monomer nucleic acid carrier of embodiment 70, wherein the label is a chemiluminescent agent, a fluorescent agent, an infrared dye, a radiolabel agent, a metal, a chelating agent, a hapten, or a gene or mRNA encoding a detectable protein.

Embodiment 89. The double monomer nucleic acid carrier of embodiment 70, wherein the adjuvant is one or more of a CpG containing oligonucleotide, a ssRNA, a dsRNA, a monophosphate lipid, aluminum, squalene, 3-deacyl-monophosphoryl lipid A, vitamin E, surfactant polysorbate 80, mannide-mono-oleate, SLAG-3, or a galactosylceramide.

Embodiment 90. The double monomer nucleic acid carrier of embodiment 89, wherein the CpG containing oligonucleotide is ODN 1585, ODN 1668, ODN 1826, ODN 2006, ODN 2007, ODN 2216, ODN 2336, ODN 2395, ODN M362, AT-ODN-1, AT-ODN-2, ODNBW006, ODN 2088, ODN 4084, ODN INH-1, ODN INH-47, ODN TTAGGG, or G-ODN.

Embodiment 91. The double monomer nucleic acid carrier of embodiment 70, wherein the RNA molecule is siRNA, miRNA, mRNA, snRNA, dsRNA, ncRNA, snoRNA, or an aptamer.

Embodiment 92. The double monomer nucleic acid carrier of any one of embodiments 55 to 69, wherein the targeting agent is an antigen, an antibody, or a fragment of an antibody, and the oligonucleotide linker conjugating the targeting moiety to the at least one single-stranded arm is a CpG containing oligonucleotide.

Embodiment 93. The double monomer nucleic acid carrier of any one of embodiments 55 to 69, wherein the nucleic acid carrier comprises at least one antigen, at least one antibody or fragment thereof directed to an immune cell, and at least one adjuvant.

Embodiment 94. A trimer nucleic acid carrier comprising:
a first oligonucleotide having a central portion, a first terminal arm, and a second terminal arm;
a second oligonucleotide having a central portion, a first terminal arm, and a second terminal arm, wherein the first terminal arm of the second oligonucleotide is complementary to the first terminal arm of the first oligonucleotide and hybridized thereto; and
a third oligonucleotide having a central portion, a first terminal arm, and a second terminal arm, wherein the first terminal arm of the third oligonucleotide is complementary to the second terminal arm of the first oligonucleotide and hybridized thereto;
wherein the second terminal arm of the second oligonucleotide is conjugated to a first targeting agent, and the second terminal arm of the third oligonucleotide is conjugated to a second targeting agent.

Embodiment 95. The trimer nucleic acid carrier of embodiment 94, wherein the nucleic acid is deoxyribonucleic acid (DNA), ribonucleic acid (RNA), modified DNA or RNA, or a combination thereof.

Embodiment 96. The trimer nucleic acid carrier of embodiment 94 or embodiment 95, wherein the central portion of each of the first and second oligonucleotides is 4 to 2000 bases in length.

Embodiment 97. The trimer nucleic acid carrier of embodiment 96, wherein the central portion of each of the first and second oligonucleotides is 5 to 200 bases in length.

Embodiment 98. The trimer nucleic acid carrier of embodiment 96, wherein the central portion of each of the first and second oligonucleotides is 25 to 50 bases in length.

Embodiment 99. The trimer nucleic acid carrier of any one of embodiments 94 to 98, wherein each of the first and second terminal arms of each of the first and second oligonucleotides is 4 to 200 bases in length.

Embodiment 100. The trimer nucleic acid carrier of embodiment 99, wherein each of the first and second terminal arms of each of the first and second oligonucleotides is 5 to 50 bases in length.

Embodiment 101. The trimer nucleic acid carrier of embodiment 99, wherein each of the first and second terminal arms of each of the first and second oligonucleotides is 25 to 50 bases in length.

Embodiment 102. The trimer nucleic acid carrier of embodiment 99, wherein each of the first and second terminal arms of each of the first and second oligonucleotides is 16 to 50 bases in length.

Embodiment 103. The trimer nucleic acid carrier of any one of embodiments 94 to 102, wherein the nucleotide sequences of the four terminal arms are identical.

Embodiment 104. The trimer nucleic acid carrier of any one of embodiments 94 to 102, wherein the nucleotide sequences of three of the terminal arms are identical and different than the nucleotide sequence of the fourth terminal arm.

Embodiment 105. The trimer nucleic acid carrier of any one of embodiments 94 to 102, wherein the nucleotide sequences of two of the terminal arms are identical to each other and different than the nucleotide sequences of the other two terminal arms.

Embodiment 106. The trimer nucleic acid carrier of any one of embodiments 94 to 102, wherein the nucleotide sequences of two of the terminal arms are identical to each other and the nucleotide sequences of the other two terminal arms are identical to each other, wherein the nucleotide sequence of the first two terminal arms is different than the nucleotide sequences of the second two terminal arms.

Embodiment 107. The trimer nucleic acid carrier of any one of embodiments 94 to 102, wherein the nucleotide sequence of each of the four terminal arms is different.

Embodiment 108. The trimer nucleic acid carrier of any one of embodiments 94 to 107, wherein the first and second targeting agents are conjugated to the terminal arms by an oligonucleotide linker.

Embodiment 109. The trimer nucleic acid carrier of any one of embodiments 94 to 108, wherein the first targeting agent is identical to the second targeting agent.

Embodiment 110. The trimer nucleic acid carrier of any one of embodiments 94 to 108, wherein the first targeting agent is different than the second targeting agent.

Embodiment 111. The trimer nucleic acid carrier of any one of embodiments 94 to 110, wherein the targeting agent is an antigen, a peptide, an antibody or fragment thereof, an antibody-drug conjugate, a non-antibody scaffold, a label, an adjuvant, an RNA molecule, a DNA molecule, a vitamin, a protein, a fusion protein, a fusion peptide, a carbohydrate, a lipid, a polysaccharide, a lipopolysaccharide, a polymer, a virus particle, a virus-like particle, or any combination thereof.

Embodiment 112. The trimer nucleic acid carrier of embodiment 111, wherein the polymer is hyaluronic acid, polyargenine, polylysine, polyethylenimine (PEI), polyethyleglycol (PEG), polyglycolic acid (PGA), polylactic acid (PLA), or poly(lactic-co-glycolic acid) (PLGA).

Embodiment 113. The trimer nucleic acid carrier of embodiment 111, wherein the non-antibody scaffold is an affibody, an affilin, an anticalin, an atrimer, an avimer, a bicyclic peptide, a cys-knot, a DARPin, an FN3, a fynomer, a kunitz domain, or an O-body.

Embodiment 114. The trimer nucleic acid carrier of embodiment 111, wherein the antigen is a bacterial antigen, a viral antigen, a fungal antigen, a yeast antigen, a protozoan antigen, or prion.

Embodiment 115. The trimer nucleic acid carrier of embodiment 114, wherein the antigen is from *Acetobacter aurantius, Acinetobacter baumannii, Acinetobacter calcoaceticus, Acinetobacter haemolyticus, Acinetobacter junii, Acinetobacter lwoffii, Actinomyces israelii, Actinomyces viscosus, Aggregatibacter actinomycetemcomitans, Agrobacterium radiobacter, Agrobacterium tumefaciens, Azorhizobium caulinodans, Azotobacter vinelandii, Anaplasma phagocytophilum, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides gingivalis, Bacteroides fragilis, Bacteroides melaninogenicus (Prevotella melaninogenica), Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae (Chlamydia pneumoniae), Chlamydophila psittaci (Chlamydia psittaci), Citrobacter freundii, Citrobacter diverus, Citrobacter koseri, Clostridium botulinum, Clostridium difficile, Clostridium perfringens (Clostridium welchii), Clostridium tetani, Corynebacterium diphtheria, Corynebacterium fusiforme, Coxiella burnetii, Ehrlichia chaffeensis, Enterobacter aerogenes, Enterobacter cloacae, Enterobacter faecalis, Enterococcus avium, Enterococcus durans, Enterococcus faecalis, Enterococcus faecium, Enterococcus galllinarum, Enterococcus maloratus, Eschericia coli, Francisella tularensis, Fusobacterium nucleatum, Gardnerella vaginalis, Haemophilus ducreyi, Haemophilus parainfluenzae, Haemophilus pertussis, Haemophilus vaginalis, Haemophilus influenza, Haemophilus aegyptius, Helicobacter pylori, Klebsiella pneumonia, Klebsiella oxytoca, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella lacunata, Moraxella catarrhalis, Morganella morganii, Mycobacterium avium, Mycobacterium africanum, Mycobacterium bovis, Mycobacterium canetti, Mycobacterium diphtheria, Mycobacterium intracellulare, Mycobacterium leprae, Mycobacterium lepraemurium, Mycobacterium microti, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumonia, Neisseria gonorrhoeae, Neisseria meningitides, Pasteurella multocida, Pasteurella tularensis, Porphyromo-* nas gingivalis, Prevotella melaninogenica (Bacteroides melaninogenicus), Propionibacterium acnes, Proteus mirabillis, Proteus vulgaris, Providencia stuartii, Pseudomonas aeruginosa, Pseudomonas otitidis, Rhizobium radiobacter, Rickettsia prowazekii, Rickettsia psittaci, Rickettsia quintana, Rickettsia rickettsia, Rickettsia trachomae, Rochalimaea henselae, Rochalimaea Quintana, Rothia dentocariosa, Salmonella enteritidis, Salmonella typhi, Salmonella typhimurium, Serratia marcescens, Shigella dysenteriae, Staphylococcus aureus, methicillin-resistant Staphylococcus aureus, Staphylococcus pneumoniae, Staphylococcus epidermidis, Staphylococcus saprophyticus, Staphylococcus colmii, Staphylococcus sciuri, Staphylococcus warneri, Stenotrophomonas maltophilia, Streptococcus agalactiae, Streptococcus anginosus, Streptococcus avium, Streptococcus bovis, Streptococcus cricetus, Streptococcus faceium, Streptococcus faecalis, Streptococcus ferus, Streptococcus gallinarum, Streptococcus lactis. Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Streptococcus viridans, Treponema pallidum, Treponema denticola, Vibrio cholera, Vibrio comma, Vibrio parahaemolyticus, Vibrio vulnificus, Wolbachia, Yersinia enterocolitica, Yersinia pestis, Yersinia pseudotuberculosis, Aspergillus fumigatus, Aspergillus flavus, Aspergillus clavatus, Aspergillus niger, Aspergillus terreus, Candida albicans, Candida glabrata, Candida tropicalis, Candida krusei, Candida dubliniensis, Candida parapsilosis, Fusarium solani, Fusarium moniliforme, Fusarium proliferartum, Malessezia pachydermatis, Chrysosporium parvum, Metarhizium anisopliae, Phaeoisaria clematidis, or Sarcopodium oculorum.

Embodiment 116. The trimer nucleic acid carrier of embodiment 114, wherein the antigen is from Mycobacterium tuberculosis, Varicella zoster virus, Corynebacterium diphtheria, Hepatitis A virus, Hepatitis B virus, Hepatitis C virus, Haemophilus influenza, Human Papillomavirus, Influenza virus, Japanese Encephalitis virus, Measles virus, Neisseria meningitidis, Mumps virus, Bordetella pertussis, Streptococcus pneumonia, Poliovirus, Rabies virus, Rotavirus, Rubella virus, Herpes Zoster virus, Clostridium tetani, Salmonella typhi, Yellow Fever virus, Ebola virus, avian flu virus, Bacillus anthracis, Smallpox virus, or Zika virus.

Embodiment 117. The trimer nucleic acid carrier of embodiment 111, wherein the antibody fragment is Fab, F(ab')$_2$, scFv, tandem scFv, a BiTE, single domain (sdAb) antibody, diabody, single chain diabody, minibody, fusion protein, or scFv-Fc.

Embodiment 118. The trimer nucleic acid carrier of embodiment 111, wherein the antibody, or fragment thereof, is directed to a disease-associated antigen.

Embodiment 119. The trimer nucleic acid carrier of embodiment 118, wherein the disease-associated antigen is a tumor-associated antigen.

Embodiment 120. The trimer nucleic acid carrier of embodiment 119, wherein the tumor-associated antigen is 4-1BB, 5AC, 5T4, A2aR, activin receptor-like kinase 1, AGS-22M6, AKAP4, alpha-fetoprotein, angiopoietin 2, B7-H3, BAFF, BAGE, BCR-ABL, BORIS, CA-125, CA19-9, C242 antigen, carbonic anhydrase 9 (CA-IX), CCR4, CD19, CD20, CD22, CD23 (IgE receptor), CD24, CD28, CD30 (TNFRSF8), CD33, CD37, CD38 (cyclic ADP ribose hydrolase), CD40, CD44 v6, CD51, CD56, CD70, CD71, CD73, CD74, CD79B, CD80, CD137, CD140a, CD152, CD200, CD221, CD274, CEA, ch4D5, CLDN18.2, CS1, CSFIR, CTLA-4, C-X-C chemokine receptor type 4, DLL4, DR5, EBAG9, EGF, EGFR, EGFL7, EpCAM, ERBB2, ERBB3, FAP, fibronectin extra domain-B, folate receptor 1, folate receptor alpha, folate hydrolase, Frizzled receptor, GAGE, GD2 ganglioside, GD3 ganglioside, glioma, glypican 3, GPNMB, gp100, GUCY2C, HER1, HER2/neu, HER3, HGF, HHGFR, histone complex, HLA-DR, human scatter factor receptor kinase, HPV-16, HSP105, IDH1, IDO1, IGF-I, IGF-1 receptor, ILGF2, IL-6, IL-13, integrin $\alpha v\beta 3$, integrin $\alpha 5\beta 1$, KIR, LAG-3, Lewis-Y antigen, LY6K, MAGE-1, MAGE-A3, MAGE-C2, MAGE-D4, MAPG, MART-1, Melan-A, MET, MCP-1, mesothelin, MIF, MSLN, MS4A1, mucin CanAg, MUC1, MUC4, MUC16, NG2, N-glycolylneuraminic acid, Notch receptor PD-1, NY-ESO-1, OCAA, PAP, PDGF-R $\alpha$, PDCD1, PD1, PD-L1, phosphate-sodium co-transporter, phosphatidylserine, PRAME, PSA, RANKL, RON, ROR1, SDC1, Sialyl-Tn, SLAMF7, SPAG-9, SSX1, STEAP1, survivin, TAG-72, telomerase, TEM1, tenascin C, TGF-$\beta$, TIM-3, TLR, TAM, TIM-3, TRAIL-R2, TRAIL-R1, TWEAK receptor, tumor specific glycosylation of MUC1, tumor-associated calcium signal transducer 2, tumor antigen CTAA16.88, TYRP1 (glycoprotein 75), VEGF-A, VEGFR2, VEGFR-1, vimentin, VISTA, WT1, and XAGE-1b.

Embodiment 121. The trimer nucleic acid carrier of embodiment 119, wherein the tumor-associated antigen is HER-2, EGFR, CD30, CD20, EpCAM, NG2, CD19, CEA, MUC-1, CA19-9, OCAA, MAPG, TAM, TLR, CD71, ERBB2, VEGF, or glioma.

Embodiment 122. The trimer nucleic acid carrier of embodiment 118, wherein the disease-associated antigen is 1-40-$\beta$-amyloid, AOC3 (VAP-1), ACVR2B, angiopoietin 3, beta-amyloid, C5, CCL11 (eotaxin-1), CCR5, CD2, CD3, CD4, CD5, CD11, CD18, CD20, CD23 (IgE receptor), CD25 (a chain of IL-2 receptor), CD28, CD41 (integrin alpha-IIb), CD52, CD125, CD147 (basigin), CD154 (CD40L), CEA-related antigen, clumping factor A, endotoxin, GMCSF receptor $\alpha$-chain, growth differentiation factor 8, hemagglutinin, HNGF, Hsp90, IGHE, IgE Fc region, IL-1$\beta$, IL-4, IL-5, IL-6, IL-9, IL-12, IL-13, IL-17, IL-17A, IL-20, IL-22, IL-23, IL-6 receptor, integrin $\alpha 4\beta 7$, integrin $\alpha 7\beta 7$, integrin $\alpha 4$, integrin $\alpha IIb\beta 3$, interferon $\alpha/\beta$ receptor, interferon gamma-induced protein, IFN-$\gamma$, IFN-$\alpha$, ITGB2 (CD18), LFA-1 (CD11a), LINGO-1, lipoteichoic acid, LOXL2, myelin-associated glycoprotein, myostatin, neural apoptosis-regulated proteinase 1, NGF, NOGO-A, Oryctolagus cuniculus, OX-40, PCSK9, phosphatidylserine, platelet-derived growth factor receptor beta, RANKL, Rhesus factor, sclerostin, SOST, sphingosine-1-phosphate, TFPI, TGF-$\beta$, TGF beta 2, TGF beta 1, TNF-$\alpha$, VEGF-A, or VWF.

Embodiment 123. The trimer nucleic acid carrier of embodiment 111, wherein the antibody, or fragment thereof, is directed to a cell surface marker.

Embodiment 124. The trimer nucleic acid carrier of embodiment 123, wherein the cell surface marker is on an immune cell.

Embodiment 125. The trimer nucleic acid carrier of embodiment 124, wherein the immune cell is a T cell, B cell, NK cell, macrophage, TIL, dendritic cell, neutrophil, eosinophil, basophil, or mast cell.

Embodiment 126. The trimer nucleic acid carrier of embodiment 125, wherein the T cell is a CD4$^+$ T cell, CD8$^+$ T cell, helper T cell, cytotoxic T cell, or natural killer T cell; and wherein the B cell is a memory B cell or a plasma cell.

Embodiment 127. The trimer nucleic acid carrier of embodiment 123, wherein the cell surface marker is CD36, CD68, CD83, CD180, CD206 (MRC1-mannose receptor), F4/80 (EGF-TM7 family), CD205, CD56, CD161, CD94:

NKG2 heterodimer, KIR/CD158 family, CD335, CD64, CD16, CD3, CD28, CD4, CD25, CD39, Toll-like receptors (TLRs), CD281, CD283, CD284, CD286, CD289, CD282, C-type lectin receptors (CLRs), Fc Receptor, or HSG.

Embodiment 128. The trimer nucleic acid carrier of embodiment 111, comprising one or two of the following:
- a first targeting agent which is an antibody, or fragment thereof, directed to HER2 and a second targeting agent which is an antibody, or fragment thereof, directed to CD64;
- a first targeting agent which is an antibody, or fragment thereof, directed to EGFR and a second targeting agent which is an antibody, or fragment thereof, directed to CD64;
- a first targeting agent which is an antibody, or fragment thereof, directed to EGFR and a second targeting agent which is an antibody, or fragment thereof, directed to PD-1;
- a first targeting agent which is an antibody, or fragment thereof, directed to PD-L1 and a second targeting agent which is an antibody, or fragment thereof, directed to OX40;
- a first targeting agent which is an antibody, or fragment thereof, directed to CD30 and a second targeting agent which is an antibody, or fragment thereof, directed to CD16;
- a first targeting agent which is an antibody, or fragment thereof, directed to HER2 and a second targeting agent which is an antibody, or fragment thereof, directed to CD3;
- a first targeting agent which is an antibody, or fragment thereof, directed to CD20 and a second targeting agent which is an antibody, or fragment thereof, directed to CD3;
- a first targeting agent which is an antibody, or fragment thereof, directed to EpCAM and a second targeting agent which is an antibody, or fragment thereof, directed to CD3;
- a first targeting agent which is an antibody, or fragment thereof, directed to NG2 and a second targeting agent which is an antibody, or fragment thereof, directed to CD28;
- a first targeting agent which is an antibody, or fragment thereof, directed to CD19 and a second targeting agent which is an antibody, or fragment thereof, directed to CD3;
- a first targeting agent which is an antibody, or fragment thereof, directed to CD19 and a second targeting agent which is an antibody, or fragment thereof, directed to CD16;
- a first targeting agent which is an antibody, or fragment thereof, directed to CEA and a second targeting agent which is an antibody, or fragment thereof, directed to HSG;
- a first targeting agent which is an antibody, or fragment thereof, directed to MUC-1 and a second targeting agent which is an antibody, or fragment thereof, directed to HSG;
- a first targeting agent which is an antibody, or fragment thereof, directed to CA19-9 and a second targeting agent which is an antibody, or fragment thereof, directed to CD3;
- a first targeting agent which is an antibody, or fragment thereof, directed to CEA and a second targeting agent which is an antibody, or fragment thereof, directed to CD3;
- a first targeting agent which is an antibody, or fragment thereof, directed to OCAA and a second targeting agent which is an antibody, or fragment thereof, directed to CD3;
- a first targeting agent which is an antibody, or fragment thereof, directed to MAPG and a second targeting agent which is an antibody, or fragment thereof, directed to CD28;
- a first targeting agent which is an antibody, or fragment thereof, directed to HER2 and a second targeting agent which is an antibody, or fragment thereof, directed to CD16;
- a first targeting agent which is an antibody, or fragment thereof, directed to glioma and a second targeting agent which is an antibody, or fragment thereof, directed to CD3;
- a first targeting agent which is folic acid or folic acid receptor and a second targeting agent which is an antibody, or fragment thereof, directed to CD3 or CD16; and
- a first targeting agent which is an antibody, or fragment thereof, directed to PD-1 and a second targeting agent which is an antibody, or fragment thereof, directed to PDL-1 or PDL-2.

Embodiment 129. The trimer nucleic acid carrier of embodiment 111, wherein the label is a chemiluminescent agent, a fluorescent agent, an infrared dye, a radiolabel agent, a metal, a chelating agent, a hapten, or a gene or mRNA encoding a detectable protein.

Embodiment 130. The trimer nucleic acid carrier of embodiment 111, wherein the adjuvant is one or more of a CpG containing oligonucleotide, a ssRNA, a dsRNA, a monophosphate lipid, aluminum, squalene, 3-deacyl-monophosphoryl lipid A, vitamin E, surfactant polysorbate 80, mannide-mono-oleate, SLAG-3, or a galactosylceramide.

Embodiment 131. The trimer nucleic acid carrier of embodiment 130, wherein the CpG containing oligonucleotide is ODN 1585, ODN 1668, ODN 1826, ODN 2006, ODN 2007, ODN 2216, ODN 2336, ODN 2395, ODN M362, AT-ODN-1, AT-ODN-2, ODNBW006, ODN 2088, ODN 4084, ODN INH-1, ODN INH-47, ODN TTAGGG, or G-ODN.

Embodiment 132. The trimer nucleic acid carrier of embodiment 111, wherein the RNA molecule is siRNA, miRNA, mRNA, snRNA, dsRNA, ncRNA, snoRNA, or an aptamer.

Embodiment 133. The trimer nucleic acid carrier of any one of embodiments 94 to 110, wherein the targeting agent is an antigen, an antibody, or a fragment of an antibody, and the oligonucleotide linker conjugating the targeting moiety to the at least one single-stranded arm is a CpG containing oligonucleotide.

Embodiment 134. A nucleic acid carrier comprising:
- a central portion, a first terminal arm, and a second terminal arm;
- wherein the first terminal arm is conjugated to a first targeting agent, and the second terminal is conjugated to a second targeting agent.

Embodiment 135. The nucleic acid carrier of embodiment 134, wherein the central portion, the first terminal arm, and the second terminal arm are single-stranded DNA.

Embodiment 136. The nucleic acid carrier of embodiment 134, wherein the central portion, the first terminal arm, and the second terminal arm are double-stranded DNA.

Embodiment 137. The nucleic acid carrier of any one of embodiments 134 to 136, wherein the nucleic acid is deoxyribonucleic acid (DNA), ribonucleic acid (RNA), modified DNA or RNA, or a combination thereof.

Embodiment 138. The nucleic acid carrier of any one of embodiments 134 to 137, wherein the central portion is 4 to 2000 bases in length.

Embodiment 139. The nucleic acid carrier of embodiment 138, wherein the central portion is 5 to 200 bases in length.

Embodiment 140. The nucleic acid carrier of embodiment 138, wherein the central portion is 25 to 50 bases in length.

Embodiment 141. The nucleic acid carrier of any one of embodiments 134 to 140, wherein each of the first and second terminal arms is 4 to 200 bases in length.

Embodiment 142. The nucleic acid carrier of embodiment 141, wherein each of the first and second terminal arms is 5 to 50 bases in length.

Embodiment 143. The nucleic acid carrier of embodiment 141, wherein each of the first and second terminal arms is 25 to 50 bases in length.

Embodiment 144. The nucleic acid carrier of embodiment 141, wherein each of the first and second terminal arms is 16 to 50 bases in length.

Embodiment 145. The nucleic acid carrier of any one of embodiments 134 to 144, wherein the nucleotide sequences of the two terminal arms are identical.

Embodiment 146. The nucleic acid carrier of any one of embodiments 134 to 144, wherein the nucleotide sequences of the two terminal arms are different.

Embodiment 147. The nucleic acid carrier of any one of embodiments 134 to 146, wherein the first and second targeting agents are conjugated to the terminal arms by an oligonucleotide linker.

Embodiment 148. The nucleic acid carrier of any one of embodiments 134 to 147, wherein the first targeting agent is identical to the second targeting agent.

Embodiment 149. The nucleic acid carrier of any one of embodiments 134 to 147, wherein the first targeting agent is different than the second targeting agent.

Embodiment 150. The nucleic acid carrier of any one of embodiments 134 to 149, wherein the targeting agent is an antigen, a peptide, an antibody or fragment thereof, an antibody-drug conjugate, a non-antibody scaffold, a label, an adjuvant, an RNA molecule, a DNA molecule, a vitamin, a protein, a fusion protein, a fusion peptide, a carbohydrate, a lipid, a polysaccharide, a lipopolysaccharide, a polymer, a virus particle, of a virus-like particle, or any combination thereof.

Embodiment 151. The nucleic acid carrier of embodiment 150, wherein the polymer is hyaluronic acid, polyargenine, polylysine, polyethylenimine (PEI), polyethyleglycol (PEG), polyglycolic acid (PGA), polylactic acid (PLA), or poly(lactic-co-glycolic acid) (PLGA).

Embodiment 152. The nucleic acid carrier of embodiment 150, wherein the non-antibody scaffold is an affibody, an affilin, an anticalin, an atrimer, an avimer, a bicyclic peptide, a cys-knot, a DARPin, an FN3, a fynomer, a kunitz domain, or an O-body.

Embodiment 153. The nucleic acid carrier of embodiment 150, wherein the antigen is a bacterial antigen, a viral antigen, a fungal antigen, a yeast antigen, a protozoan antigen, or prion.

Embodiment 154. The nucleic acid carrier of embodiment 153, wherein the antigen is from *Acetobacter aurantius, Acinetobacter baumannii, Acinetobacter calcoaceticus, Acinetobacter haemolyticus, Acinetobacter junii, Acinetobacter lwoffii, Actinomyces israelii, Actinomyces viscosus, Aggregatibacter actinomycetemcomitans, Agrobacterium radiobacter, Agrobacterium tumefaciens, Azorhizobium caulinodans, Azotobacter vinelandii, Anaplasma phagocytophilum, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides gingivalis, Bacteroides fragilis, Bacteroides melaninogenicus (Prevotella melaninogenica), Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae (Chlamydia pneumoniae), Chlamydophila psittaci (Chlamydia psittaci), Citrobacter freundii, Citrobacter diverus, Citrobacter koseri, Clostridium botulinum, Clostridium difficile, Clostridium perfringens (Clostridium welchii), Clostridium tetani, Corynebacterium diphtheria, Corynebacterium fusiforme, Coxiella burnetii, Ehrlichia chaffeensis, Enterobacter aerogenes, Enterobacter cloacae, Enterobacter faecalis, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus parainfluenzae, Haemophilus pertussis, Haemophilus vaginalis, Haemophilus influenza, Haemophilus aegyptius, Helicobacter pylori, Klebsiella pneumonia, Klebsiella oxytoca, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella lacunata, Moraxella catarrhalis, Morganella morganii, Mycobacterium avium, Mycobacterium africanum, Mycobacterium bovis, Mycobacterium canetti, Mycobacterium diphtheria, Mycobacterium intracellulare, Mycobacterium leprae, Mycobacterium lepraemurium, Mycobacterium microti, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumonia, Neisseria gonorrhoeae, Neisseria meningitides, Pasteurella multocida, Pasteurella tularensis, Porphyromonas gingivalis, Prevotella melaninogenica (Bacteroides melaninogenicus), Propionibacterium acnes, Proteus mirabillis, Proteus vulgaris, Providencia stuartii, Pseudomonas aeruginosa, Pseudomonas otitidis, Rhizobium radiobacter, Rickettsia prowazekii, Rickettsia psittaci, Rickettsia quintana, Rickettsia rickettsia, Rickettsia trachomae, Rochalimaea henselae, Rochalimaea Quintana, Rothia dentocariosa, Salmonella enteritidis, Salmonella typhi, Salmonella typhimurium, Serratia marcescens, Shigella dysenteriae, Staphylococcus aureus,* methicillin-resistant *Staphylococcus aureus, Staphylococcus pneumoniae, Staphylococcus epidermidis, Staphylococcus saprophyticus, Staphylococcus colmii, Staphylococcus sciuri, Staphylococcus warneri, Stenotrophomonas maltophilia, Streptococcus agalactiae, Streptococcus anginosus, Streptococcus avium, Streptococcus bovis, Streptococcus cricetus, Streptococcus faceium, Streptococcus faecalis, Streptococcus ferus, Streptococcus gallinarum, Streptococcus lactis. Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Streptococcus viridans, Treponema pallidum, Treponema denticola, Vibrio cholera, Vibrio comma, Vibrio parahaemolyticus, Vibrio vulnificus, Wolba-* chia, *Yersinia enterocolitica, Yersinia pestis, Yersinia pseudotuberculosis, Aspergillus fumigatus, Aspergillus flavus, Aspergillus clavatus, Aspergillus niger, Aspergillus terreus, Candida albicans, Candida glabrata, Candida tropicalis, Candida krusei, Candida dubliniensis, Candida parapsilosis, Fusarium solani, Fusarium moniliforme, Fusarium proliferartum, Malessezia pachydermatis, Chrysosporium parvum, Metarhizium anisopliae, Phaeoisaria clematidis,* or *Sarcopodium oculorum.*

Embodiment 155. The nucleic acid carrier of embodiment 153, wherein the antigen is from *Mycobacterium tuberculosis,* Varicella zoster virus, *Corynebacterium diphtheria,* Hepatitis A virus, Hepatitis B virus, Hepatitis C virus, Haemophilis influenza, Human Papillomavirus, Influenza virus, Japanese Encephalitis virus, Measles virus, *Neisseria meningitidis, Mumps virus, Bordetella pertussis, Streptococcus pneumonia,* Poliovirus, Rabies virus, Rotavirus, Rubella virus, Herpes Zoster virus, *Clostridium tetani, Salmonella typhi,* Yellow Fever virus, Ebola virus, avian flu virus, *Bacillus anthracis,* Smallpox virus, or Zika virus.

Embodiment 156. The nucleic acid carrier of embodiment 150, wherein the antibody fragment is Fab, F(ab')$_2$, scFv, tandem scFv, a BiTE, single domain (sdAb) antibody, diabody, single chain diabody, minibody, fusion protein, or scFv-Fc.

Embodiment 157. The nucleic acid carrier of embodiment 150, wherein the antibody, or fragment thereof, is directed to a disease-associated antigen.

Embodiment 158. The nucleic acid carrier of embodiment 157, wherein the disease-associated antigen is a tumor-associated antigen.

Embodiment 159. The nucleic acid carrier of embodiment 158, wherein the tumor-associated antigen is 4-1BB, 5AC, 5T4, A2aR, activin receptor-like kinase 1, AGS-22M6, AKAP4, alpha-fetoprotein, angiopoietin 2, B7-H3, BAFF, BAGE, BCR-ABL, BORIS, CA-125, CA19-9, C242 antigen, carbonic anhydrase 9 (CA-IX), CCR4, CD19, CD20, CD22, CD23 (IgE receptor), CD24, CD28, CD30 (TNFRSF8), CD33, CD37, CD38 (cyclic ADP ribose hydrolase), CD40, CD44 v6, CD51, CD56, CD70, CD71, CD73, CD74, CD79B, CD80, CD137, CD140a, CD152, CD200, CD221, CD274, CEA, ch4D5, CLDN18.2, CS1, CSFIR, CTLA-4, C-X-C chemokine receptor type 4, DLL4, DR5, EBAG9, EGF, EGFR, EGFL7, EpCAM, ERBB2, ERBB3, FAP, fibronectin extra domain-B, folate receptor 1, folate receptor alpha, folate hydrolase, Frizzled receptor, GAGE, GD2 ganglioside, GD3 ganglioside, glioma, glypican 3, GPNMB, gp100, GUCY2C, HER1, HER2/neu, HER3, HGF, HHGFR, histone complex, HLA-DR, human scatter factor receptor kinase, HPV-16, HSP105, IDH1, IDO1, IGF-I, IGF-1 receptor, ILGF2, IL-6, IL-13, integrin αvβ3, integrin α5β1, KIR, LAG-3, Lewis-Y antigen, LY6K, MAGE-1, MAGE-A3, MAGE-C2, MAGE-D4, MAPG, MART-1, Melan-A, MET, MCP-1, mesothelin, MIF, MSLN, MS4A1, mucin CanAg, MUC1, MUC4, MUC16, NG2, N-glycolylneuraminic acid, Notch receptor PD-1, NY-ESO-1, OCAA, PAP, PDGF-R α, PDCD1, PD1, PD-L1, phosphate-sodium co-transporter, phosphatidylserine, PRAME, PSA, RANKL, RON, ROR1, SDC1, Sialyl-Tn, SLAMF7, SPAG-9, SSX1, STEAP1, survivin, TAG-72, telomerase, TEM1, tenascin C, TGF-β, TIM-3, TLR, TAM, TIM-3, TRAIL-R2, TRAIL-R1, TWEAK receptor, tumor specific glycosylation of MUC1, tumor-associated calcium signal transducer 2, tumor antigen CTAA16.88, TYRP1 (glycoprotein 75), VEGF-A, VEGFR2, VEGFR-1, vimentin, VISTA, WT1, and XAGE-1b.

Embodiment 160. The nucleic acid carrier of embodiment 158, wherein the tumor-associated antigen is HER-2, EGFR, CD30, CD20, EpCAM, NG2, CD19, CEA, MUC-1, CA19-9, OCAA, MAPG, TAM, TLR, CD71, ERBB2, VEGF, or glioma.

Embodiment 161. The nucleic acid carrier of embodiment 157, wherein the disease-associated antigen is 1-40-β-amyloid, AOC3 (VAP-1), ACVR2B, angiopoietin 3, beta-amyloid, C5, CCL11 (eotaxin-1), CCR5, CD2, CD3, CD4, CD5, CD11, CD18, CD20, CD23 (IgE receptor), CD25 (a chain of IL-2 receptor), CD28, CD41 (integrin alpha-IIb), CD52, CD125, CD147 (basigin), CD154 (CD40L), CEA-related antigen, clumping factor A, endotoxin, GMCSF receptor α-chain, growth differentiation factor 8, hemagglutinin, HNGF, Hsp90, IGHE, IgE Fc region, IL-1β, IL-4, IL-5, IL-6, IL-9, IL-12, IL-13, IL-17, IL-17A, IL-20, IL-22, IL-23, IL-6 receptor, integrin α4β7, integrin α7β7, integrin α4, integrin αIIbβ3, interferon α/β receptor, interferon gamma-induced protein, IFN-γ, IFN-α, ITGB2 (CD18), LFA-1 (CD11a), LINGO-1, lipoteichoic acid, LOXL2, myelin-associated glycoprotein, myostatin, neural apoptosis-regulated proteinase 1, NGF, NOGO-A, *Oryctolagus cuniculus,* OX-40, PCSK9, phosphatidylserine, platelet-derived growth factor receptor beta, RANKL, Rhesus factor, sclerostin, SOST, sphingosine-1-phosphate, TFPI, TGF-β, TGF beta 2, TGF beta 1, TNF-α, VEGF-A, or VWF.

Embodiment 162. The nucleic acid carrier of embodiment 150, wherein the antibody, or fragment thereof, is directed to a cell surface marker.

Embodiment 163. The nucleic acid carrier of embodiment 162, wherein the cell surface marker is on an immune cell.

Embodiment 164. The nucleic acid carrier of embodiment 163, wherein the immune cell is a T cell, B cell, NK cell, macrophage, TIL, dendritic cell, neutrophil, eosinophil, basophil, or mast cell.

Embodiment 165. The nucleic acid carrier of embodiment 164, wherein the T cell is a CD4$^+$ T cell, CD8$^+$ T cell, helper T cell, cytotoxic T cell, or natural killer T cell; and wherein the B cell is a memory B cell or a plasma cell.

Embodiment 166. The nucleic acid carrier of embodiment 162, wherein the cell surface marker is CD36, CD68, CD83, CD180, CD206 (MRC1-mannose receptor), F4/80 (EGF-TM7 family), CD205, CD56, CD161, CD94:NKG2 heterodimer, KIR/CD158 family, CD335, CD64, CD16, CD3, CD28, CD4, CD25, CD39, Toll-like receptors (TLRs), CD281, CD283, CD284, CD286, CD289, CD282, C-type lectin receptors (CLRs), Fc Receptor, or HSG.

Embodiment 167. The nucleic acid carrier of embodiment 150, comprising one or two of the following:
  a first targeting agent which is an antibody, or fragment thereof, directed to HER2 and a second targeting agent which is an antibody, or fragment thereof, directed to CD64;
  a first targeting agent which is an antibody, or fragment thereof, directed to EGFR and a second targeting agent which is an antibody, or fragment thereof, directed to CD64;
  a first targeting agent which is an antibody, or fragment thereof, directed to EGFR and a second targeting agent which is an antibody, or fragment thereof, directed to PD-1;
  a first targeting agent which is an antibody, or fragment thereof, directed to PD-L1 and a second targeting agent which is an antibody, or fragment thereof, directed to OX40;

a first targeting agent which is an antibody, or fragment thereof, directed to CD30 and a second targeting agent which is an antibody, or fragment thereof, directed to CD16;

a first targeting agent which is an antibody, or fragment thereof, directed to HER2 and a second targeting agent which is an antibody, or fragment thereof, directed to CD3;

a first targeting agent which is an antibody, or fragment thereof, directed to CD20 and a second targeting agent which is an antibody, or fragment thereof, directed to CD3;

a first targeting agent which is an antibody, or fragment thereof, directed to EpCAM and a second targeting agent which is an antibody, or fragment thereof, directed to CD3;

a first targeting agent which is an antibody, or fragment thereof, directed to NG2 and a second targeting agent which is an antibody, or fragment thereof, directed to CD28;

a first targeting agent which is an antibody, or fragment thereof, directed to CD19 and a second targeting agent which is an antibody, or fragment thereof, directed to CD3;

a first targeting agent which is an antibody, or fragment thereof, directed to CD19 and a second targeting agent which is an antibody, or fragment thereof, directed to CD16;

a first targeting agent which is an antibody, or fragment thereof, directed to CEA and a second targeting agent which is an antibody, or fragment thereof, directed to HSG;

a first targeting agent which is an antibody, or fragment thereof, directed to MUC-1 and a second targeting agent which is an antibody, or fragment thereof, directed to HSG;

a first targeting agent which is an antibody, or fragment thereof, directed to CA19-9 and a second targeting agent which is an antibody, or fragment thereof, directed to CD3;

a first targeting agent which is an antibody, or fragment thereof, directed to CEA and a second targeting agent which is an antibody, or fragment thereof, directed to CD3;

a first targeting agent which is an antibody, or fragment thereof, directed to OCAA and a second targeting agent which is an antibody, or fragment thereof, directed to CD3;

a first targeting agent which is an antibody, or fragment thereof, directed to MAPG and a second targeting agent which is an antibody, or fragment thereof, directed to CD28;

a first targeting agent which is an antibody, or fragment thereof, directed to HER2 and a second targeting agent which is an antibody, or fragment thereof, directed to CD16;

a first targeting agent which is an antibody, or fragment thereof, directed to glioma and a second targeting agent which is an antibody, or fragment thereof, directed to CD3;

a first targeting agent which is folic acid or folic acid receptor and a second targeting agent which is an antibody, or fragment thereof, directed to CD3 or CD16; and a first targeting agent which is an antibody, or fragment thereof, directed to PD-1 and a second targeting agent which is an antibody, or fragment thereof, directed to PDL-1 or PDL-2.

Embodiment 168. The nucleic acid carrier of embodiment 150, wherein the label is a chemiluminescent agent, a fluorescent agent, an infrared dye, a radiolabel agent, a metal, a chelating agent, a hapten, or a gene or mRNA encoding a detectable protein.

Embodiment 169. The nucleic acid carrier of embodiment 150, wherein the adjuvant is one or more of a CpG containing oligonucleotide, a ssRNA, a dsRNA, a monophosphate lipid, aluminum, squalene, 3-deacyl-monophosphoryl lipid A, vitamin E, surfactant polysorbate 80, mannide-mono-oleate, SLAG-3, or a galactosylceramide.

Embodiment 170. The nucleic acid carrier of embodiment 169, wherein the CpG containing oligonucleotide is ODN 1585, ODN 1668, ODN 1826, ODN 2006, ODN 2007, ODN 2216, ODN 2336, ODN 2395, ODN M362, AT-ODN-1, AT-ODN-2, ODNBW006, ODN 2088, ODN 4084, ODN INH-1, ODN INH-47, ODN TTAGGG, or G-ODN.

Embodiment 171. The nucleic acid carrier of embodiment 150, wherein the RNA molecule is siRNA, miRNA, mRNA, snRNA, dsRNA, ncRNA, snoRNA, or an aptamer.

Embodiment 172. The nucleic acid carrier of any one of embodiments 134 to 149, wherein the targeting agent is an antigen, an antibody, or a fragment of an antibody, and the oligonucleotide linker conjugating the targeting moiety to the at least one terminal arm is a CpG containing oligonucleotide.

Embodiment 173. The nucleic acid carrier of any one of embodiments 1 to 172, wherein the nucleic acid carrier is cross-linked by a cross-linking agent.

Embodiment 174. The nucleic acid carrier of embodiment 173, wherein the cross-linking agent is mitomycin C, daunamycin, ethidium diazide, cisplatin, an EDC-type compound, or a psoralen.

Embodiment 175. The nucleic acid carrier of embodiment 174, wherein the psoralen is 8-methoxy psoralen, 4,5',8-trimethylpsoralen, 4'-hydroxymethyl-4,5',trimethyl psoralen, 4'-methoxymethyl-4,5',8-trimethyl psoralen, 4'N-phthalimidomethyl-4,5',8-trimethyl psoralen, or 4'-aminomethyl-4,5'-8-trimethyl psoralen hydrochloride.

Embodiment 176. A pharmaceutical composition comprising a nucleic acid carrier of any one of embodiments 1 to 175, and a pharmaceutically acceptable vehicle.

Embodiment 177. A method of making the nucleic acid carrier of embodiment 1 comprising:

hybridizing the first oligonucleotide to the second oligonucleotide; and conjugating the at least one targeting agent to the at least one single-stranded arm.

Embodiment 178. The method of embodiment 177, further comprising conjugating the at least one targeting agent to an oligonucleotide linker prior to conjugating the at least one targeting agent to the at least one single-stranded arm.

Embodiment 179. The method of embodiment 178, wherein the at least one targeting agent/oligonucleotide linker is conjugated to the at least one single-stranded arm by hybridizing the oligonucleotide linker portion of the at least one targeting agent/oligonucleotide linker to a complementary nucleotide sequence of the at least one single-stranded arm.

Embodiment 180. The method of embodiment 177, further comprising conjugating one, two, or three additional targeting agents to other single-stranded arms.

Embodiment 181. A method of making the double monomer nucleic acid carrier of embodiment 55 comprising:
  hybridizing the first oligonucleotide to the second oligonucleotide to form a first nucleic acid carrier;
  hybridizing the third oligonucleotide to the fourth oligonucleotide to form a second nucleic acid carrier;
  hybridizing one single-stranded arm of the first nucleic acid carrier to one single-stranded arm of the second nucleic acid carrier, forming a double monomer nucleic acid carrier comprising six single-stranded arms; and
  conjugating the at least one targeting agent to the at least one single-stranded arm.

Embodiment 182. The method of embodiment 181, further comprising conjugating the at least one targeting agent to an oligonucleotide linker prior to conjugating the at least one targeting agent to the at least one single-stranded arm.

Embodiment 183. The method of embodiment 182, wherein the at least one targeting agent/oligonucleotide linker is conjugated to the at least one single-stranded arm by hybridizing the oligonucleotide linker portion of the at least one targeting agent/oligonucleotide linker to a complementary nucleotide sequence of the at least one single-stranded arm.

Embodiment 184. The method of embodiment 181, further comprising conjugating one, two, three, four, or five additional targeting agents to other single-stranded arms.

Embodiment 185. A method of making the trimer nucleic acid carrier of embodiment 94 comprising:
  hybridizing the first terminal arm of the second oligonucleotide to the first terminal arm of the first oligonucleotide;
  hybridizing the first terminal arm of the third oligonucleotide to the second terminal arm of the first oligonucleotide;
  conjugating the first targeting agent to the second terminal arm of the second oligonucleotide; and
  conjugating the second targeting agent to the second terminal arm of the third oligonucleotide.

Embodiment 186. The method of embodiment 185, further comprising conjugating each targeting agent to an oligonucleotide linker prior to conjugating the targeting agents to the terminal arms.

Embodiment 187. The method of embodiment 186, wherein each targeting agent/oligonucleotide linker is conjugated to the terminal arm by hybridizing the oligonucleotide linker portion of the targeting agent/oligonucleotide linker to a complementary nucleotide sequence of the terminal arm.

Embodiment 188. A method of making the nucleic acid carrier of embodiment 134 comprising:
  conjugating the first targeting agent to the first terminal arm; and
  conjugating the second targeting agent to the second terminal arm.

Embodiment 189. The method of embodiment 188, further comprising conjugating each targeting agent to an oligonucleotide linker prior to conjugating the targeting agents to the terminal arms.

Embodiment 190. The method of embodiment 189, wherein each targeting agent/oligonucleotide linker is conjugated to the terminal arm by hybridizing the oligonucleotide linker portion of the targeting agent/oligonucleotide linker to a complementary nucleotide sequence of the terminal arm.

Embodiment 191. A method of inducing an immune response in a mammal comprising administering to the mammal a nucleic acid carrier of any one of embodiments 1 to 175, or a pharmaceutical composition comprising a nucleic acid carrier of any one of embodiments 1 to 175, wherein the nucleic acid carrier comprises at least two targeting agents chosen from an antigen, a peptide, an antibody or fragment thereof, and an adjuvant.

Embodiment 192. The method of embodiment 191, wherein the antigen is from *Acetobacter aurantius, Acinetobacter baumannii, Acinetobacter calcoaceticus, Acinetobacter haemolyticus, Acinetobacter junii, Acinetobacter lwoffii, Actinomyces israelii, Actinomyces viscosus, Aggregatibacter actinomycetemcomitans, Agrobacterium radiobacter, Agrobacterium tumefaciens, Azorhizobium caulinodans, Azotobacter vinelandii, Anaplasma phagocytophilum, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides gingivalis, Bacteroides fragilis, Bacteroides melaninogenicus (Prevotella melaninogenica), Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae (Chlamydia pneumoniae), Chlamydophila psittaci (Chlamydia psittaci), Citrobacter freundii, Citrobacter diverus, Citrobacter koseri, Clostridium botulinum, Clostridium difficile, Clostridium perfringens (Clostridium welchii), Clostridium tetani, Corynebacterium diphtheria, Corynebacterium fusiforme, Coxiella burnetii, Ehrlichia chaffeensis, Enterobacter aerogenes, Enterobacter cloacae, Enterobacter faecalis, Enterococcus avium, Enterococcus durans, Enterococcus faecalis, Enterococcus faecium, Enterococcus galllinarum, Enterococcus maloratus, Eschericia coli, Francisella tularensis, Fusobacterium nucleatum, Gardnerella vaginalis, Haemophilus ducreyi, Haemophilus parainfluenzae, Haemophilus pertussis, Haemophilus vaginalis, Haemophilus influenza, Haemophilus aegyptius, Helicobacter pylori, Klebsiella pneumonia, Klebsiella oxytoca, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella lacunata, Moraxella catarrhalis, Morganella morganii, Mycobacterium avium, Mycobacterium africanum, Mycobacterium bovis, Mycobacterium canetti, Mycobacterium diphtheria, Mycobacterium intracellulare, Mycobacterium leprae, Mycobacterium lepraemurium, Mycobacterium microti, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumonia, Neisseria gonorrhoeae, Neisseria meningitides, Pasteurella multocida, Pasteurella tularensis, Porphyromonas gingivalis, Prevotella melaninogenica (Bacteroides melaninogenicus), Propionibacterium acnes, Proteus mirabillis, Proteus vulgaris, Providencia stuartii, Pseudomonas aeruginosa, Pseudomonas otitidis, Rhizobium radiobacter, Rickettsia prowazekii, Rickettsia psittaci, Rickettsia quintana, Rickettsia rickettsia, Rickettsia trachomae, Rochalimaea henselae, Rochalimaea Quintana, Rothia dentocariosa, Salmonella enteritidis, Salmonella typhi, Salmonella typhimurium, Serratia marcescens, Shigella dysenteriae, Staphylococcus aureus*, methicillin-resistant *Staphylococcus aureus, Staphylococcus pneumoniae, Staphylococcus epidermidis, Staphylococcus saprophyticus, Staphylococcus colmii, Staphylo-*

*coccus sciuri, Staphylococcus warneri, Stenotrophomonas maltophilia, Streptococcus agalactiae, Streptococcus anginosus, Streptococcus avium, Streptococcus bovis, Streptococcus cricetus, Streptococcus faceium, Streptococcus faecalis, Streptococcus ferus, Streptococcus gallinarum, Streptococcus lactis. Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Streptococcus viridans, Treponema pallidum, Treponema denticola, Vibrio cholera, Vibrio comma, Vibrio parahaemolyticus, Vibrio vulnificus, Wolbachia, Yersinia enterocolitica, Yersinia pestis, Yersinia pseudotuberculosis, Aspergillus fumigatus, Aspergillus flavus, Aspergillus clavatus, Aspergillus niger, Aspergillus terreus, Candida albicans, Candida glabrata, Candida tropicalis, Candida krusei, Candida dubliniensis, Candida parapsilosis, Fusarium solani, Fusarium moniliforme, Fusarium proliferartum, Malessezia pachydermatis, Chrysosporium parvum, Metarhizium anisopliae, Phaeoisaria clematidis,* or *Sarcopodium oculorum.*

Embodiment 193. The method of embodiment 191, wherein the antigen is an antigen from *Mycobacterium tuberculosis*, Varicella zoster virus, *Corynebacterium diphtheria*, Hepatitis A virus, Hepatitis B virus, Hepatitis C virus, Haemophilis influenza, Human Papillomavirus, Influenza virus, Japanese Encephalitis virus, Measles virus, *Neisseria meningitidis, Mumps virus, Bordetella pertussis, Streptococcus pneumonia*, Poliovirus, Rabies virus, Rotavirus, Rubella virus, Herpes Zoster virus, *Clostridium tetani, Salmonella typhi*, Yellow Fever virus, Ebola virus, avian flu virus, *Bacillus anthracis*, Smallpox virus, or Zika virus.

Embodiment 194. The method of any one of embodiments 191 to 193, wherein the antibody fragment is Fab, F(ab')$_2$, scFv, tandem scFv, a BiTE, single domain (sdAb) antibody, diabody, single chain diabody, minibody, fusion protein, or scFv-Fc.

Embodiment 195. The method of any one of embodiments 191 to 194, wherein the antibody, or fragment thereof, is directed to a cell surface marker.

Embodiment 196. The method of embodiment 195, wherein the cell surface marker is on an immune cell.

Embodiment 197. The method of embodiment 196, wherein the immune cell is a T cell, B cell, NK cell, macrophage, TIL, dendritic cell, neutrophil, eosinophil, basophil, or mast cell.

Embodiment 198. The method of embodiment 197, wherein the T cell is a CD4$^+$ T cell, CD8$^+$ T cell, helper T cell, cytotoxic T cell, or natural killer T cell; and wherein the B cell is a memory B cell or a plasma cell.

Embodiment 199. The method of embodiment 195, wherein the cell surface marker is CD36, CD68, CD83, CD180, CD206 (MRC1-mannose receptor), F4/80 (EGF-TM7 family), CD205, CD56, CD161, CD94:NKG2 heterodimer, KIR/CD158 family, CD335, CD64, CD16, CD3, CD28, CD4, CD25, CD39, Toll-like receptors (TLRs), CD281, CD283, CD284, CD286, CD289, CD282, C-type lectin receptors (CLRs), Fc Receptor, or HSG.

Embodiment 200. The method of any one of embodiments 191 to 199, wherein the adjuvant is one or more of a CpG containing oligonucleotide, a ssRNA, a dsRNA, a monophosphate lipid, aluminum, squalene, 3-deacyl-monophosphoryl lipid A, vitamin E, surfactant polysorbate 80, mannide-mono-oleate, SLAG-3, or a galactosylceramide.

Embodiment 201. The method of embodiment 200, wherein the CpG containing oligonucleotide is ODN 1585, ODN 1668, ODN 1826, ODN 2006, ODN 2007, ODN 2216, ODN 2336, ODN 2395, ODN M362, AT-ODN-1, AT-ODN-2, ODNBW006, ODN 2088, ODN 4084, ODN INH-1, ODN INH-47, ODN TTAGGG, and G-ODN.

Embodiment 202. The method of any one of embodiments 191 to 201, wherein the oligonucleotide linker conjugating the targeting moiety to the terminal arm is a CpG containing oligonucleotide.

Embodiment 203. A method of treating a mammal having cancer comprising administering to the mammal a nucleic acid carrier of any one of embodiments 1 to 175, or a pharmaceutical composition comprising a nucleic acid carrier of any one of embodiments 1 to 175, wherein the nucleic acid carrier comprises at least two targeting agents chosen from an antibody, or fragment thereof, and a label.

Embodiment 204. The method of embodiment 203, wherein the antibody fragment is Fab, F(ab')$_2$, scFv, tandem scFv, a BiTE, single domain (sdAb) antibody, diabody, single chain diabody, minibody, fusion protein, or scFv-Fc.

Embodiment 205. The method of embodiment 203 or embodiment 204, wherein a first antibody, or fragment thereof, is directed to a tumor-associated antigen.

Embodiment 206. The method of embodiment 205, wherein the tumor-associated antigen is 4-1BB, 5AC, 5T4, A2aR, activin receptor-like kinase 1, AGS-22M6, AKAP4, alpha-fetoprotein, angiopoietin 2, B7-H3, BAFF, BAGE, BCR-ABL, BORIS, CA-125, CA19-9, C242 antigen, carbonic anhydrase 9 (CA-IX), CCR4, CD19, CD20, CD22, CD23 (IgE receptor), CD24, CD28, CD30 (TNFRSF8), CD33, CD37, CD38 (cyclic ADP ribose hydrolase), CD40, CD44 v6, CD51, CD56, CD70, CD71, CD73, CD74, CD79B, CD80, CD137, CD140a, CD152, CD200, CD221, CD274, CEA, ch4D5, CLDN18.2, CS1, CSFIR, CTLA-4, C-X-C chemokine receptor type 4, DLL4, DR5, EBAG9, EGF, EGFR, EGFL7, EpCAM, ERBB2, ERBB3, FAP, fibronectin extra domain-B, folate receptor 1, folate receptor alpha, folate hydrolase, Frizzled receptor, GAGE, GD2 ganglioside, GD3 ganglioside, glioma, glypican 3, GPNMB, gp100, GUCY2C, HER1, HER2/neu, HER3, HGF, HHGFR, histone complex, HLA-DR, human scatter factor receptor kinase, HPV-16, HSP105, IDH1, IDO1, IGF-I, IGF-1 receptor, ILGF2, IL-6, IL-13, integrin αvβ3, integrin α5β1, KIR, LAG-3, Lewis-Y antigen, LY6K, MAGE-1, MAGE-A3, MAGE-C2, MAGE-D4, MAPG, MART-1, Melan-A, MET, MCP-1, mesothelin, MIF, MSLN, MS4A1, mucin CanAg, MUC1, MUC4, MUC16, NG2, N-glycolylneuraminic acid, Notch receptor PD-1, NY-ESO-1, OCAA, PAP, PDGF-R α, PDCD1, PD1, PD-L1, phosphate-sodium co-transporter, phosphatidylserine, PRAME, PSA, RANKL, RON, ROR1, SDC1, Sialyl-Tn, SLAMF7, SPAG-9, SSX1, STEAP1, survivin, TAG-72, telomerase, TEM1, tenascin C, TGF-β, TIM-3, TLR, TAM, TIM-3, TRAIL-R2, TRAIL-R1, TWEAK receptor, tumor specific glycosylation of MUC1, tumor-associated calcium signal transducer 2, tumor antigen CTAA16.88, TYRP1 (glycoprotein 75), VEGF-A, VEGFR2, VEGFR-1, vimentin, VISTA, WT1, or XAGE-1b.

Embodiment 207. The method of embodiment 205, wherein the tumor-associated antigen is HER-2, EGFR, CD30, CD20, EpCAM, NG2, CD19, CEA, MUC-1, CA19-9, OCAA, MAPG, or glioma.

Embodiment 208. The method of any one of embodiments 203 to 207, wherein a second antibody, or fragment thereof, is directed to a cell surface marker.

Embodiment 209. The method of embodiment 208, wherein the cell surface marker is on an immune cell.

Embodiment 210. The method of embodiment 209, wherein the immune cell is a T cell, B cell, NK cell, macrophage, TIL, dendritic cell, neutrophil, eosinophil, basophil, or mast cell.

Embodiment 211. The method of embodiment 210, wherein the T cell is a CD4$^+$ T cell, CD8$^+$ T cell, helper T cell, cytotoxic T cell, or natural killer T cell; and wherein the B cell is a memory B cell or a plasma cell.

Embodiment 212. The method of embodiment 208, wherein the cell surface marker is CD36, CD68, CD83, CD180, CD206 (MRC1-mannose receptor), F4/80 (EGF-TM7 family), CD205, CD56, CD161, CD94:NKG2 heterodimer, KIR/CD158 family, CD335, CD64, CD16, CD3, CD28, CD4, CD25, CD39, Toll-like receptors (TLRs), CD281, CD283, CD284, CD286, CD289, CD282, C-type lectin receptors (CLRs), Fc Receptor, or HSG.

Embodiment 213. The method of any one of embodiments 203 to 212, wherein the nucleic acid carrier comprises:
  a first targeting agent which is an antibody, or fragment thereof, directed to HER2 and a second targeting agent which is an antibody, or fragment thereof, directed to CD64, and wherein the cancer is breast, ovarian, or prostrate;
  a first targeting agent which is an antibody, or fragment thereof, directed to EGFR and a second targeting agent which is an antibody, or fragment thereof, directed to CD64, and wherein the cancer is a solid tumor, lung, or colorectal;
  a first targeting agent which is an antibody, or fragment thereof, directed to EGFR and a second targeting agent which is an antibody, or fragment thereof, directed to PD-1, and wherein the cancer is triple negative breast cancer;
  a first targeting agent which is an antibody, or fragment thereof, directed to PD-L1 and a second targeting agent which is an antibody, or fragment thereof, directed to OX-40, and wherein the cancer is breast cancer;
  a first targeting agent which is an antibody, or fragment thereof, directed to CD30 and a second targeting agent which is an antibody, or fragment thereof, directed to CD16, and wherein the cancer is Hodgkin's disease;
  a first targeting agent which is an antibody, or fragment thereof, directed to HER2 and a second targeting agent which is an antibody, or fragment thereof, directed to CD3, and wherein the cancer is metastatic breast cancer or prostrate;
  a first targeting agent which is an antibody, or fragment thereof, directed to CD20 and a second targeting agent which is an antibody, or fragment thereof, directed to CD3, and wherein the cancer is non-Hodgkin lymphoma or multiple myeloma;
  a first targeting agent which is an antibody, or fragment thereof, directed to EpCAM and a second targeting agent which is an antibody, or fragment thereof, directed to CD3, and wherein the cancer is ovarian, gastric, colon, colorectal, breast, non-small cell lung cancer, adenocarcinoma of the lung, small cell lung cancer;
  a first targeting agent which is an antibody, or fragment thereof, directed to NG2 and a second targeting agent which is an antibody, or fragment thereof, directed to CD28, and wherein the cancer is melanoma;
  a first targeting agent which is an antibody, or fragment thereof, directed to CD19 and a second targeting agent which is an antibody, or fragment thereof, directed to CD3, and wherein the cancer is B-precursor acute lymphoblastic leukemia or non-Hodgkin lymphoma;
  a first targeting agent which is an antibody, or fragment thereof, directed to CD19 and a second targeting agent which is an antibody, or fragment thereof, directed to CD16, and wherein the cancer is non-Hodgkin lymphoma;
  a first targeting agent which is an antibody, or fragment thereof, directed to CEA and a second targeting agent which is an antibody, or fragment thereof, directed to HSG, and wherein the cancer is colorectal, lung carcinoma, pancreas carcinoma, stomach carcinoma, ovary carcinoma, uterus carcinoma, breast carcinoma, or melanoma;
  a first targeting agent which is an antibody, or fragment thereof, directed to MUC-1 and a second targeting agent which is an antibody, or fragment thereof, directed to HSG, and wherein the cancer is invasive pancreatic adenocarcinoma;
  a first targeting agent which is an antibody, or fragment thereof, directed to CA19-9 and a second targeting agent which is an antibody, or fragment thereof, directed to CD3, and wherein the cancer is a CA19-9-positive tumor;
  a first targeting agent which is an antibody, or fragment thereof, directed to CEA and a second targeting agent which is an antibody, or fragment thereof, directed to CD3, and wherein the cancer is ovarian;
  a first targeting agent which is an antibody, or fragment thereof, directed to OCAA and a second targeting agent which is an antibody, or fragment thereof, directed to CD3, and wherein the cancer is ovarian;
  a first targeting agent which is an antibody, or fragment thereof, directed to MAPG and a second targeting agent which is an antibody, or fragment thereof, directed to CD28, and wherein the cancer is metastatic melanoma;
  a first targeting agent which is an antibody, or fragment thereof, directed to HER2 and a second targeting agent which is an antibody, or fragment thereof, directed to CD16, and wherein the cancer is a HER-2 positive tumor;
  a first targeting agent which is an antibody, or fragment thereof, directed to glioma and a second targeting agent which is an antibody, or fragment thereof, directed to CD3, and wherein the cancer is a glioma; and
  a first targeting agent which is folic acid or folic acid receptor and a second targeting agent which is an antibody, or fragment thereof, directed to CD3 or CD16, and wherein the cancer is small cell lung carcinoma, breast, or ovarian.

Embodiment 214. The method of any one of embodiments 203 to 213, wherein the label is a chemiluminescent agent, a fluorescent agent, an infrared dye, a radiolabel agent, a metal, a chelating agent, a hapten, or a gene or mRNA encoding a detectable protein.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning-A Laboratory Manual, 2nd ed., Cold Spring Harbor Press (1989), using commercially available reagents, except where otherwise noted.

EXAMPLES

Example 1: Manufacture and Use of a DNA Monomer Containing Two Different Targeting Antibodies Step 1: Conjugation of Two Antibodies (Ag1Ab and Ag2Ab) with Thiol End-Labeled DNA Oligonucleotides (OligoA and OligoB) Complementary to the Two Different Open ssDNA Sequences on the DNA Monomer The buffer containing each of the two antibodies is exchanged into 1× PBS using standard buffer exchange spin columns.

Each of two 72-mer DNA oligonucleotides containing a 3' thiol group are separately reduced using tris(2-carboxyethyl) phosphine (TCEP) for 1 hour at room temperature. TCEP is removed by ethanol precipitation of the oligonucleotide, and the oligonucleotide is resuspended in water.

Amines on each antibody are activated by using LC-SMCC, a heterobifunctional cross-linker with N-hydroxysuccinimide (NHS) ester and maleimide groups that allow covalent conjugation of amine- and sulfhydryl labeled molecules. A 50× LC-SMCC solution is used to treat each antibody for 1 hour at room temperature. Excess LC-SMCC is removed via desalting columns.

The two resuspended thiol DNA oligonucleotide are added to the appropriate activated antibodies at a ratio of 1.2:1 of DNA oligonucleotide molecules to antibody protein molecules in the following configuration:

DNA OligoA is added to Antibody AgAb1 to form AgAb1-OligoA conjugate

DNA OligoB is added to Antibody AgAb2 to form AgAb2-OligoB conjugate

The conjugations are allowed to proceed for 1 hour at room temperature.

The conjugation reactions are separately purified using TAC resin. Ten wash buffer column volumes, ten elution buffer column volumes, and five water column volumes fractions are collected for each conjugate.

Purification fractions that contain each conjugate (based upon running fractions on a gel) are independently pooled for each conjugate and concentrated using 10K MWCO spin concentrators.

Final protein and oligonucleotide concentrations for each conjugate are determined via a protein quantitation assays and spectroscopy.

Step 2: Assembly of the DNA Monomer

Two 97-mer DNA oligonucleotides (Strand 1 and Strand 2) are designed and ordered from a commercial DNA synthesizer company (e.g. IDT). The oligonucleotides are designed to share a region of sequence complementarity located in the central portion of each oligonucleotide comprising 31 nucleotides. When the two oligonucleotides anneal to form the monomer, the resulting structure can be described as having a central double-stranded region (i.e., "waist") bordered by four single-stranded arms of two different sequences complementary to the OligoA and OligoB sequences previously utilized for conjugation to antibodies AgAb1 and AbAb2, with the different sequences arranged at each end of the monomer opposite to one another. This waist-plus-arms structure comprises the basic 3DNA® monomer. Base-pairing of the arms to the two 72-mer oligonucleotides comprising the antibody-oligonucleotide conjugate described above is accomplished by adding stoichiometric concentrations of the antibody-oligonucleotide conjugate to the previously assembled monomers.

The following components are added to a polypropylene tube:

| | |
|---|---|
| ssDNA Strand 1 in water at 1000 ng/μL | 100.0 μL (100,000 ng) |
| ssDNA Strand 2 in water at 1000 ng/μL | 100.0 μL (100,000 ng) |
| 10× PBS | 30.0 μL |
| Nuclease free water | 50.0 μL |
| AgAb1-OligoA Conjugate at 10,000 ng/μL as oligo | 10.0 μL (100,000 ng as oligo) |
| AgAb2-OligoB Conjugate at 10,000 ng/μL as oligo | 10.0 μL (100,000 ng as oligo) |

All reactants are added together and gently heated at 37° C. for 10 minutes, and then slowly cooled to room temperature.

Example 2: Manufacture and Use of a DNA "Double-Monomer" Containing Two Different Targeting Antibodies Antibody-oligonucleotide conjugates are synthesized as in Example 1.

Double-monomers are assembled in a manner similar to simple DNA monomers, albeit using three additional DNA oligonucleotides, two of which are additional 97-mer DNA oligonucleotide of different sequences, and one of which is a 64-mer "bridging" oligonucleotide used to attach the two independent monomeric structures.

The following components are added to a polypropylene tube:

| | |
|---|---|
| ssDNA Strand 1 in water at 1000 ng/μL | 100.0 μL (100,000 ng) |
| ssDNA Strand 2 in water at 1000 ng/μL | 100.0 μL (100,000 ng) |
| ssDNA Strand 3 in water at 1000 ng/μL | 100.0 μL (100,000 ng) |
| ssDNA Strand 4 in water at 1000 ng/μL | 100.0 μL (100,000 ng) |
| Bridging Oligo in water at 10,000 ng/μL | 5.0 μL (50,000 ng) |
| 10× PBS | 50.0 μL |
| Nuclease free water | 5.0 μL |
| AgAb1-OligoA Conjugate at 10,000 ng/μL as oligo | 20.0 μL (200,000 ng as oligo) |
| AgAb2-OligoB Conjugate at 10,000 ng/μL as oligo | 20.0 μL (200,000 ng as oligo) |

All reactants are added together and gently heated at 37° C. for 10 minutes, and then slowly cooled to room temperature.

Example 3: Manufacture and Use of a "Trimer" Dendrimer Configuration Containing Two Different Targeting Antibodies Antibody-oligonucleotide conjugates are synthesized as in Example 1.

The dendrimer "trimer" configuration is assembled in a manner similar to simple DNA monomers, albeit using three DNA oligonucleotides, all of which are 97-mer DNA oligonucleotides of different sequences.

The following components are added to a polypropylene tube:

| | |
|---|---|
| ssDNA Strand 1 in water at 1000 ng/μL | 100.0 μL (100,000 ng) |
| ssDNA Strand 2 in water at 1000 ng/μL | 100.0 μL (100,000 ng) |

| | |
|---|---|
| ssDNA Strand 3 in water at 1000 ng/µL | 100.0 µL (100,000 ng) |
| 10× PBS | 40.0 µL |
| Nuclease free water | 40.0 µL |
| AgAb1-OligoA Conjugate at 10,000 ng/µL as oligo | 10.0 µL (100,000 ng as oligo) |
| AgAb2-OligoB Conjugate at 10,000 ng/µL as oligo | 10.0 µL (100,000 ng as oligo) |

All reactants are added together and gently heated at 37° C. for 10 minutes, and then slowly cooled to room temperature.

Example 4: Manufacture and Use of a dsDNA Linker Containing Two Different Targeting Antibodies Antibody-oligonucleotide conjugates are synthesized as in Example 1.

A dsDNA linker is assembled in a manner similar to simple DNA monomers, albeit using one 97-mer DNA oligonucleotide and a second 31-mer DNA oligonucleotide complementary to the "waist" region of the first DNA oligonucleotide.

The following components are added to a polypropylene tube:

| | |
|---|---|
| 97-mer ssDNA oligo in water at 1000 ng/µL | 100.0 µL (100,000 ng) |
| 31-mer ssDNA oligo in water at 300 ng/µL | 100.0 µL (30,000 ng) |
| 10× PBS | 30.0 µL |
| Nuclease free water | 50.0 µL |
| AgAb1-OligoA Conjugate at 10,000 ng/µL as oligo | 10.0 µL (100,000 ng as oligo) |
| AgAb2-OligoB Conjugate at 10,000 ng/µL as oligo | 10.0 µL (100,000 ng as oligo) |

All reactants are added together and gently heated at 37° C. for 10 minutes, and then slowly cooled to room temperature.

Example 5: Anti-EPCAM, Anti-CD3 Monomer Formulation for In Vitro and In Vivo Immune Oncology Assays Step 1: Conjugation of Two Antibodies (Anti-EPCAM and Anti-CD3) with Thiol End-Labeled DNA Oligonucleotides (OligoA and OligoB) Complementary to the Two Different Open ssDNA Sequences on the DNA Monomer The buffer containing each of the two antibodies is exchanged into 1× PBS using standard buffer exchange spin columns.

Each of two 72-mer DNA oligonucleotides containing a 3' thiol group are separately reduced using TCEP for 1 hour at room temperature. TCEP is removed by ethanol precipitation of the oligonucleotide, and the oligonucleotide is resuspended in water.

Amines on each antibody are activated by using LC-SMCC, a heterobifunctional cross-linker with N-hydroxysuccinimide (NHS) ester and maleimide groups that allow covalent conjugation of amine- and sulfhydryl-labeled molecules. A 50× LC-SMCC solution is used to treat each antibody for 1 hour at room temperature. Excess LC-SMCC is removed via desalting columns.

The two resuspended thiol DNA oligonucleotide are added to the appropriate activated antibodies at a ratio of 1.2:1 of DNA oligonucleotide molecules to antibody protein molecules in the following configuration:

DNA OligoA is added to Anti-EPCAM to form anti-EPCAM-OligoA conjugate

DNA OligoB is added to Anti-CD3 to form Anit-CD3-OligoB conjugate The conjugations are allowed to proceed for 1 hour at room temperature.

The conjugation reactions are separately purified using TAC resin. Ten wash buffer column volumes, ten elution buffer column volumes, and five water column volumes fractions are collected for each conjugate.

Purification fractions that contain each conjugate (based upon running fractions on a gel) are independently pooled for each conjugate and concentrated using 10K MWCO spin concentrators.

Final protein and oligonucleotide concentrations for each conjugate are determined via a protein quantitation assays and spectroscopy.

Step 2: Assembly of the DNA Monomer

Two 97-mer DNA oligonucleotides (Strand 1 and Strand 2) are designed and ordered from a commercial DNA synthesizer company (e.g. IDT). The oligonucleotides are designed to share a region of sequence complementarity located in the central portion of each oligonucleotide comprising 31 nucleotides. When the two oligonucleotides anneal to form the monomer, the resulting structure can be described as having a central double-stranded region (i.e., "waist") bordered by four single-stranded arms of two different sequences complementary to the OligoA and OligoB sequences previously utilized for conjugation to anti-EPCAM and anti-CD3 antibodies, with the different sequences arranged at each end of the monomer opposite to one another. This waist-plus-arms structure comprises the basic 3DNA® monomer. Base-pairing of the arms to the two 72-mer oligos comprising the antibody-oligonucleotide conjugate described above is accomplished by adding stoichiometric concentrations of the antibody-oligonucleotide conjugate to the previously assembled monomers.

The following components are added to a polypropylene tube:

| | |
|---|---|
| ssDNA Strand 1 in water at 1000 ng/µL | 100.0 µL (100,000 ng) |
| ssDNA Strand 2 in water at 1000 ng/µL | 100.0 µL (100,000 ng) |
| 10× PBS | 30.0 µL |
| Nuclease free water | 50.0 µL |
| Anti-EPCAM-OligoA Conjugate at 10,000 ng/µL as oligo | 10.0 µL (100,000 ng as oligo) |
| Anti-CD3-OligoB Conjugate at 10,000 ng/µL as oligo | 10.0 µL (100,000 ng as oligo) |

All reactants are added together and gently heated at 37° C. for 10 minutes, and then slowly cooled to room temperature.

In Vitro Cell Based Assays:

Confirmation of binding: OVCAR3 (EPCAM positive), A2780 (EPCAM negative) and peripheral blood mononuclear cells (PMBCs) are used to measure antibody binding. A total of $1\times10^6$ cells are washed with phosphate buffered saline (PBS; 137 mmol/L NaCl, 2.7 mmol/L KCl, 10 mmol/L $Na_2HPO_4$, and 2 mmol/L $KH_2PO_4$) and incubated in 100 µl EPCAM/CD3 monomer (100 µg/ml as antibody in PBS) for 30 minutes at room temperature and then are washed twice with PBS. Fluorescein isothiocyanate conjugated antibody against human IgG is used for detecting the EPCAM/CD3 monomer. The antibody is diluted at 1:200 and added to the cells for 30 minutes at room temperature.

Cells are analyzed using fluorescence activated cell sorting (CytoFLEX; Beckman Coulter, Pasadena, CA, USA).

Induction of T-cell activation: Freshly prepared PBMCs ($2\times10^6$ cells/ml) are added to each well of a six well flat bottom plate (Molecular Devices, Sunnyvale, CA, USA). Each well contains 2 ml RPMI 1640 (HyClone, Logan, Utah, USA) with 10% fetal calf serum (FCS) only (control wells), or with 10% FCS and unconjugated CD3 antibody (30 ng/ml) or with 10% FCS and Bispecific EPCAM/CD3 dendrimer (10 ng/ml). PBMCs are incubated for 24 hours and the activation of PBMCs was measured using flow cytometric analysis. The expression levels of CD25 and CD69 on T cells were detected by flow cytometry to evaluate the T-lymphocyte activation ability of EPCAM/CD3 monomer.

Luminex liquid chip analysis: A luminex liquid chip array is used to determine the release of inflammatory cytokines IL-2, IL-4, tumor necrosis factor (TNF) α and interferon (IFN) γ from PBMCs induced by EPCAM/CD3 monomer. A human MultiAnalyte Profiling Base kit (R&D Systems, Minneapolis, Minnesota, USA) is used for detection. Freshly prepared PBMCs ($2\times10^6$ cells/ml) are added to each well of a 96 well flat bottom plate. Each well contains 100 µl complete media alone (control wells), or with complete media containing 1 µg/ml CD28 Ab (TGN1412; eBioscience, San Diego, CA, USA), unconjugated CD3 Ab or EPCAM/CD3 monomer. Each assay is performed in triplicate. The PBMCs are incubated at 37° C. under 5% $CO_2$ for 72 hours and 50-µl aliquots of media were collected for the liquid chip array. Briefly, the diluted microparticle mixture is resuspended and 50 µl of the mixture is added to each well of the microplate. Subsequently, 50 µl of the standard or sample is added to each well and incubated for 3 hours at room temperature using a vacuum manifold device designed to accommodate a microplate. Subsequently, 50 µl diluted biotin antibody cocktail is added to each well and the plate is incubated for 1 hour at room temperature, with agitation. Diluted streptavidin phycoerythrin (50 µl) is added to each well and the plate is incubated for 30 minutes at room temperature, with agitation at 500 rpm. The microparticles are resuspended by adding 100 µl wash buffer to each well and incubating for 2 minutes, with agitating at 500 rpm. The fluorescence signal is read using a Luminex 100 analyzer (Luminex Corp., Austin, TX, USA) within 90 minutes.

In vitro Cytotoxicity assay: The EPCAM-positive cell line OVCAR3 is used as positive target cells and the A2780 cells are used as negative controls. Cytotoxicity is measured using a CytoTox 96® Non-Radioactive Cytotoxicity assay kit (Promega, Madison, Wisconsin, USA) using RPMI 1640 complete medium with 5% FCS in a round bottom 96 well plates. Briefly, PBMCs are added as effector cells to each well at gradient concentrations, followed by the addition of the target cells ($1\times10^4$). EPCAM/CD3 monomer (100 ng/ml) is added to achieve final effector cell to target cell (E:T) ratios of 100:1, 50:1, 10:1 and 1:1. The cell mixtures are incubated at 37° C. under 5% $CO_2$ for 4 hours, following which 50 µl aliquots of media are transferred to fresh 96 well flat bottom plates for the LDH release assay. The percentage of cell lysis is calculated as the specific release (%)=(experimental release-effector spontaneous release-target spontaneous release)/(target maximum release-target spontaneous release)×100. Each assay is performed in triplicate In vivo Mouse Model studies: In vivo experiments are performed in female 6- to 10-week-old C57BL/6 and immunodeficient NOD/SCID mice characterized by T cell, B cell, and natural killer cell deficiency and lack of macrophage function (The Jackson Laboratory, Bar Harbor, ME). The mice are maintained under sterile and standardized environmental conditions (20° F. room temperature, 10% relative humidity, 12 hours light dark rhythm). For each animal, $2.5\times10^6$ or $5\times10^6$ human PBMC are mixed with $5\times10^6$ OVCAR3 ovarian carcinoma cells in a final volume of 0.2 mL PBS. The PBMC effector-to-target cell mixture (E:T, 1:2 or 1:1) is s.c. injected into the right flank of each NOD/SCID mouse. Two different variants of the tumor model (early treatment and established tumor model) are used. For the early treatment model, four to six animals per group are i.v. treated with EPCAM/CD3 monomer, PBS control vehicle, or monomer only (untargeted) control starting 1 hour after OVCAR/PBMC inoculation at varying doses and treatment is repeated for 4 consecutive days. In the established tumor model, initiation of treatment is delayed until s.c. growing OVCAR3 tumors are developed (50-200 $mm^3$). Six animals per group are treated starting at days 4, 8, and 12, respectively, and treatment is repeated for 4 consecutive days. Tumors are measured on the indicated days with a caliper in two perpendicular dimensions and tumor volumes are calculated according to the following formula: tumor volume= $[(width^2\times length)/2]$.

Example 6: Synthesis of 2 Layer Nucleic Acid Carrier from Synthetic DNA Strands Containing Both Phosphodiester (PO) and Phosphorothioate (PS)

Preparation of PO-Monomers:

An equal mass of the following synthetic PO-DNA strands was added to a polypropylene tube to assemble the indicated monomers: A Monomer-PO: PO-Strands 1 and 2; B' Monomer-PO: PO-Strands 3 and 4; and B" Monomer-PO: PO-Strands 4 and 5. Appropriate quantities of saline buffer were added to the monomer preparations. The monomer preparations were heated to >70° C. and allowed to slowly cool to room temperature.

Assembly of 1 Layer Nucleic Acid Carrier:

To a quantity of A Monomer-PO, 2.0 molar masses of each of the B'-PO and B"-PO Monomers were added. 4,5,8 trimethylpsoralen was added, mixed well, and incubated at 42° C. for 30 minutes. The preparation was exposed to UVA light. The preparation was chilled at 4° C. for 30 minutes, centrifuged at 1500×G for 10 minutes at 4° C. to remove precipitated 4,5,8 trimethylpsoralen.

Purification of 1 Layer Nucleic Acid Carrier:

The final 1-layer product was separated from unincorporated components and residual cross-linking reagent using differential centrifugation.

Preparation of PS-Monomers:

An equal mass of the following synthetic PS-DNA strands was added to a polypropylene tube to assemble the indicated monomers: C' Monomer-PS: PS-Strands 2 and 6; and C" Monomer-PS: PS-Strands 2 and 7. Appropriate quantities of saline were added to the monomer preparations. The monomer preparations were heated to >70° C. and allowed to slowly cool to room temperature.

Assembly of PO/PS-2 Layer Nucleic Acid Carrier:

To the 1 layer-PO preparation, 1.2 molar masses each of the C'-PS and C"-PS Monomers was added. 4,5,8 trimethylpsoralen was added, mixed well, and incubated at 42° C. for 30 minutes. The preparation was exposed to UVA light. The preparation was chilled at 4° C. for 30 minutes, and centrifuged at 1500×G for 10 minutes at 4° C.

Purification of 2 Layer Nucleic Acid Carrier:

The final 2-layer product was separated from unincorporated components and residual cross-linking reagent using differential centrifugation.

Example 7: Serum Degradation Study of 2 Layer Nucleic Acid Carrier from Synthetic DNA Strands Containing all Phosphodiester (PO) Nucleic Acid Bases and Strands Containing Both Phosphodiester (PO) and Phosphorothioate (PS) Nucleic Acid Bases Preparation of PO-Monomers:

An equal mass of the following synthetic PO-DNA strands was added to a polypropylene tube to assemble the indicated monomers: A Monomer-PO: PO-Strands 1 and 2; B' Monomer-PO: PO-Strands 3 and 4; and B" Monomer-PO: PO-Strands 4 and 5. Appropriate quantities of saline buffer were added to the monomer preparations. The monomer preparations were heated to >70° C. and allowed to slowly cool to room temperature.

Assembly of 1 Layer Nucleic Acid Carrier:

To a quantity of A Monomer-PO, 2.0 molar masses of each of the B'-PO and B"-PO Monomers were added. 4,5,8 trimethylpsoralen was added, mixed well, and incubated at 42° C. for 30 minutes. The preparation was exposed to UVA light. The preparation was chilled at 4° C. for 30 minutes, centrifuged at 1500×G for 10 minutes at 4° C. to remove precipitated 4,5,8 trimethylpsoralen.

Purification of 1 Layer Nucleic Acid Carrier:

The final 1-layer product was separated from unincorporated components and residual cross-linking reagent using differential centrifugation.

Preparation of PS-Monomers:

Synthetic DNA strands are synthesized having every other base being a Phosphorothioate (PSEO). An equal mass of the following synthetic PSEO-DNA strands was added to a polypropylene tube to assemble the indicated monomers: C' Monomer-PSEO: PSEO-Strands 2 and 6; and C" Monomer-PSEO: PSEO-Strands 2 and 7. Appropriate quantities of saline were added to the monomer preparations. The monomer preparations were heated to >70° C. and allowed to slowly cool to room temperature.

Assembly of PO/PSEO-2 Layer Nucleic Acid Carrier:

To the 1 layer-PO preparation, 1.2 molar masses each of the C'-PSEO and C"-PSEO Monomers was added. 4,5,8 trimethylpsoralen was added, mixed well, and incubated at 42° C. for 30 minutes. The preparation was exposed to UVA light. The preparation was chilled at 4° C. for 30 minutes, and centrifuged at 1500×G for 10 minutes at 4° C.

Assembly of PO-2 Layer Nucleic Acid Carrier:

This material was prepared as described above.

Serum Degradation of PO-2 Layer Nucleic Acid Carrier and PO/PSEO-2 Layer Nucleic Acid Carrier in 25% Mouse Serum:

5 µg of each 2 layer nucleic acid carrier (PO and PO/PSEO) were mixed with PBS and then added to a micro-centrifuge tube containing 25 µl of mouse serum bringing the total volume up to 100 µl. A 4 hour time point was started first; 2 hours later a 2 hour time point was initiated; 1 hour later the 1 hour time point was started and so on, such that all time points ended simultaneously at the appropriate time interval after 4 hours. The alkaline lysis step was immediately performed on all samples with buffers from the Qiagen miniprep kit (P/N 12381) the tubes were quickly inverted following the addition of each buffer: Buffer 1 (100 µl), Buffer 2 (200 µl) & Buffer 3 (350 µl). The buffers were added sequentially and the tubes were vortexed for 10 seconds once all 3 buffers had been added. The tubes were then incubated at 65° C. for 5 minutes. The tubes were centrifuged at 12,000 g for 3 minutes to remove the white cloudy material, the supernatant was transferred to a new tube. A 1× volume of formamide (~700 µl) was added to each tube. The tubes were inverted several times in order to ensure appropriate mixing. The tubes were then incubated at 65° C. for an additional 5 minutes. A 1× volume phenol/chloroform/isoamyl alcohol was added to each sample. The tubes were vortexed for 30 seconds and then centrifuged for 5 minutes at 12,000 g, the aqueous layer was removed and transferred to a new tube. A Sodium Acetate (NaOAc) ethanol precipitation was performed next by adding a 1/10 volume of 3M NaOAc followed by 2.5 volumes of ethanol. The samples were centrifuged at 12,000 g for 30 minutes at 4° C. and the liquid was carefully removed to ensure a very small faint pellet remains intact. The pellets were washed with 70% ethanol (100 µl) and centrifuged for 5 minutes at 12,000 g. The 70% ethanol wash was carefully removed and the tubes were placed in a 37° C. incubator with caps open to allow the samples to dry for about 10 minutes. The pellets were re-suspended in 30 µl of PBS, the DNA concentration was determined on a NanoDrop and about 2 µl of sample from each time point was loaded on a Lonza Pre-cast Fast 1.2% agarose gel.

Figure 6:
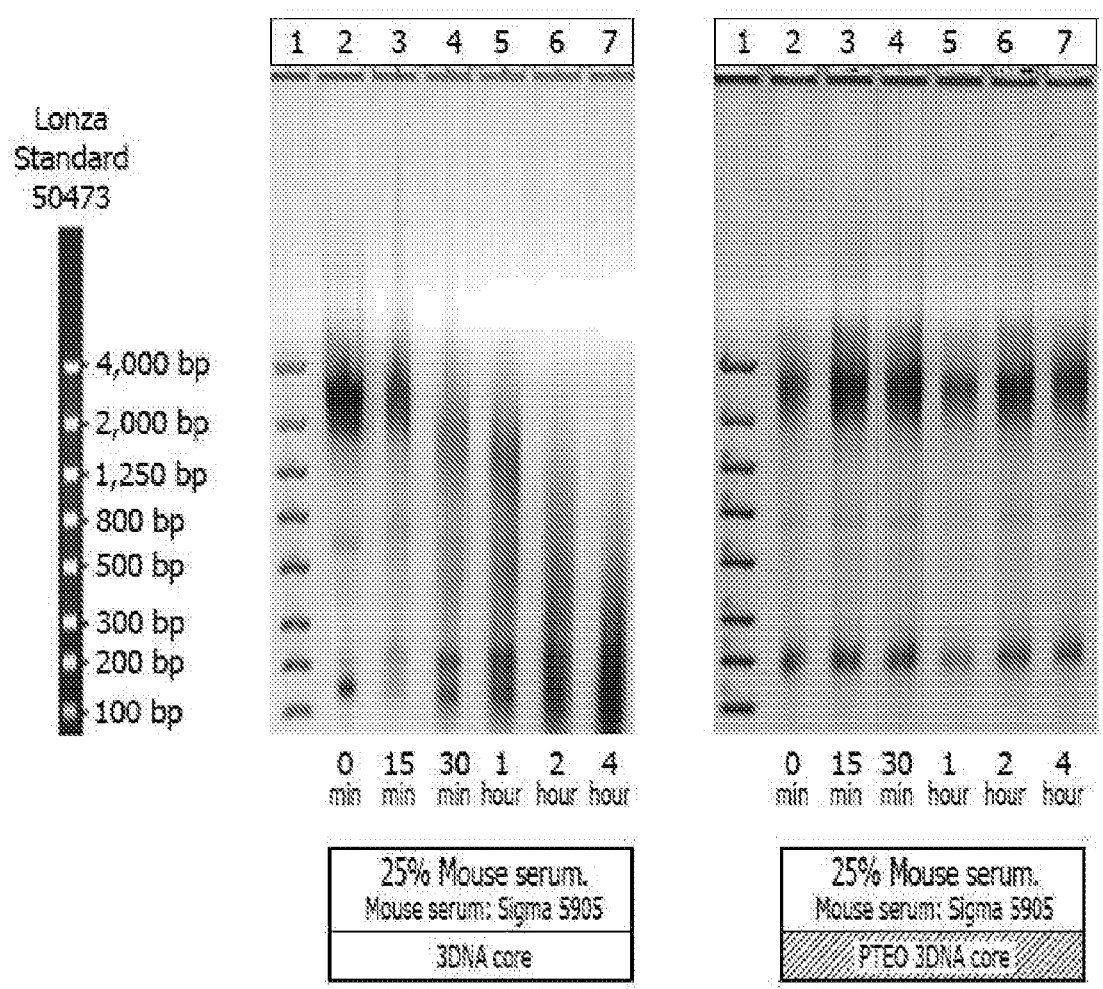
FIG. 6 shows representative serum degradation gel analysis of naked nucleic acid carrier versus phosphorothioate naked nucleic acid carrier in mouse serum.

The agarose gel images from this experiment are presented in FIG. 6. PO-2 layer nucleic acid carrier starts to show degradation at 15 minutes and was completely degraded at 4 hour time point (loss of the high molecular weight band at about 3000 bp). In comparison, the PO/PSEO-2 Layer nucleic acid carrier showed no degradation even at the 4 hour time point. This indicates that by using modified bases not only can the serum degradation profile be changed but also the resulting clearance profile may be subsequently altered thereby modulating the PK/PD profile of the carrier.

Example 8: Comparison of EPCAM-MMAE Antibody Drug Conjugate to EPCAM-MMAE Antibody Drug Conjugate Coupled to Dendrimer Preparation of EGFR-MMAE Antibody Drug Conjugate (ADC):

Monomethyl auristatin (MMAE) is an antimitotic agent that inhibits the polymerization of tubulin. MMAE is coupled to an antibody via a maleimide linkage to cysteines on the antibody and is cleaved once delivered to the cell by protease in the cell. MMAE was linked to and antibody that recognizes epithelial cell adhesion molecule (EPCAM). EPCAM monoclonal antibody (mAb) is obtained from BioXCell and concentrated/buffer exchanged to 10 mg/ml in a PBS pH 7.4, 1 mM EDTA buffer using Amicon Spin filters (100 kD MWCO, Millipore). To generate free sulfhydryls, the EGFR antibody is reduced using a 10 mM TCEP solution (ThermoFisher) with the TCEP at a 2.75-fold molar excess over antibody. TCEP is added, vortexed briefly, and incubated at 37° C. for 2 hours. For example, using 0.067 mM Ab, TCEP is added to a final concentration of 0.18 mM. To conjugate the drug to the prepared antibody, maleimide-MMAE (containing a val-cit cleavable linker, MC-Val-Cit-PAB-MMAE, ALB Technology Limited) is diluted to 10 mM final concentration in DMSO. The drug is then added to the prepared (reduced) EPCAM antibody at a 10-fold molar excess of drug over antibody (for example, for 0.067 mM Ab, drug is added to a final concentration of 0.67 mM). MMAE is added, vortexed briefly, and incubated at 10° C.

for 30 minutes. After incubation, excess drug is removed and the ADC is buffer exchanged into PBS pH 7.4 using Zeba Spin desalting columns (ThermoFisher). The EPCAM-MMAE ADC is then filter sterilized (0.22μ filter, Millipore) and a BCA assay is performed to determine protein concentration using BGG standards (ThermoFisher).

Coupling of EPCAM-MMAE Antibody to Dendrimer Binding Oligonucleotide:

In order to attach the EGFR-MMAE to a dendrimer, an oligonucleotide complementary to one or more outer arms of the DNA dendrimer is prepared. EPCAM-MMAE-oligonucleotide conjugate is prepared by first reducing the DNA dendrimer binding oligonucleotide (DBO) that contains a 3' thiol using 50 mM TCEP for 1 hour. After reduction, the TCEP is removed via ethanol precipitation, the oligonucleotide is resuspended in nuclease-free water, and the concentration obtained via A260. To prepare the ADC for conjugation, 2.0 mg of EPCAM ADC (antibody plus drug molecules of DAR=2-4) in 1×PBS pH 7.4 is placed into a 15.0 ml conical tube. To the ADC, LC-SMCC cross-linker is added at a 12.5× molar ratio of crosslinker-to-ADC, and the mixture is reacted for 1 hour at room temperature. Excess crosslinker is removed from the ADC reaction mixture using Zeba gel filtration columns. Next, the TCEP-reduced oligo and LC-SMCC-modified ADC are combined at a 1:1.2 antibody-to-oligo ratio and allowed to react at room temperature for 1 hour then placed at 4° C. overnight. Excess unconjugated oligonucleotide is removed using thiophilic adsorption chromatography. The impure ADC-oligo conjugate is diluted 10-fold (by volume) in Buffer A (5.0 mM Sodium Phosphate pH 7.0, 500 mM Potassium Sulfate) and loaded onto a TAC column equilibrated with Buffer A. The TAC column is washed with 10 CVs Buffer A then the ADC-oligo conjugate is eluted with 10 CVs Buffer B (5.0 mM Sodium Phosphate pH 7.0). The TAC column is further washed with 5 CVs nuclease-free water. Column fractions are analyzed via 10% native-TBE gel electrophoresis and gels are stained with Syber gold. Fractions that contained ADC-conjugate free of contaminating oligo are pooled and concentrated via a Amicon spin concentrator (10000 MWCO). At the end of concentration, PBS pH 7.4 buffer is added to a final of 0.2× PBS. The amount of remaining unconjugated oligo is determined via 10% native-TBE gel electrophoresis and comparing to a standard curve of known-amounts of unmodified oligo and computed via densitometry. Finally, the protein concentration of the ADC-oligo conjugate is determined via BCA assay, with BGG used as the protein standard.

Binding of EPCAM to DNA Dendrimer:

EPCAM-MMAE oligonucleotide conjugate is combined with a 2-layer DNA dendrimer to formulate a EPCAM-MMAE ADC-DNA dendrimer (12 antibodies per DNA dendrimer) in a final concentration of 1×PBS, pH 7.4 at a concentration of 1 mg/ml as EPCAM-MMAE.

EGFR-MMAE Compared to EGFR-MMAE on Dendrimer In Vivo:

In vivo Xenograft Mouse Model studies: In vivo experiments are carried out in female 6- to 10-week-old immunodeficient NOD/SCID mice (The Jackson Laboratory, Bar Harbor, ME). The mice are maintained under sterile and standardized environmental conditions (20+/−° C. room temperature, 50+/−10% relative humidity, 12 hours light dark rhythm). For each animal, $5 \times 10^6$ OVCAR3 ovarian carcinoma cells in a final volume of 0.2 mL PBS. The cells are s.c. injected into the right flank of each NOD/SCID mouse. In the established tumor model, initiation of treatment is delayed until s.c. growing OVCAR3 tumors are developed (50-200 $mm^3$). Once tumors develop to the appropriate size range, the animals are randomly divided into groups. Eight animals per group are treated starting at days 4, 8, and 12, respectively; using 1 mg/kg as EPCAM MMAE mAb for both the DNA dendrimer bound and unbound EPCAM-MMAE ADCs. Treatment is repeated every 4 days for a total of 1-3 treatments. As a control, antibody without drug is used. Tumors are measured on the indicated days with a caliper in two perpendicular dimensions and tumor volumes are calculated according to the following formula: tumor volume=$[(width^2 \times length)/2]$.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A nucleic acid carrier comprising a first and a second oligonucleotide:
   wherein a central portion of each of the first and second oligonucleotides is complementary to each other, forming a double-stranded region, wherein the double-stranded region is from about 25 to about 35 bases in length;
   wherein the two terminal portions of the first oligonucleotide are not complementary to the two terminal portions of the second oligonucleotide, forming four single-stranded arms; and
   an antibody, conjugated to at least one single-stranded arm of the four single-stranded arms.

2. The nucleic acid carrier of claim 1, wherein the antibody is a Fab, F(ab')₂, scFv, tandem scFv, a BiTE, single domain (sdAb) antibody, diabody, single chain diabody, minibody, fusion protein, or scFv-Fc.

3. The nucleic acid carrier of claim 1, wherein the antibody, or antigen binding fragment thereof, binds to 4-1BB, 5AC, 5T4, A2aR, activin receptor-like kinase 1, AGS-22M6, AKAP4, alpha-fetoprotein, angiopoietin 2, B7-H3, BAFF, BAGE, BCR-ABL, BORIS, CA-125, CA19-9, C242 antigen, carbonic anhydrase 9 (CA-IX), CCR4, CD19, CD20, CD22, CD23 (IgE receptor), CD24, CD28, CD30 (TNFRSF8), CD33, CD37, CD38 (cyclic ADP ribose hydrolase), CD40, CD44 v6, CD51, CD56, CD70, CD71, CD73, CD74, CD79B, CD80, CD137, CD140a, CD152, CD200, CD221, CD274, CEA, ch4D5, CLDN18.2, CSI, CSFIR, CTLA-4, C-X-C chemokine receptor type 4, DLL4, DR5, EBAG9, EGF, EGFR, EGFL7, EpCAM, ERBB2, ERBB3, FAP, fibronectin extra domain-B, folate receptor 1, folate receptor alpha, folate hydrolase, Frizzled receptor, GAGE, GD2 ganglioside, GD3 ganglioside, glioma, glypican 3, GPNMB, gp100, GUCY2C, HER1, HER2/neu, HER3, HGF, HHGFR, histone complex, HLA-DR, human scatter factor receptor kinase, HPV-16, HSP105, IDH1, IDO1, IGF-I, IGF-1 receptor, ILGF2, IL-6, IL-13, integrin αvβ3, integrin α5β1, KIR, LAG-3, Lewis-Y antigen, LY6K, MAGE-1, MAGE-A3, MAGE-C2, MAGE-D4, MAPG, MART-1, Melan-A, MET, MCP-1, mesothelin, MIF, MSLN, MS4A1, mucin CanAg, MUC1, MUC4, MUC16, NG2, N-glycolylneuraminic acid, Notch receptor PD-1, NY-ESO-1, OCAA, PAP, PDGF-R α, PDCD1, PD1, PD-L1, phosphate-sodium co-transporter, phosphatidylserine, PRAME, PSA, RANKL, RON, ROR1, SDC1, Sialyl-Tn, SLAMF7, SPAG-9, SSX1, STEAP1, survivin, TAG-72, telomerase, TEM1, tenascin C, TGF-β, TIM-3, TLR, TAM, TIM-3, TRAIL-R2, TRAIL-R1, TWEAK receptor, tumor specific glycosylation of MUC1, tumor-associated calcium signal transducer 2, tumor antigen CTAA16.88, TYRP1 (glycoprotein 75), VEGF-A, VEGFR2, VEGFR-1, vimentin, VISTA, WT1, or XAGE-1b.

4. The nucleic acid carrier of claim 1, wherein the antibody is selected from an anti-HER2 antibody, an anti-CD64 antibody, an anti-EGFR antibody, or an anti-PD-1 antibody.

5. The nucleic acid carrier of claim 1, wherein the single stranded arm is from about 25 to about 35 bases in length.

6. The nucleic acid carrier of claim 1, wherein the first and the second oligonucleotide each, independently, further comprise one or two hinge segments joining one or both of the terminal arms to the double stranded region, wherein each hinge segment, independently, comprises 1, 2, 3, or 4 nucleotides.

7. A pharmaceutical composition comprising the nucleic acid carrier of claim 1.

* * * * *

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: CpG containing oligonucleotide

<400> SEQUENCE: 1
ggggtcaacg ttgagggggg                                          20

<210> SEQ ID NO 2
<211> LENGTH: 20
<212> TYPE: DNA
<213> ORGANISM: Artificial Sequence
<220> FEATURE:
<223> OTHER INFORMATION: CpG containing oligonucleotide

<400> SEQUENCE: 2
```

```
tccatgacgt tcctgatgct                                              20

<210> SEQ ID NO 3
<211> LENGTH: 20
<212> TYPE: DNA
<213> ORGANISM: Artificial Sequence
<220> FEATURE:
<223> OTHER INFORMATION: CpG containing oligonucleotide

<400> SEQUENCE: 3
tccatgacgt tcctgacgtt                                              20

<210> SEQ ID NO 4
<211> LENGTH: 24
<212> TYPE: DNA
<213> ORGANISM: Artificial Sequence
<220> FEATURE:
<223> OTHER INFORMATION: CpG containing oligonucleotide

<400> SEQUENCE: 4
tcgtcgtttt gtcgttttgt cgtt                                         24

<210> SEQ ID NO 5
<211> LENGTH: 21
<212> TYPE: DNA
<213> ORGANISM: Artificial Sequence
<220> FEATURE:
<223> OTHER INFORMATION: CpG containing oligonucleotide

<400> SEQUENCE: 5
tcgtcgttgc gttttgtcgt t                                            21

<210> SEQ ID NO 6
<211> LENGTH: 20
<212> TYPE: DNA
<213> ORGANISM: Artificial Sequence
<220> FEATURE:
<223> OTHER INFORMATION: CpG containing oligonucleotide

<400> SEQUENCE: 6
gggggacgat cgtcggggggg                                             20

<210> SEQ ID NO 7
<211> LENGTH: 21
<212> TYPE: DNA
<213> ORGANISM: Artificial Sequence
<220> FEATURE:
<223> OTHER INFORMATION: CpG containing oligonucleotide

<400> SEQUENCE: 7
ggggacgacg tcgtgggggg g                                            21

<210> SEQ ID NO 8
<211> LENGTH: 22
<212> TYPE: DNA
<213> ORGANISM: Artificial Sequence
<220> FEATURE:
<223> OTHER INFORMATION: CpG containing oligonucleotide

<400> SEQUENCE: 8
tcgtcgtttt cggcgcgcgc cg                                           22

<210> SEQ ID NO 9
<211> LENGTH: 28
<212> TYPE: DNA
```

```
<213> ORGANISM: Artificial Sequence
<220> FEATURE:
<223> OTHER INFORMATION: CpG containing oligonucleotide

<400> SEQUENCE: 9
tcgtcgtcgt tcgaacgacg acgttgat                                      28

<210> SEQ ID NO 10
<211> LENGTH: 20
<212> TYPE: DNA
<213> ORGANISM: Artificial Sequence
<220> FEATURE:
<223> OTHER INFORMATION: CpG containing oligonucleotide

<400> SEQUENCE: 10 tataattta atttccaaga                                                20

<210> SEQ ID NO 11
<211> LENGTH: 20
<212> TYPE: DNA
<213> ORGANISM: Artificial Sequence
<220> FEATURE:
<223> OTHER INFORMATION: CpG containing oligonucleotide

<400> SEQUENCE: 11 tataatttt accaactagc                                                20

<210> SEQ ID NO 12
<211> LENGTH: 23
<212> TYPE: DNA
<213> ORGANISM: Artificial Sequence
<220> FEATURE:
<223> OTHER INFORMATION: CpG containing oligonucleotide

<400> SEQUENCE: 12
tcgacgttcg tcgttcgtcg ttc                                           23

<210> SEQ ID NO 13
<211> LENGTH: 15
<212> TYPE: DNA
<213> ORGANISM: Artificial Sequence
<220> FEATURE:
<223> OTHER INFORMATION: CpG containing oligonucleotide

<400> SEQUENCE: 13
tcctggcggg gaagt                                                    15

<210> SEQ ID NO 14
<211> LENGTH: 12
<212> TYPE: DNA
<213> ORGANISM: Artificial Sequence
<220> FEATURE:
<223> OTHER INFORMATION: CpG containing oligonucleotide

<400> SEQUENCE: 14
cctggatggg aa                                                       12

<210> SEQ ID NO 15
<211> LENGTH: 24
<212> TYPE: DNA
<213> ORGANISM: Artificial Sequence
<220> FEATURE:
<223> OTHER INFORMATION: CpG containing oligonucleotide

<400> SEQUENCE: 15
cctggatggg aattcccatc cagg                                          24
```

```
<210> SEQ ID NO 16
<211> LENGTH: 24
<212> TYPE: DNA
<213> ORGANISM: Artificial Sequence
<220> FEATURE:
<223> OTHER INFORMATION: CpG containing oligonucleotide

<400> SEQUENCE: 16
tatggatttt aattaaaatc cata                                          24

<210> SEQ ID NO 17
<211> LENGTH: 25
<212> TYPE: DNA
<213> ORGANISM: Artificial Sequence
<220> FEATURE:
<223> OTHER INFORMATION: CpG containing oligonucleotide

<400> SEQUENCE: 17
tttagggtta gggttagggt taggg                                         25

<210> SEQ ID NO 18
<211> LENGTH: 21
<212> TYPE: DNA
<213> ORGANISM: Artificial Sequence
<220> FEATURE:
<223> OTHER INFORMATION: CpG containing oligonucleotide

<400> SEQUENCE: 18
ctcctattgg gggtttccta t                                             21
```